(12) United States Patent
Isono et al.

(10) Patent No.: US 8,809,451 B2
(45) Date of Patent: Aug. 19, 2014

(54) FLUORINATED DICARBOXYLIC ACID DERIVATIVE AND POLYMER OBTAINED THEREFROM

(75) Inventors: Yoshimi Isono, Kawagoe (JP); Satoru Narizuka, Saitama (JP); Hidehisa Nanai, Tokyo (JP); Kazuhiro Yamanaka, Tachikawa (JP)

(73) Assignee: Central Glass Company, Limited, Ube-shi (JP)

( * ) Notice: Subject to any disclaimer, the term of this patent is extended or adjusted under 35 U.S.C. 154(b) by 166 days.

(21) Appl. No.: 13/201,766

(22) PCT Filed: Feb. 18, 2010

(86) PCT No.: PCT/JP2010/052425
§ 371 (c)(1),
(2), (4) Date: Aug. 16, 2011

(87) PCT Pub. No.: WO2010/095678
PCT Pub. Date: Aug. 26, 2010

(65) Prior Publication Data
US 2011/0301305 A1 Dec. 8, 2011

(30) Foreign Application Priority Data
Feb. 20, 2009 (JP) ................................. 2009-038347

(51) Int. Cl.
| | | |
|---|---|---|
| B01F 17/00 | (2006.01) | |
| C07C 17/00 | (2006.01) | |
| C07C 19/00 | (2006.01) | |
| C07C 19/08 | (2006.01) | |
| C07C 21/00 | (2006.01) | |
| C07C 22/00 | (2006.01) | |
| C07C 23/00 | (2006.01) | |
| C07C 25/00 | (2006.01) | |
| C07C 25/13 | (2006.01) | |
| C07C 69/00 | (2006.01) | |
| C07C 69/34 | (2006.01) | |
| C07C 69/52 | (2006.01) | |
| C07C 69/63 | (2006.01) | |
| C08G 18/42 | (2006.01) | |
| C08G 63/00 | (2006.01) | |
| C08G 63/02 | (2006.01) | |
| C08G 63/60 | (2006.01) | |
| C08G 63/68 | (2006.01) | |
| C08G 63/682 | (2006.01) | |
| C08G 67/00 | (2006.01) | |
| C08G 69/00 | (2006.01) | |
| C08G 69/26 | (2006.01) | |
| C08L 67/00 | (2006.01) | |
| C08L 67/02 | (2006.01) | |
| C08L 73/00 | (2006.01) | |
| C08L 77/00 | (2006.01) | |
| C08L 79/00 | (2006.01) | |

(52) U.S. Cl.
USPC ........... 524/599; 524/601; 524/603; 524/604; 524/606; 528/271; 528/272; 528/299; 528/335; 560/3; 560/192; 560/205; 560/226; 560/227; 570/101; 570/123; 570/125; 570/127; 570/129; 570/130

(58) Field of Classification Search
USPC .......... 524/599, 601, 603, 604, 606; 528/271, 528/272, 299, 335; 560/3, 192, 205, 226, 560/227; 570/101, 123, 125, 127, 129, 130
See application file for complete search history.

(56) References Cited

U.S. PATENT DOCUMENTS

2006/0106193 A1 5/2006 Moriyama et al.
2009/0030173 A1 1/2009 Narizuka et al.

FOREIGN PATENT DOCUMENTS

| JP | 5-112635 A | 5/1993 |
|---|---|---|
| JP | 2003-12596 A | 1/2003 |
| JP | 2003-12601 A | 1/2003 |
| JP | 2004-143416 A | 5/2004 |
| JP | 2006-56939 A | 3/2006 |
| JP | 2007-119503 A | 5/2007 |
| JP | 2009-41002 A | 2/2009 |
| WO | WO 2004/039863 A1 | 5/2004 |
| WO | WO 2008/140840 A1 | 11/2008 |

OTHER PUBLICATIONS

Extended European Search Report dated Jul. 29, 2013 {Eight (8) pages}.
Bocknack, Brian M. et al., "Chiral beta-diketonate ligands of 'pseudo planar chiral' topology: enantioselective synthesis and transition metal complexation", Tetrahedron, Jun. 27, 2005, pp. 6266-6275, vol. 61 No. 26, Elsevier Ltd., Amsterdam, NL, XP027861272.
Ashwood, Michael S. et al., "Copper-mediated reaction of 2-halopyridines with ethyl bromodifluoroacetate", Tetrahedron Letters, Dec. 9, 2002, pp. 9271-9273, vol. 43 No. 50, Elsevier Science Ltd., Amsterdam, NL, XP027330794.

(Continued)

Primary Examiner — Patrick Niland
(74) Attorney, Agent, or Firm — Crowell & Moring LLP

(57) ABSTRACT

According to the present invention, a polymer is obtained by polycondensation of a fluorinated dicarboxylic acid derivative of the general formula (M-1) or an acid anhydride of the fluorinated dicarboxylic acid with a polyfunctional compound having two to four reactive groups corresponding in reactivity to carbonyl moieties of the fluorinated dicarboxylic acid derivative or acid anhydride.

[Chem. 134]

$$AOCF_2C-Q-CF_2COA'$$  (M-1)

In the above formula, Q represents a divalent organic group having a substituted or unsubstituted aromatic ring; and A and A' each independently represent an organic group. This polymer exhibits a sufficiently low dielectric constant for use as a semiconductor protection film and has the capability of forming a film at a relatively low temperature of 250° C. or lower.

11 Claims, No Drawings

(56) References Cited

OTHER PUBLICATIONS

T. W. Bastock et al., "The Reactions of Aromatic Compounds with Bromine Trifluoride (2) : Octafluoronaphthalene", Journal of Fluorine Chemistry vol. 8, 1976, pp. 11-22.

Zhen-Yu Yang, "Synthesis of new α,α,β,β-tetrafluoroesters", Journal of Fluorine Chemistry, vol. 125, 2004, pp. 763-765.

K. Sato et al., "Reactons of ethyl bromodifluoroacetate in the presence of copper powder", Journal of Fluorine Chemistry, vol. 125, 2004, pp. 509-515.

International Search Report dated Mar. 30, 2010 with English translation (four (4) pages).

PCT/ISA/237 (three (3) pages), Mar. 30, 2010.

US 8,809,451 B2

FLUORINATED DICARBOXYLIC ACID DERIVATIVE AND POLYMER OBTAINED THEREFROM

TECHNICAL FIELD

The present invention relates to a novel fluorinated dicarboxylic acid derivative and a novel polymer obtained therefrom.

BACKGROUND ART

Polyesters, polyamides, polyimides and polybenzoxazoles have been developed as high-reliability organic polymer materials and have a large market in the field of electronic devices, engineering plastics for automotive and aerospace uses, environmental technologies such as photovoltaic power generation systems and fuel cells, medical materials and optical materials. Various kinds and forms of such polymers, including polyamides typified by Nylon and Kevlar (tradenames), polyarylates used as liquid crystalline polymers, polyimides typified by Kapton (tradename) and polybenzoxazoles typified by Zylon (tradename), are already put into practical use.

Polymerization processes depend on the combination of monomers. In the case of production of the polyester, there can be used a process of polycondensation of a dicarboxylic acid with a diol in the presence of a condensation agent or a process of conversion of a dicarboxylic acid to an acid chloride or ester followed by polycondensation of the acid chloride or ester with a diol. In the case of production of the polyamide, there can be used a process of polycondensation of a dicarboxylic acid with a diamine in the presence of a condensation agent or a process of conversion of a dicarboxylic acid to an acid chloride or ester followed by polycondensation of the acid chloride or ester with a diamine. In the case of production of the polyimide, there can be used a process of polymerization of a diamine with a tetracarboxylic dianhydride followed by dehydration ring closure of the polymerization product. In the case of production of the polybenzoxazole, there can be used a process of polycondensation of a dicarboxylic acid with a bisaminophenol in the presence of a condensation agent or a process of conversion of a dicarboxylic acid to an acid chloride or ester followed by polycondensation of the acid chloride or ester with a bisaminophenol.

Among others, attentions are being given to aromatic polyesters, aromatic polyamides and derivatives thereof in the field of printed circuit boards, semiconductors and displays because of their high reliability and good dimensional stability. On the other hand, there has been a continuing demand for fine patterning to achieve high density packaging and thin film formation in the applications of these aromatic polyester and polyamide materials. The aromatic polyester and polyamide materials are required to attain not only higher reliability such as lower water absorption but also improved electrical characteristics such as lower dielectric constant.

The introduction of a fluorine atom into aromatic polymers leads to improvements in polymer performance, such as hydrophobic and lipophobic properties, low water absorption, corrosion resistance, transparency, photosensitivity, low refractive index and low dielectric constant, without sacrificing high reliability. The fluorinated aromatic polymers have thus been developed and put into practical use in a wide range of material fields, notably advanced material fields. Further, it has been attempted to introduce fluorine into diamine monomers for condensed polymers. There are in practical use fluorinated aromatic polymers derived from aromatic diamine and dihydroxy monomers in each of which a fluorine atom or a trifluoromethyl group substitutes for a hydrogen atom on the aromatic ring and derived from bis(hydroxyamine) monomers each of which has a hexafluoroisopropenyl group as a central atomic group between aromatic hydroxyamines.

Patent Document 1 discloses a fluorinated aromatic polyamide that combines visible light transparency with dimensional stability by the introduction of a trifluoromethyl group directly to an aromatic ring of the rigid polyamide framework. By the effect of such fluorine introduction, the polymerization reaction can proceed even in an organic solvent although it has typically been necessary to carry out the polymerization reaction in sulfuric acid. The application of the fluorinated aromatic polyamide is however limited as the framework of the aromatic polyamide is so rigid that the polyamide needs to be heated at a high temperature of 280° C. or higher to form a flexible film thereof.

Patent Document 2 discloses a rigid, fully aromatic polyester that combines light transparency in the 850 nm band range with high thermal resistance by the substitution of all of hydrogen atoms with a fluorine atom or a trifluoromethyl group. As the framework of the aromatic polyester is rigid, the polymerization temperature needs to be 300° C. or higher to increase the polymerization degree of the polyester.

Non-Patent Document 1 discloses a dicarboxylic acid monomer in which carboxyl groups are bonded to the ortho positions of a fully fluorinated benzene ring via fluorinated methylene groups, but makes no mention about the production of a polymer from the dicarboxylic acid monomer. Further, Non-Patent Document 2 discloses bis(2-ethoxycarbonyl-1,1,2,2-tetrafluoroethyl)benzene but also does not make any mention about the production of a polymer therefrom.

PRIOR ART DOCUMENTS

Patent Documents

Patent Document 1: International Publication No. 2004/039863
Patent Document 2: Japanese Laid-Open Patent Publication No. 5-112635

Non-Patent Documents

Non-Patent Document 1: Journal of Fluorine Chemistry, 8 (1976), 11-22
Non-Patent Document 2: Journal of Fluorine Chemistry, 125 (2004), 763-765

Problems to be Solved by the Invention

Each of the fluorinated aromatic polymers of Patent Documents 1 and 2 exhibits very high reliability and tends to have a high curing temperature as mentioned above. On the other hand, there has been a demand to develop a film of a high-reliability polymer curable at 250° C. or lower as a protection film for a semiconductor chip where very high reliability is required due to the fact that the thermal resistance of semiconductor chips is in practice often set to 250° C. or lower.

It is accordingly an object of the present invention to provide a polycondensation polymer capable of forming a film at a relatively low temperature of 250° C. or lower and showing a sufficiently low dielectric constant for use as a protection film for a semiconductor device.

Means for Solving the Problems

The present inventors have made extensive researches to solve the above problems and, as a result, have invented a novel fluorinated dicarboxylic acid or fluorinated dicarboxylic acid derivative in which carboxyl groups are bonded to an aromatic ring via a fluorinated methylene group and a novel polymer obtained therefrom. The polyester and polyamide of Patent Documents 1 and 2 are each obtained by polycondensation of a phthalic acid derivative in which two carboxyl groups are directly substituted on an aromatic ring. The curing (polymerization) reaction of such a phthalic acid derivative proceeds at a temperature exceeding 250° C. By contrast, the fluorinated dicarboxylic acid of the present invention, in which the carboxyl groups are bonded to the aromatic ring via the difluoromethylene groups, undergoes polymerization by heating at 250° C. or lower so that the resulting polymer can form a film (thin coating film) with a low dielectric constant and good flexibility. The present inventors have further found that a heterocyclic polymer obtained by partial ring closure of the polyester or polyamide of the present invention also combines a low dielectric constant with good flexibility.

Namely, the present invention includes the following aspects.

[1] A polymer obtained by polycondensation of a fluorinated dicarboxylic acid derivative of the general formula (M-1) or an acid anhydride of the fluorinated dicarboxylic acid with a polyfunctional compound having two to four reactive groups corresponding in reactivity to carbonyl moieties of the fluorinated dicarboxylic acid derivative or acid anhydride:

[Chem. 1]

$$AOCF_2C\text{-}Q\text{-}CF_2COA' \qquad (M\text{-}1)$$

where Q represents a divalent organic group having a substituted or unsubstituted aromatic ring; each of $CF_2COA$ and $CF_2COA'$ is bonded to a carbon atom of the aromatic ring; a hydrogen atom on the aromatic ring may be substituted with either a fluorine atom, a chlorine atom, a hydroxyl group, an amino group, a nitro group, a cyano group, a hydroxycarbonyl group, a $C_1\text{-}C_6$ straight, branched or cyclic alkyl group (whose hydrogen atom may be substituted with a hydroxyl group or a fluorine atom), a $C_1\text{-}C_6$ straight, branched or cyclic alkoxy group, a $C_1\text{-}C_6$ straight, branched or cyclic alkoxycarbonyl group or a substituted or unsubstituted monovalent aromatic ring group; and A and A' each independently represent a hydroxyl group, a fluorine atom, a chlorine atom, a bromine atom, an iodine atom, a $C_1\text{-}C_6$ straight, branched or cyclic alkoxy group or a $C_6\text{-}C_{10}$ substituted or unsubstituted aryloxy group and may form an active ester moiety together with a CO group (carbonyl group) in the formula.

[2] The polymer according to Inventive Aspect 1, wherein the divalent organic group Q is a divalent organic group of the following general formula (a):

[Chem. 2]

where $Ar^1$ each independently represent a substituted or unsubstituted aromatic ring; a hydrogen atom on the aromatic ring may be substituted with either a fluorine atom, a chlorine atom, a hydroxyl group, an amino group, a nitro group, a cyano group, a hydroxylcarbonyl group, a $C_1\text{-}C_6$ straight, branched or cyclic alkyl group (whose hydrogen atom may be substituted with a hydroxyl group or a fluorine atom), a $C_1\text{-}C_6$ straight, branched or cyclic alkoxy group, a $C_1\text{-}C_6$ straight, branched or cyclic alkoxycarbonyl group or a substituted or unsubstituted monovalent aromatic ring group; $Y^1$ represents a single bond, or a divalent group made up of either one, or two or more of the same kind or different kinds, selected from the group consisting of $CH_2$, $CH_2CH_2$, $CH_2CH_2CH_2$, O, S, $C(CH_3)_2$, $C(CF_3)_2$, $SO_2$, CO, NH, COO (ester) and CONH; p represents an integer of 0 to 3; and two free sites of the divalent organic group are bonded to the same carbon atom or different carbon atoms of the aromatic ring.

[3] The polymer according to Inventive Aspect 1, wherein the divalent organic group Q is a divalent organic group of the following general formula (b):

[Chem. 3]

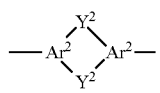

where $Ar^2$ each independently represent a substituted or unsubstituted aromatic ring; a hydrogen atom on the aromatic ring may be substituted with either a fluorine atom, a chlorine atom, a hydroxyl group, an amino group, a nitro group, a cyano group, a hydroxycarbonyl group, a $C_1\text{-}C_6$ straight, branched or cyclic alkyl group (whose hydrogen atom may be substituted with a hydroxyl group or a fluorine atom), a $C_1\text{-}C_6$ straight, branched or cyclic alkoxy group, a $C_1\text{-}C_6$ straight, branched or cyclic alkoxycarbonyl group or a substituted or unsubstituted monovalent aromatic ring group; and $Y^2$ each independently represent a single bond, or a divalent group made up of either one, or two or more of the same kind or different kinds, selected from the group consisting of $CH_2$, $CH_2CH_2$, $CH_2CH_2CH_2$, O, S, $C(CH_3)_2$, $C(CF_3)_2$, $SO_2$, CO, NH, COO (ester) and CONH.

[4] The polymer according to any one of Inventive Aspects 1 to 3, wherein the divalent organic group Q is either one of divalent organic groups of the following formulas:

[Chem. 4]

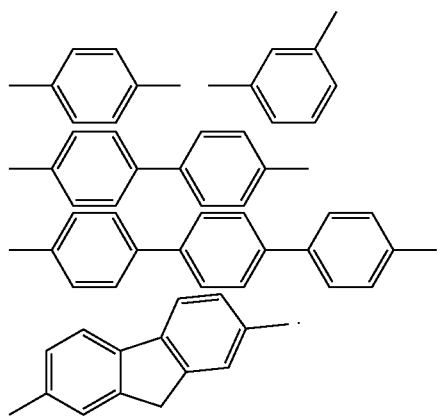

[5] The polymer according to any one of Inventive Aspects 1 to 4, wherein the polymer is of the general formula (7) obtained by polycondensation of the fluorinated dicarboxylic acid derivative or acid anhydride with a diamine of the general formula (3) as the polyfunctional compound:

[Chem. 5]

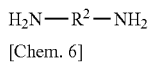
(3)

[Chem. 6]

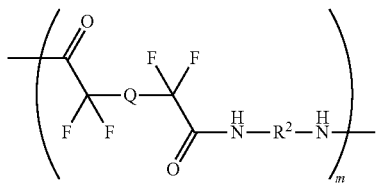
(7)

where Q has the same meaning as in the general formula (M-1); $R^2$ represents a divalent organic group having at least one kind selected from an alicyclic ring, an aromatic ring and a heterocyclic ring and may contain a fluorine atom, a chlorine atom, an oxygen atom, a sulfur atom or a nitrogen atom; a part of hydrogen atoms of $R^2$ may be substituted with a fluorine atom, a chlorine atom, an alkyl group, a fluoroalkyl group, a carboxyl group, a hydroxyl group or a cyano group; a part of carbon atoms of $R^2$ may be replaced by an oxygen atom, a sulfur atom, a nitrogen atom, a carbonyl group or a sulfonyl group; and m represents a positive integer.

[6] The polymer according to any one of Inventive Aspects 1 to 4, wherein the polymer is of the general formula (8) obtained by polycondensation of the fluorinated dicarboxylic acid derivative or acid anhydride with a diaminodiol of the general formula (4) as the polyfunctional compound:

[Chem. 7]

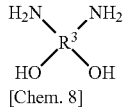
(4)

[Chem. 8]

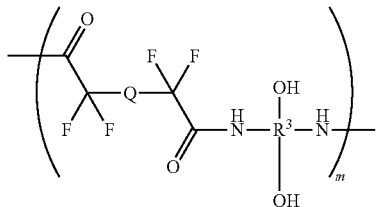
(8)

where Q has the same meaning as in the general formula (M-1); $R^3$ represents a quaternary organic group having at least one kind selected from an alicyclic ring, an aromatic ring and a heterocyclic ring and may contain a fluorine atom, a chlorine atom, an oxygen atom, a sulfur atom or a nitrogen atom; a part of hydrogen atoms of $R^3$ may be substituted with a fluorine atom, a chlorine atom, an alkyl group, a fluoroalkyl group, a carboxyl group, a hydroxyl group or a cyano group; a part of carbon atoms of $R^3$ may be replaced by an oxygen atom, a sulfur atom, a nitrogen atom, a carbonyl group or a sulfonyl group; and m represents a positive integer.

[7] A polymer of the following general formula (9) obtained by dehydration ring closure of the polymer of the general formula (8) according to Inventive Aspect 6:

[Chem. 9]

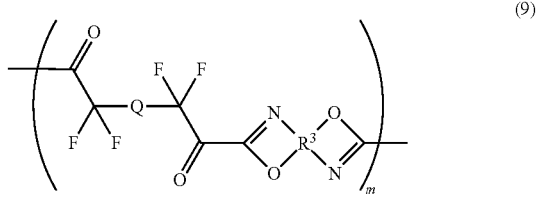
(9)

where Q has the same meaning as in the general formula (M-1); and $R^3$ has the same meaning as in the general formula (4).

[8] The polymer according to any one of Inventive Aspects 1 to 4, wherein the polymer is of the general formula (10) obtained by polycondensation of the fluorinated dicarboxylic acid derivative or acid anhydride with a hexaisopropanol-substituted diaminodiol of the general formula (5) as the polyfunctional compound:

[Chem. 10]

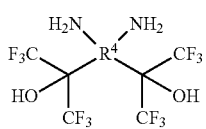
(5)

[Chem. 11]

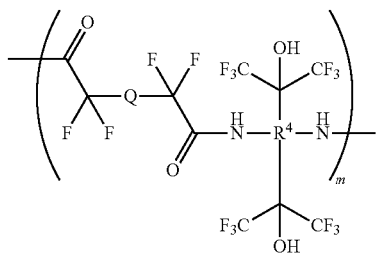
(10)

where Q has the same meaning as in the general formula (M-1); $R^4$ represents a quaternary organic group having at least one kind selected from an alicyclic ring, an aromatic ring and a heterocyclic ring and may contain a fluorine atom, a chlorine atom, an oxygen atom, a sulfur atom or a nitrogen atom; a part of hydrogen atoms of $R^4$ may be substituted with a fluorine atom, a chlorine atom, an alkyl group, a fluoroalkyl group, a carboxyl group, a hydroxyl group or a cyano group; a part of carbon atoms of $R^4$ may be replaced by an oxygen atom, a sulfur atom, a nitrogen atom, a carbonyl group or a sulfonyl group; and m represents a positive integer.

[9] A polymer of the following general formula (11) obtained by dehydration ring closure of the polymer of the general formula (10) according to Inventive Aspect 8:

[Chem. 12]

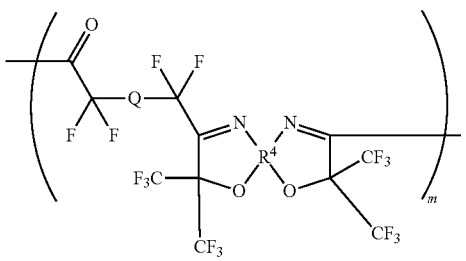
(11)

where Q has the same meaning as in the general formula (M-1); and $R^4$ has the same meaning as in the general formula (5).

The polymer according to any one of Inventive Aspects 1 to 4, wherein the polymer is of the general formula (6) obtained by polycondensation of the fluorinated dicarboxylic acid derivative or acid anhydride with a diol of the general formula (2) as the polyfunctional compound:

[Chem. 13]

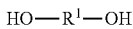
HO—$R^1$—OH (2)

[Chem. 14]

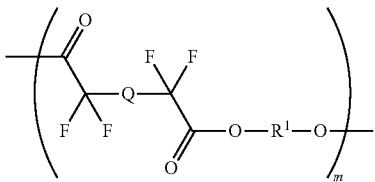
(6)

where Q has the same meaning as in the general formula (M-1); $R^1$ represents a divalent organic group having at least one kind selected from an alicyclic ring, an aromatic ring and a heterocyclic ring and may contain a fluorine atom, a chlorine atom, an oxygen atom, a sulfur atom or a nitrogen atom; a part of hydrogen atoms of $R^1$ may be substituted with a fluorine atom, a chlorine atom, an alkyl group, a fluoroalkyl group, a carboxyl group, a hydroxyl group or a cyano group; a part of carbon atoms of $R^1$ may be replaced by an oxygen atom, a sulfur atom, a nitrogen atom, a carbonyl group or a sulfonyl group; and m represents a positive integer.

[11] A fluorinated dicarboxylic acid derivative of the general formula (M-2):

[Chem. 15]

DOCF$_2$C-Q-CF$_2$COD' (M-2)

where Q represents a divalent organic group having a substituted or unsubstituted aromatic ring; a hydrogen atom on the aromatic ring may be substituted with either a fluorine atom, a chlorine atom, a hydroxyl group, an amino group, a nitro group, a cyano group, a hydroxycarbonyl group, a $C_1$-$C_6$ straight, branched or cyclic alkyl group (whose hydrogen atom may be substituted with a hydroxyl group or a fluorine atom), a $C_1$-$C_6$ straight, branched or cyclic alkoxy group, a $C_1$-$C_6$ straight, branched or cyclic alkoxycarbonyl group or a substituted or unsubstituted monovalent aromatic ring group; two difluoromethylene groups are not bonded to adjacent carbon atoms of the aromatic ring; D and D' each independently represent a hydroxyl group, a fluorine atom, a chlorine atom, a bromine atom, an iodine atom, a $C_1$-$C_6$ straight, branched or cyclic alkoxy group or a $C_6$-$C_{10}$ substituted or unsubstituted aryloxy group and may form an active ester moiety with a CO group (carbonyl group) in the formula.

The fluorinated polymer such as polyester or polyamide of the present invention meets the requirement for low-temperature curability, in particular, the requirement to obtain a sufficient polymerization degree even by heating at 250° C. or lower as strongly demanded in response to the decrease in the thermal resistance of semiconductor chips. The resulting film of the fluorinated polymer exhibits good flexibility and excellent electrical characteristics (low dielectric constant) and can be used as a protection film. The heterocyclic compound obtained by ring closure of the polyester or polyamide of the present invention also combines a low dielectric constant with good flexibility and can be used as a protection film. Further, the fluorinated dicarboxylic acid and derivative thereof is significantly useful for the production of such a fluorinated polymer.

BEST MODES FOR CARRYING OUT THE INVENTION

Hereinafter, embodiments of the present invention will be described below. It should be understood that: the present invention is not limited to the following embodiments; and various variations and modifications can be made to the following embodiments, without departing from the scope of the present invention, based on the common knowledge of any skilled in the art and are intended to be included within the scope of the present invention.

[Fluorinated Dicarboxylic Acid Derivative]

In the present specification, the term "fluorinated dicarboxylic acid derivative" may include a fluorinated dicarboxylic acid.

The fluorinated dicarboxylic acid derivative of the present invention is represented by the following general formula (M-1) or (M-2).

[Chem. 16]

AOCF$_2$C-Q-CF$_2$COA' (M-1)

[Chem. 17]

DOCF$_2$C-Q-CF$_2$COD' (M-2)

Herein, CF$_2$COA and CF$_2$COA' may be bonded to the same carbon atom or different carbon atoms of the aromatic ring; and CF$_2$COD and CF$_2$COD' may be bonded to the same carbon atom or different carbon atoms of the aromatic ring. However, CF$_2$COD and CF$_2$COD' are not bonded to adjacent carbon atoms of the same aromatic ring as the bonding of two carboxylic moieties to adjacent carbon atoms of the aromatic ring leads to poor polymerizability of the fluorinated dicarboxylic acid derivative and makes it difficult to obtain the polymer from the fluorinated dicarboxylic acid derivative.

In the above formulas, Q represents a divalent organic group having a substituted or unsubstituted aromatic ring. This divalent organic group is an organic group obtained by elimination of two hydrogen atoms from any compound having one or two or more aromatic rings. The aromatic ring is a monocyclic or polycyclic ring of 4 to 20 carbon atoms. Further, Y represents, as a linking group between the aromatic rings, a single bond, or a divalent group made up of either one, or two or more of the same kind or different kinds, selected from the group consisting of CH$_2$, CH$_2$CH$_2$, CH$_2$CH$_2$CH$_2$, O, S, C(CH$_3$)$_2$, C(CF$_3$)$_2$, SO$_2$, CO, NH, COO (ester) and CONH. The aromatic rings may be bonded by a plurality of these linking groups.

Examples of the aromatic ring are a benzene ring, a naphthalene ring, an anthracene ring, a tetracene ring, a pentacene ring, a phenanthrene ring, a chrysene ring, a triphenylene ring, a tetraphene ring, a pyrene ring, a picene ring, a pentaphene ring, a perylene ring, a pyrrole ring, a furan ring, a thiophene ring, an imidazole ring, an oxazole ring, a thiazole ring, a pyrazole ring, an isooxazole ring, an isothiazole ring, a pyridine ring, a pyrimidine ring, a pyrazine ring and a pyridazine ring. Among others, a benzene ring, a naphthalene ring and a pyridine ring are preferred.

A hydrogen atom on the aromatic ring may be substituted with either a fluorine atom, a chlorine atom, a hydroxyl group, an amino group, a nitro group, a cyano group, a hydroxylcarbonyl group, a $C_1$-$C_6$ straight, branched or cyclic alkyl group (whose hydrogen atom may be substituted with a hydroxyl group or a fluorine atom), a $C_1$-$C_6$ straight, branched or cyclic alkoxy group or a $C_1$-$C_6$ straight, branched or cyclic alkoxycarbonyl group.

Examples of the $C_1$-$C_6$ straight, branched or cyclic alkyl group are methyl, ethyl, n-propyl, n-butyl, n-pentyl, n-hexyl, isopropyl, isobutyl, sec-butyl, tert-butyl, cyclopentyl and cyclohexyl.

Examples of the hydroxyl-substituted alkyl group are hydroxymethyl, 1-hydroxyethyl, 2-hydroxyethyl, 3-hydroxy-n-propyl, 4-hydroxy-n-butyl, 5-hydroxy-n-pentyl, 6-hydroxy-n-hexyl, hydroxycyclopentyl and hydroxycyclohexyl.

Examples of the fluorine-substituted alkyl group are monofluoromethyl, difluoromethyl, trifluoromethyl, pentafluoroethyl, 2,2,2-trifluoroethyl, pentafluoroethyl, heptafluoro-n-propyl, heptafluoroisopropyl and nonafluoro-n-butyl.

Examples of the hydroxyl- and fluorine-substituted alkyl group are difluorohydroxymethyl, 2-hydroxy-1,1,2,2-tetrafluoroethyl, 1,1-difluoro-2-hydroxyethyl and 2,2,2-trifluoro-1-hydroxy-1-(trifluoromethyl)ethyl.

Examples of the $C_1$-$C_6$ straight, branched or cyclic alkoxy group are methoxy, ethoxy, n-propoxy, isopropoxy, n-butoxy, isobutoxy, sec-butoxy, tert-butoxy, n-pentoxy, isopentoxy, sec-pentoxy, tert-pentoxy, n-hexoxy, isohexoxy, cyclopentoxy and cyclohexoxy.

Examples of the $C_1$-$C_6$ straight, branched or cyclic alkoxycarbonyl group are methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, n-pentoxycarbonyl, isopentoxycarbonyl, sec-pentoxycarbonyl, tert-pentoxycarbonyl, n-hexoxycarbonyl, isohexoxycarbonyl, cyclopentoxycarbonyl and cyclohexoxycarbonyl.

One example of the divalent organic group Q having the substituted or unsubstituted aromatic ring is a divalent organic group of the following general formula (a) where the aromatic ring is represented by $Ar^1$ and the linking group Y is represented by $Y^1$.

[Chem. 18]

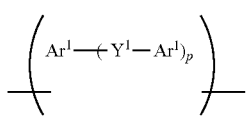

(a)

In the above formula, $Ar^1$ each independently represent the substituted or unsubstituted aromatic ring. A hydrogen atom on the aromatic ring may be substituted with either a fluorine atom, a chlorine atom, a hydroxyl group, an amino group, a nitro group, a cyano group, a hydroxylcarbonyl group, a $C_1$-$C_6$ straight, branched or cyclic alkyl group (whose hydrogen atom may be substituted with a hydroxyl group or a fluorine atom), a $C_1$-$C_6$ straight, branched or cyclic alkoxy group, a $C_1$-$C_6$ straight, branched or cyclic alkoxycarbonyl group or a substituted or unsubstituted monovalent aromatic ring group. Further, $Y^1$ represents, as the linking group, a single bond, or a divalent group made up of either one, or two or more of the same kind or different kinds, selected from the group consisting of $CH_2$, $CH_2CH_2$, $CH_2CH_2CH_2$, O, S, $C(CH_3)_2$, $C(CF_3)_2$, $SO_2$, CO, NH, COO (ester) and CONH. Herein, p represents an integer of 0 to 3. Two free sites of the divalent organic group are bonded to the same carbon atom or different carbon atoms of the aromatic ring in the formula.

The following aromatic ring structures are specific examples of the divalent organic group of the general formula (a) in the case where p is 0. In the present specification, the dotted lines represent the substitution positions of $CF_2COA$ and $CF_2COA'$ or the substitution positions of $CF_2COD$ and $CF_2COD'$. It is noted that, in the case of the general formula (M-2), two difluoromethylene groups are not bonded to adjacent carbon atoms of the aromatic ring, i.e., the dotted lines do not start from adjacent carbon atoms of the aromatic ring.

[Chem. 19]

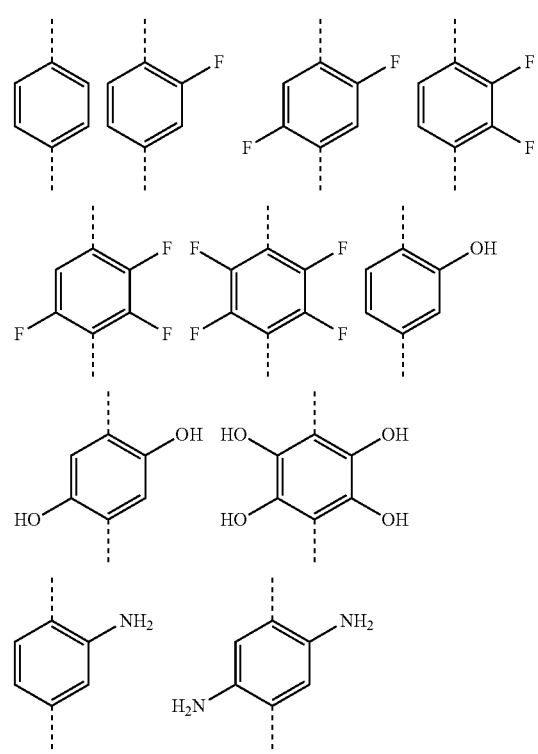

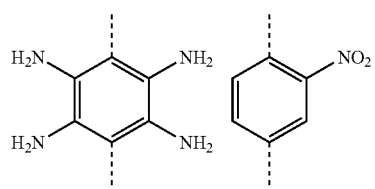

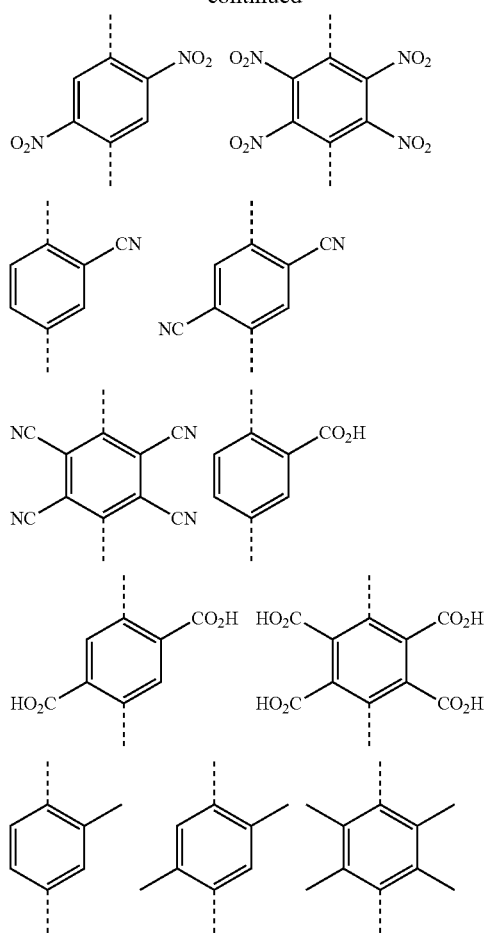
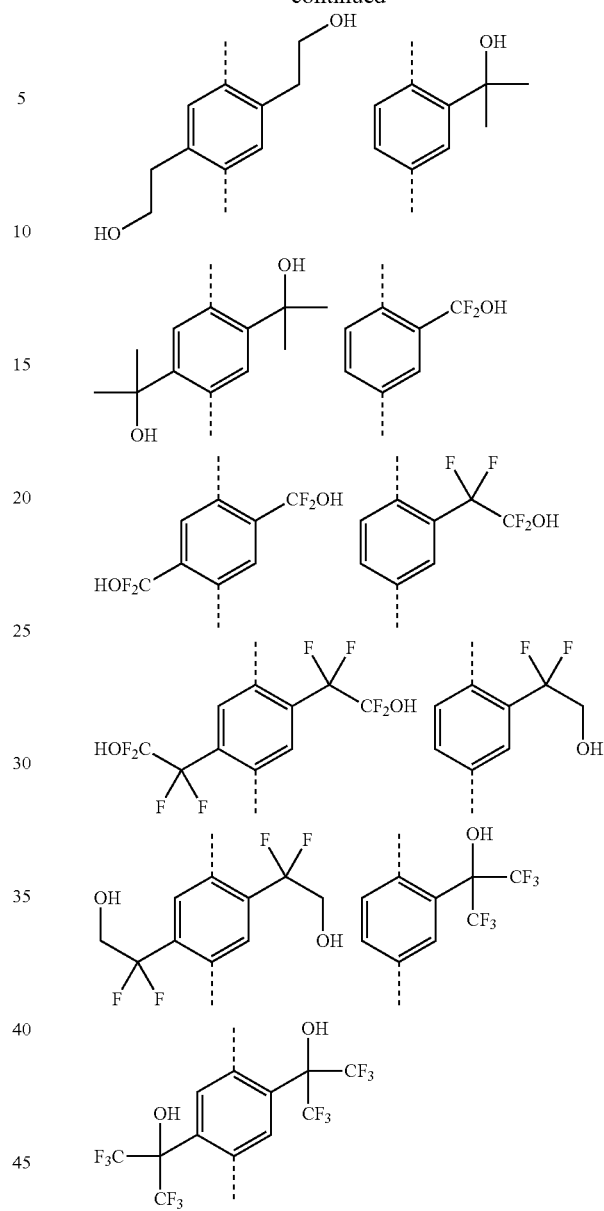
[Chem. 20]
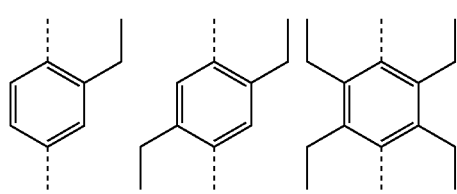
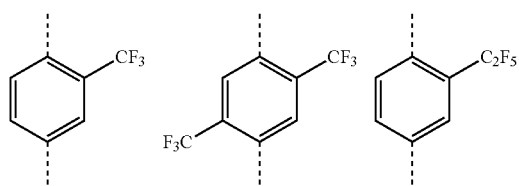
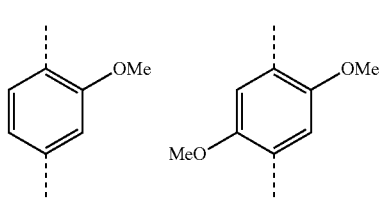
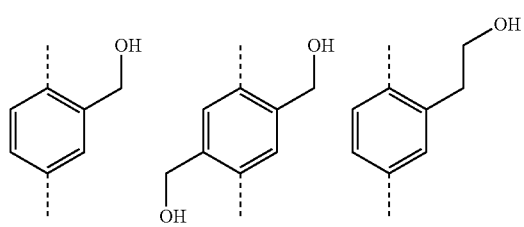
[Chem. 21]
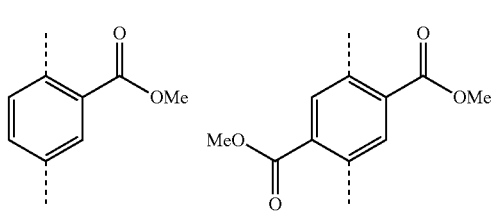

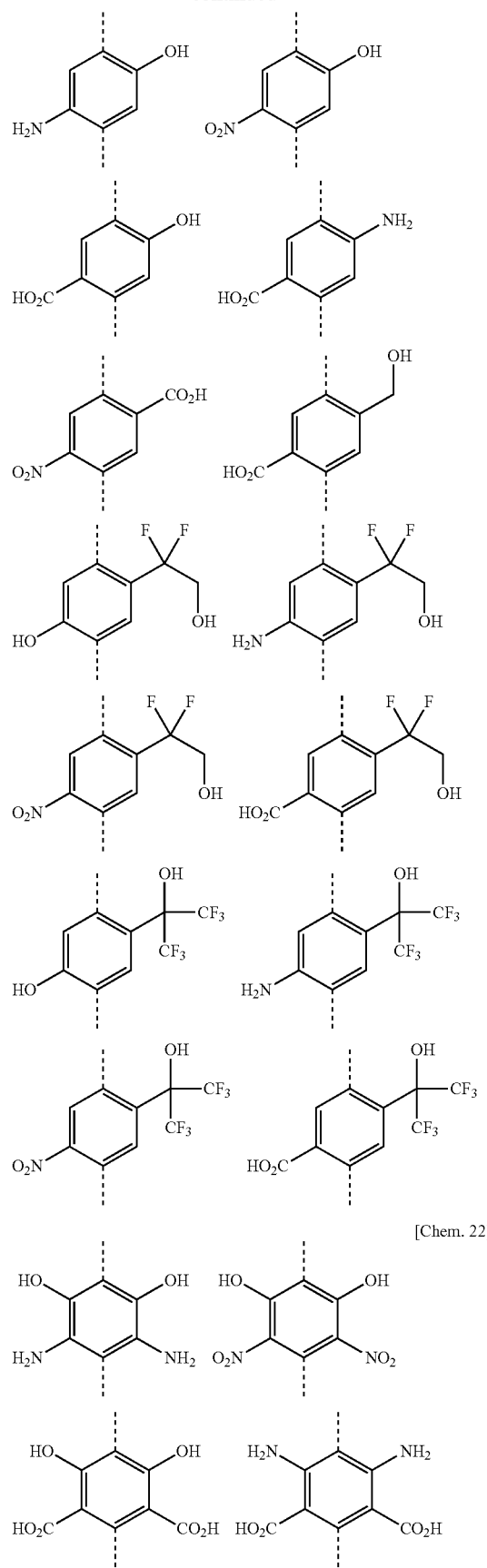
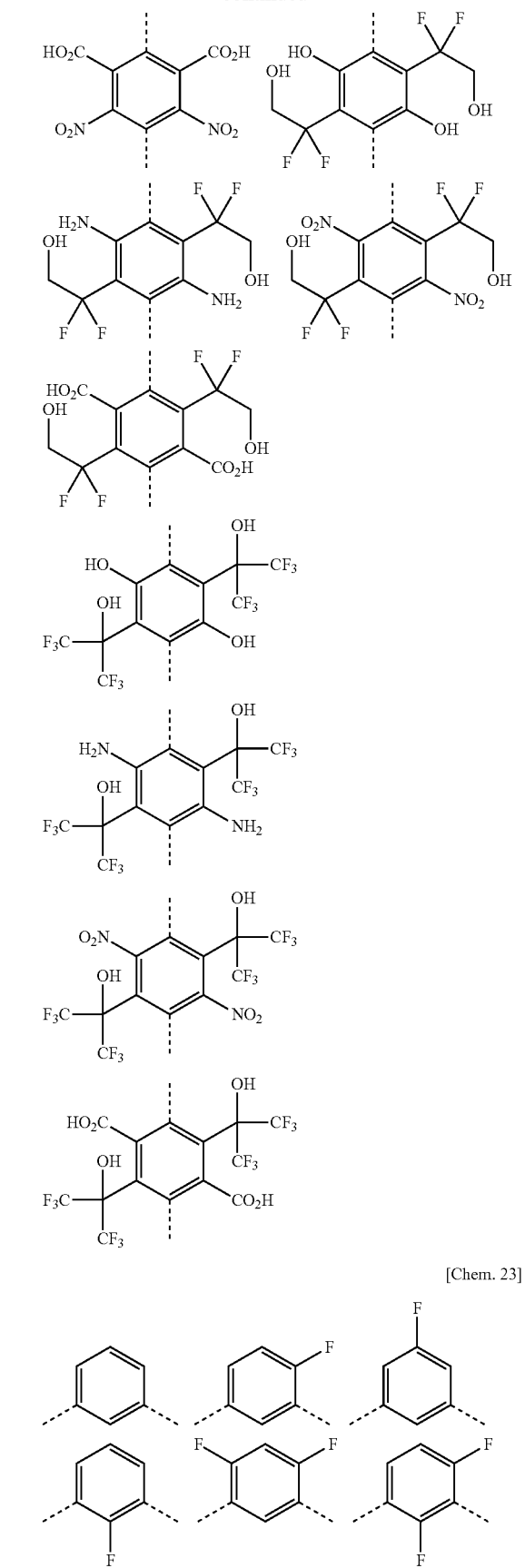

-continued
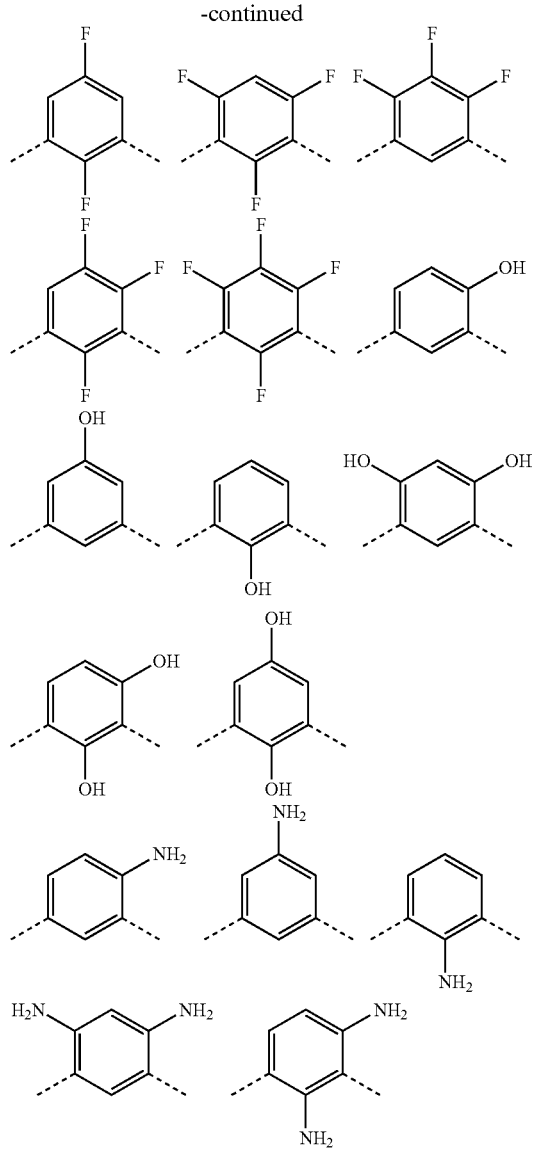
[Chem. 24]
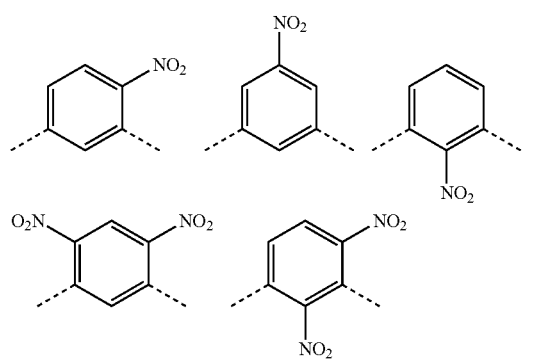
-continued
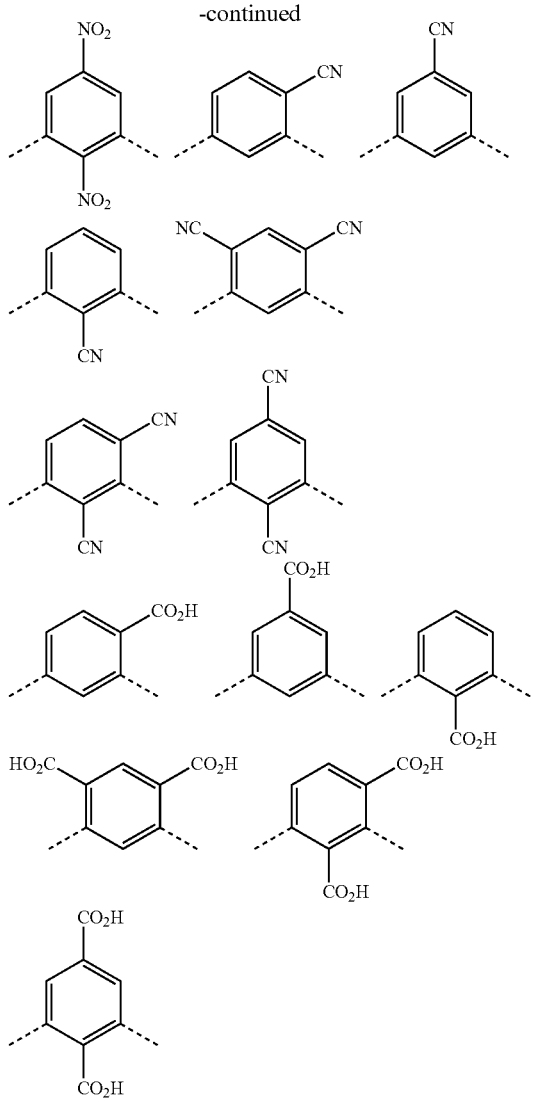
[Chem. 25]
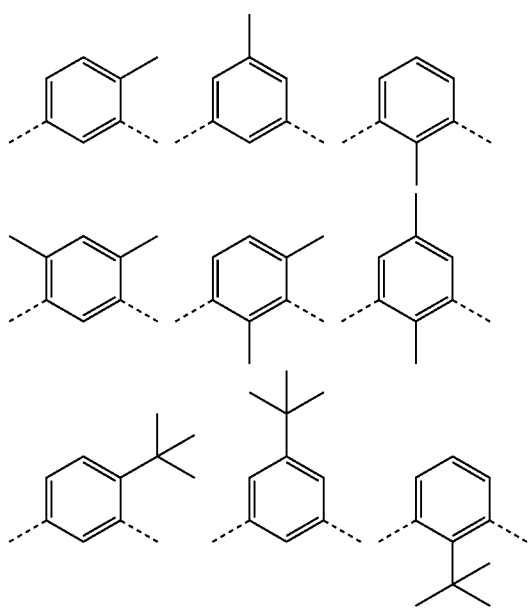

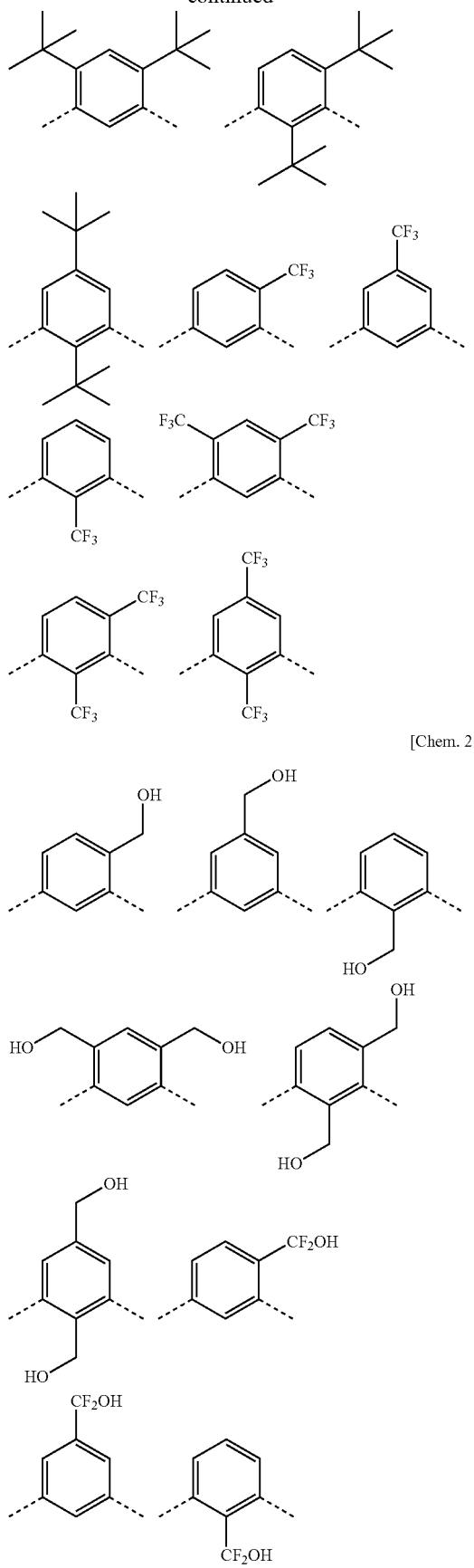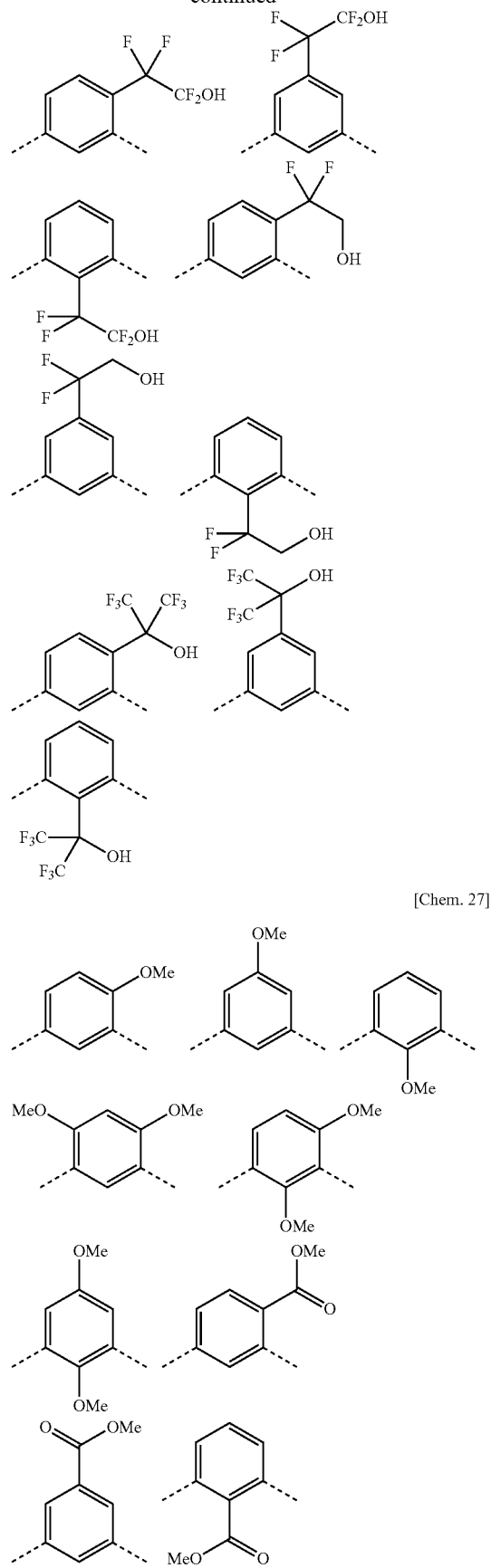

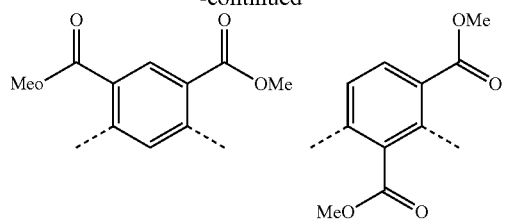
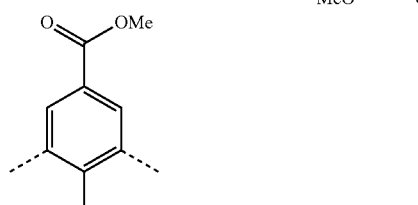
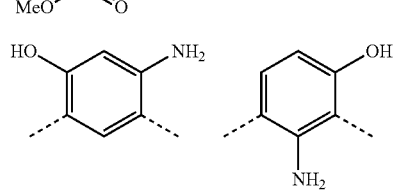
[Chem. 28]
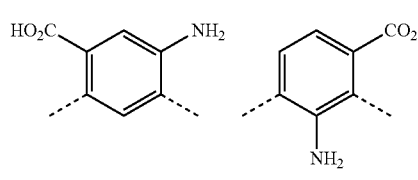
[Chem. 29]
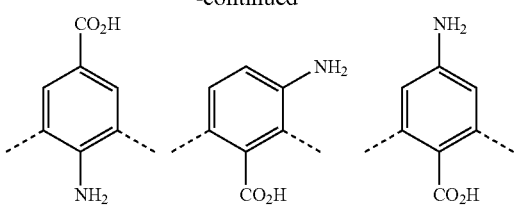
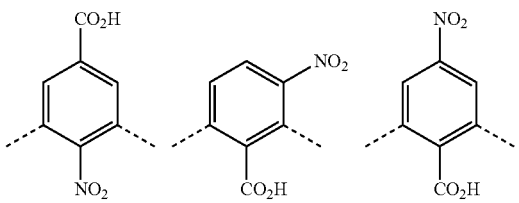
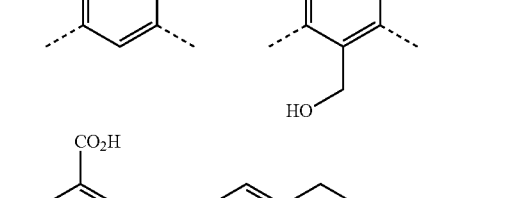
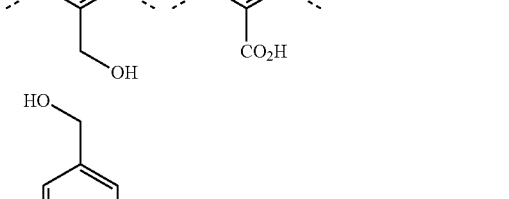
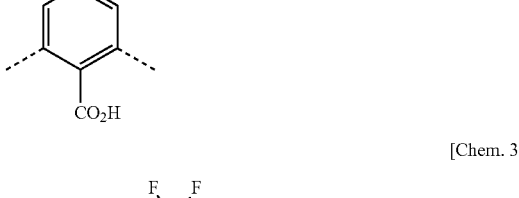
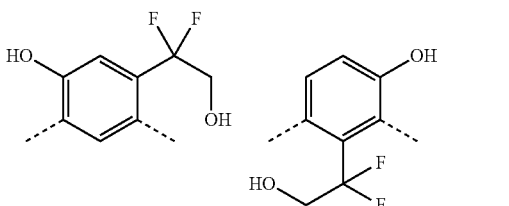
[Chem. 30]
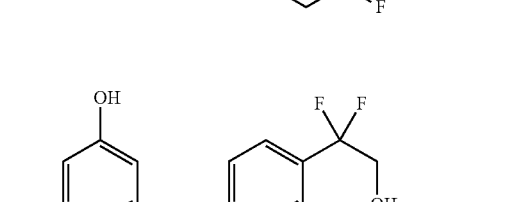
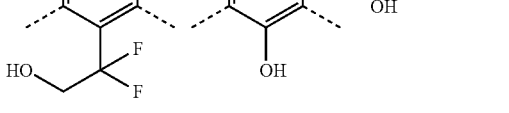

-continued
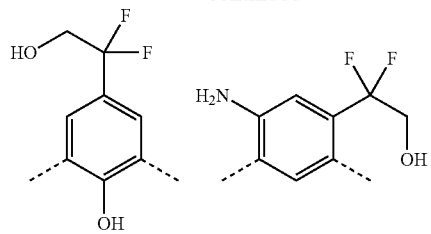
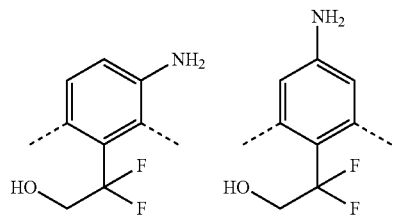
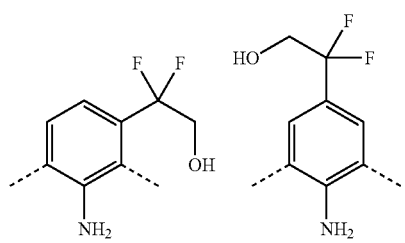
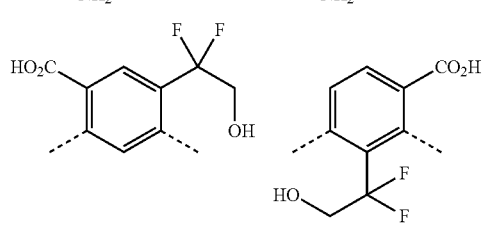
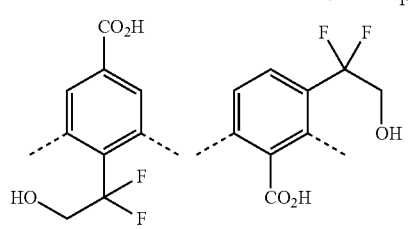
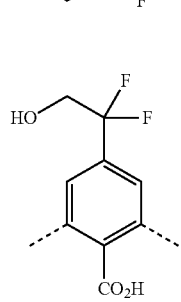
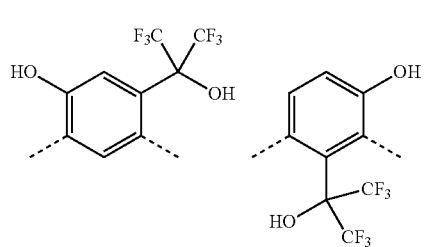
-continued
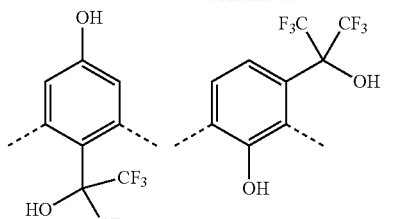
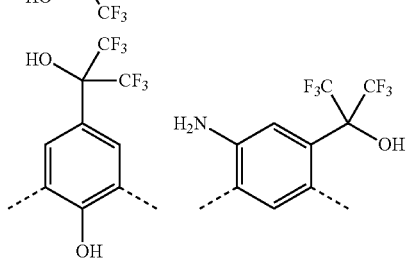
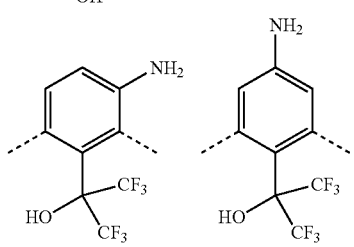
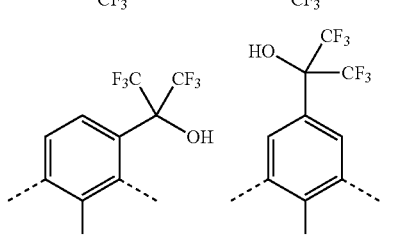
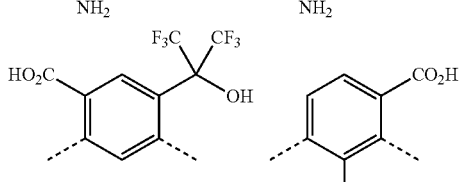
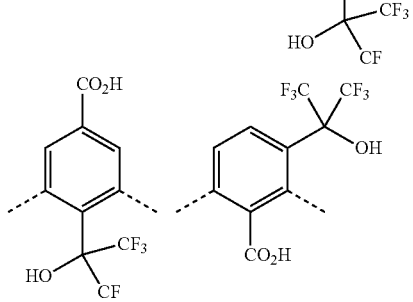
[Chem. 31]
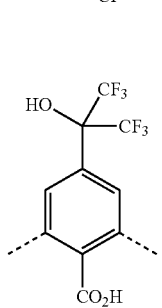

[Chem. 32]
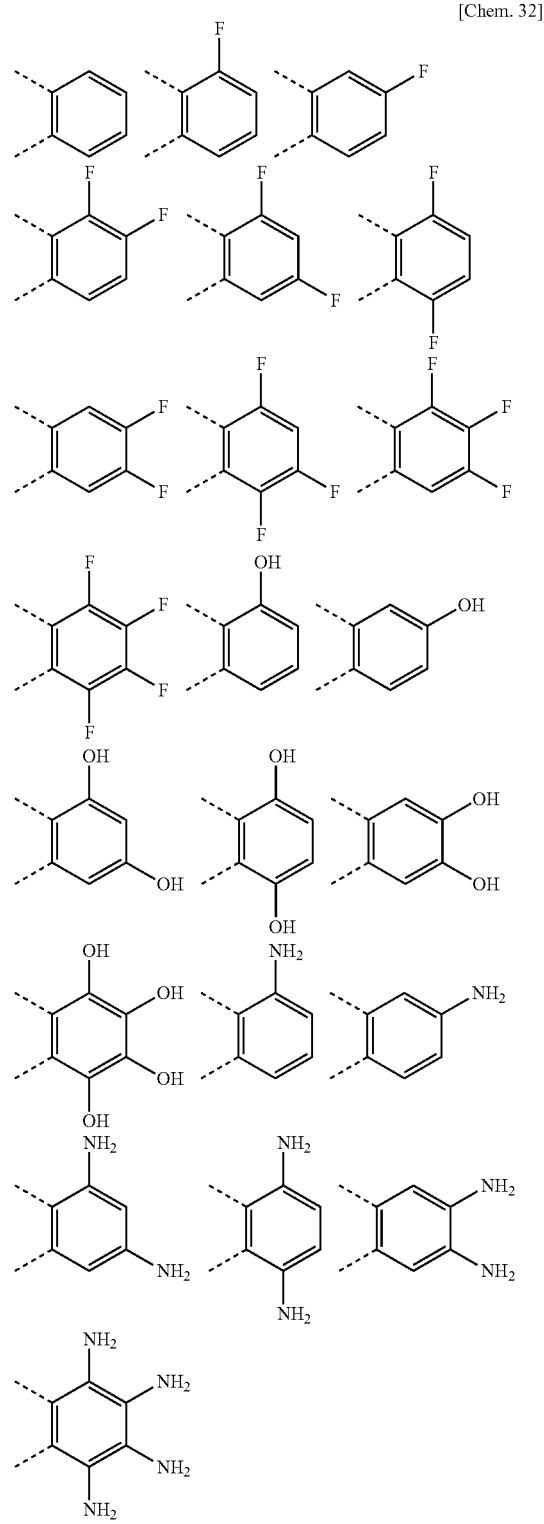
[Chem. 33]
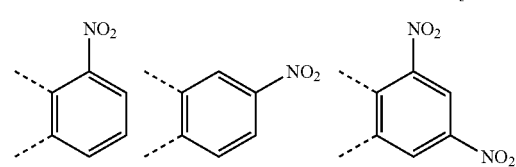
[Chem. 34]
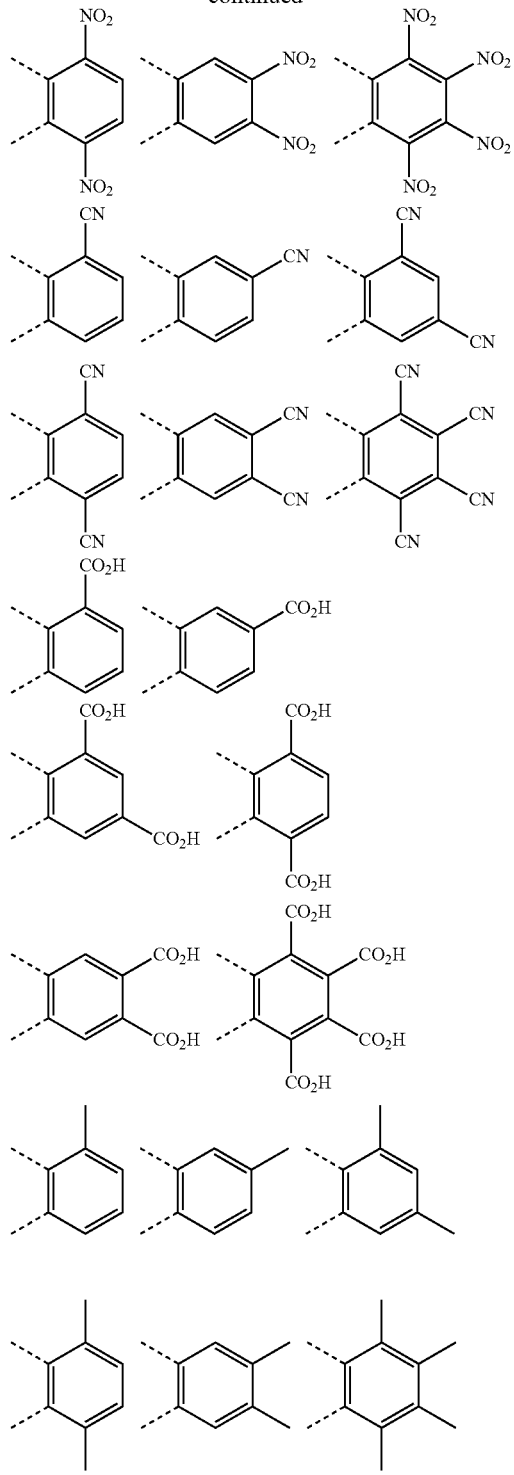
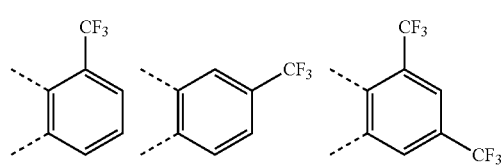

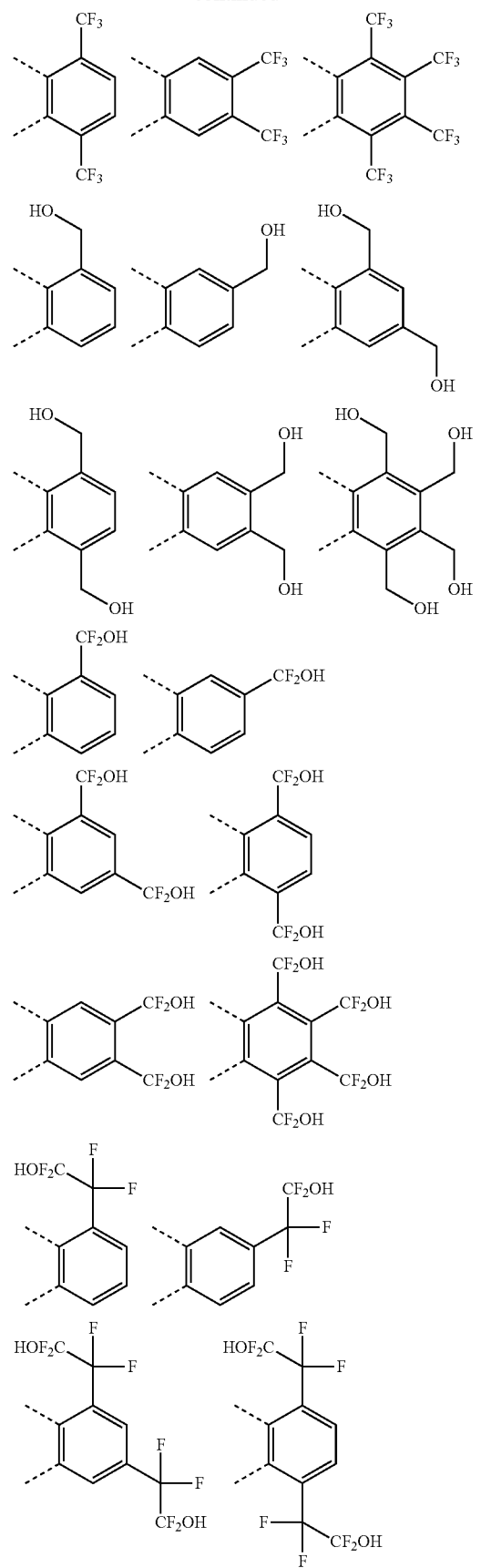
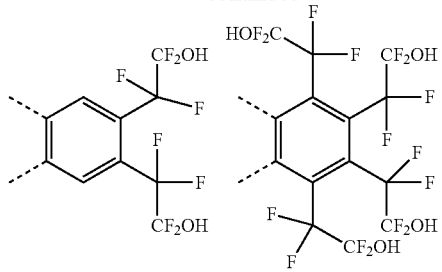
[Chem. 35]
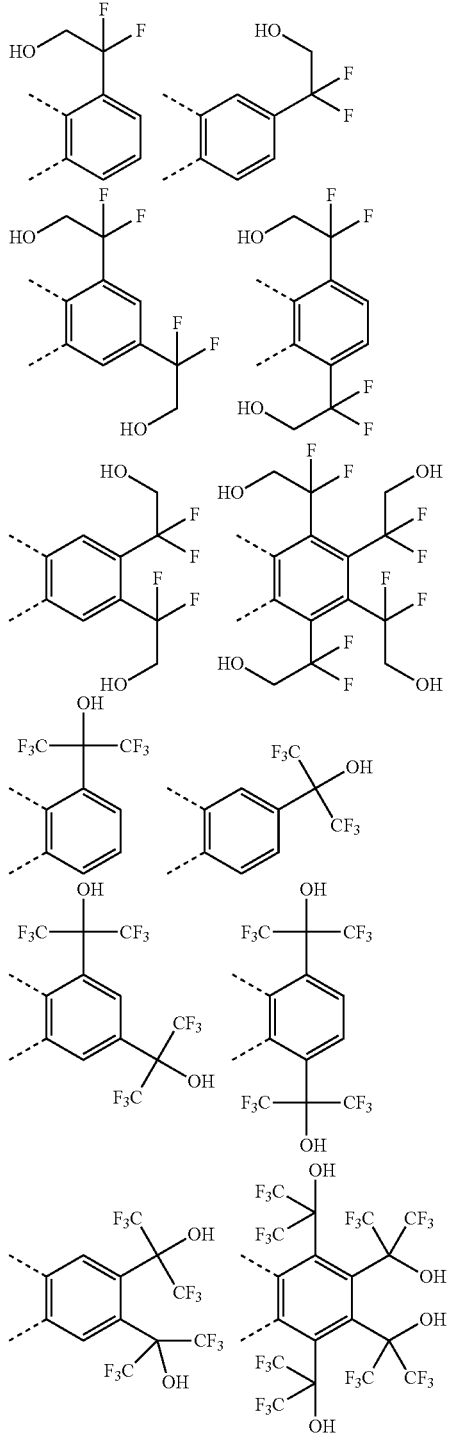

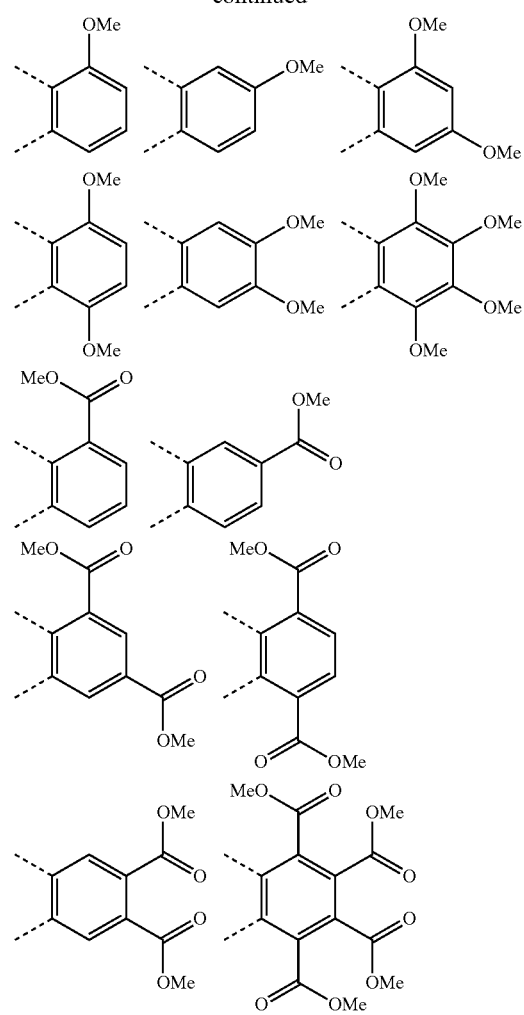
[Chem. 36]
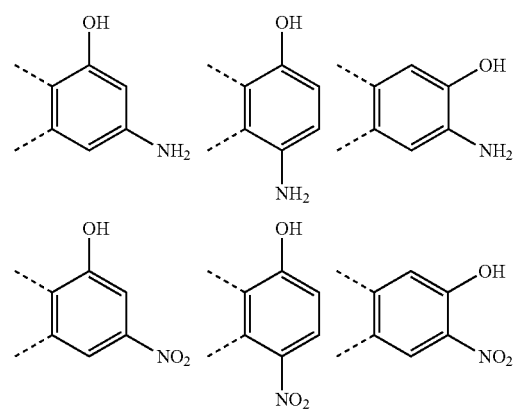
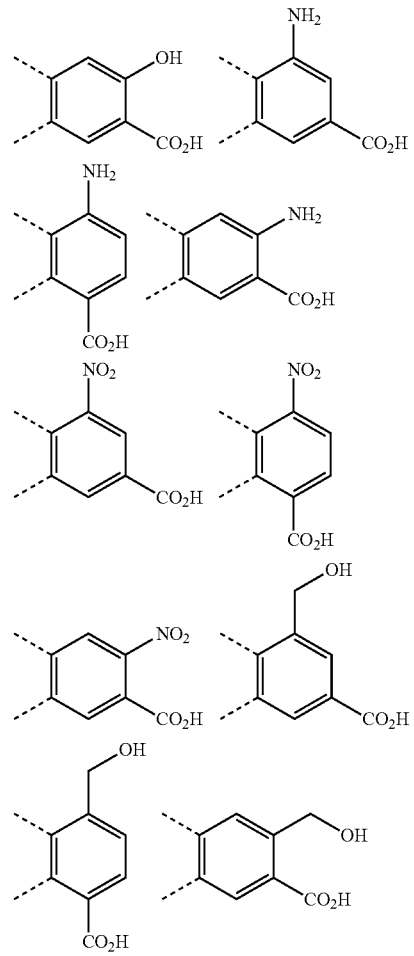
[Chem. 37]
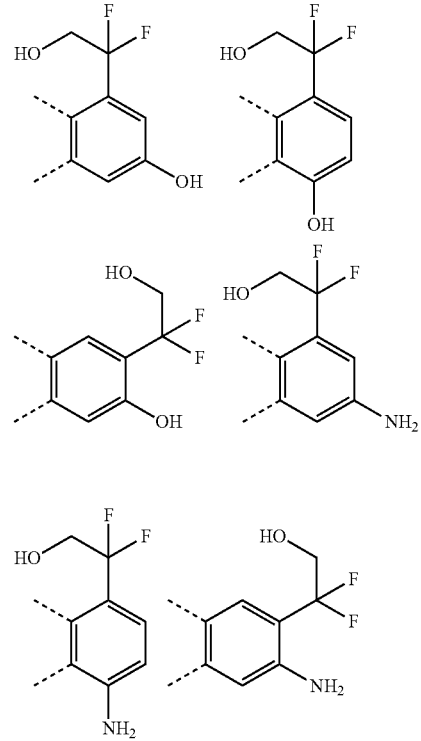

29
-continued
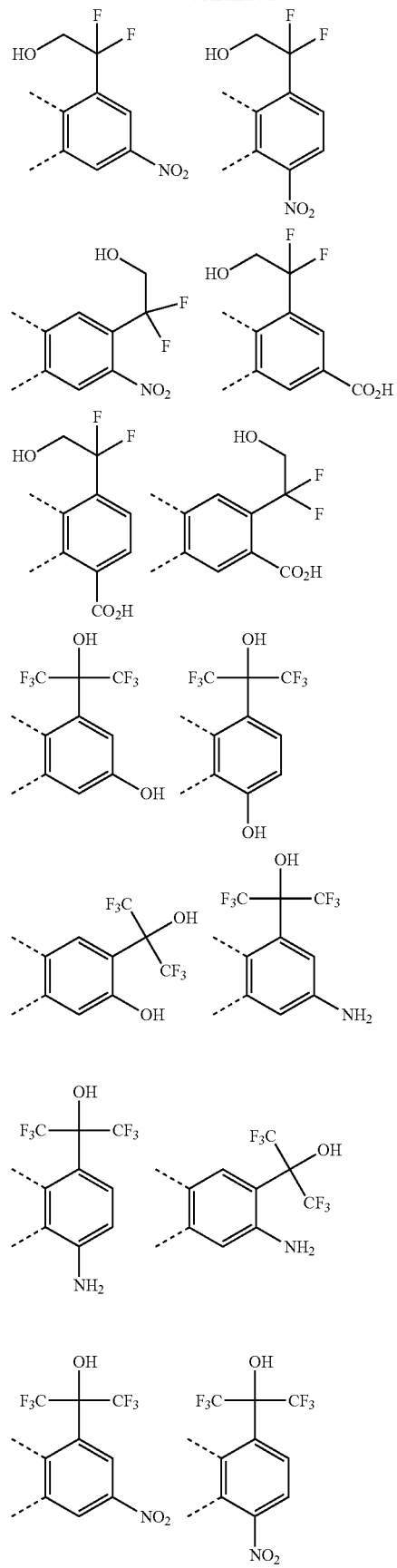
30
-continued
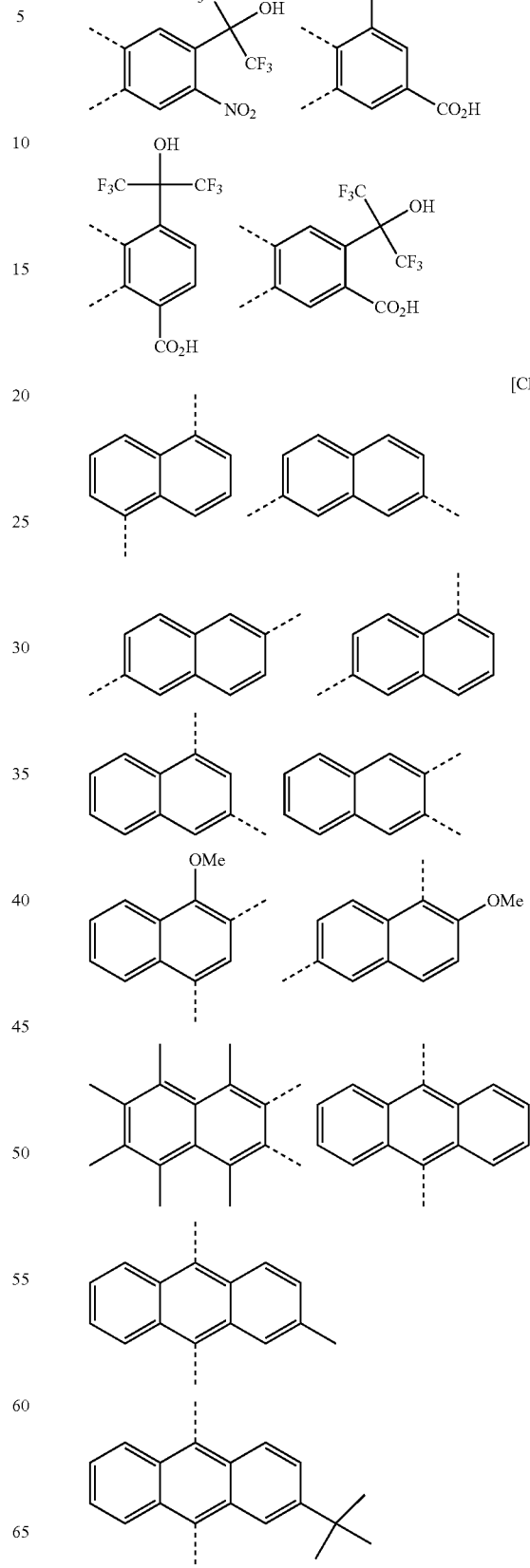
[Chem. 38]

-continued

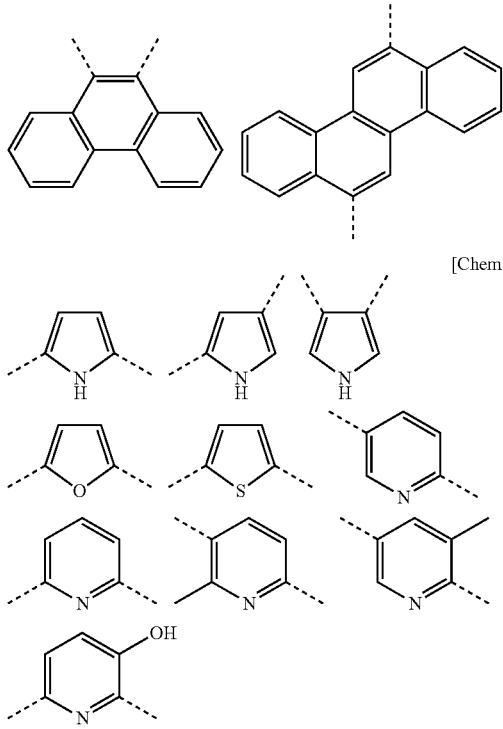

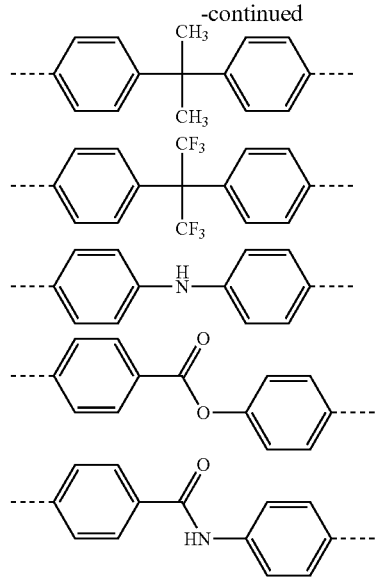

In the substituted or unsubstituted aromatic ring structure Q, the amino group may be a protected amino group. As a protection group for the amino group, there can be used tert-butoxycarbonyl, benzyloxycarbonyl, 9-fluorenylmethyloxycarbonyl, 2,2,2-trichloroethoxycarbonyl, allyloxycarbonyl, phthaloyl, p-toluenesulfonyl, 2-nitrobenzenesulfonyl or the like.

The following are specific examples of the divalent organic group of the general formula (a) in the case where p is 1.

[Chem. 40]

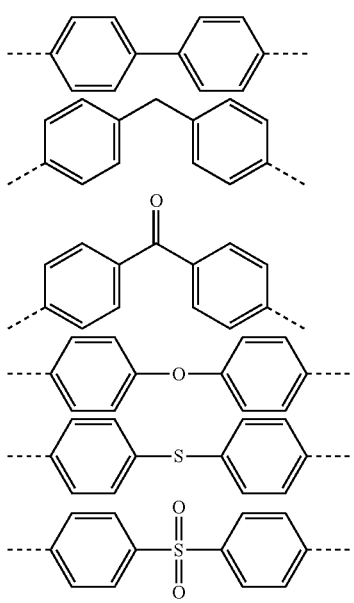

The following are specific examples of the divalent organic group of the general formula (a) in the case where p is 2.

[Chem. 41]

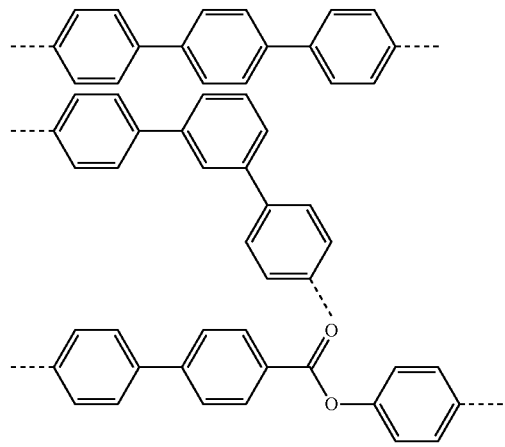

Another example of the divalent organic group Q having the substituted or unsubstituted aromatic ring is a divalent organic group of the following general formula (b) where the aromatic ring is represented by $Ar^2$ and the linking group Y is represented by $Y^2$.

[Chem. 42]

(b)

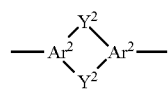

In the above formula, $Ar^2$ each independently represent the substituted or unsubstituted aromatic ring. A hydrogen atom on the aromatic ring may be substituted with either a fluorine atom, a chlorine atom, a hydroxyl group, an amino group, a nitro group, a cyano group, a hydroxycarbonyl group, a $C_1$-$C_6$ straight, branched or cyclic alkyl group (whose hydrogen atom may be substituted with a hydroxyl group or a fluorine atom), a $C_1$-$C_6$ straight, branched or cyclic alkoxy group, a $C_1$-$C_6$ straight, branched or cyclic alkoxycarbonyl group or a substituted or unsubstituted monovalent aromatic ring group. Further, $Y^2$ each independently represent, as the linking group, a single bond, or a divalent group made up of either one, or two or more of the same kind or different kinds, selected from the group consisting of $CH_2$, $CH_2CH_2$, $CH_2CH_2CH_2$, O, S, $C(CH_3)_2$, $C(CF_3)_2$, $SO_2$, CO, NH, COO (ester) and CONH.

The following are specific examples of the divalent organic group of the following general formula (b).

[Chem. 43]

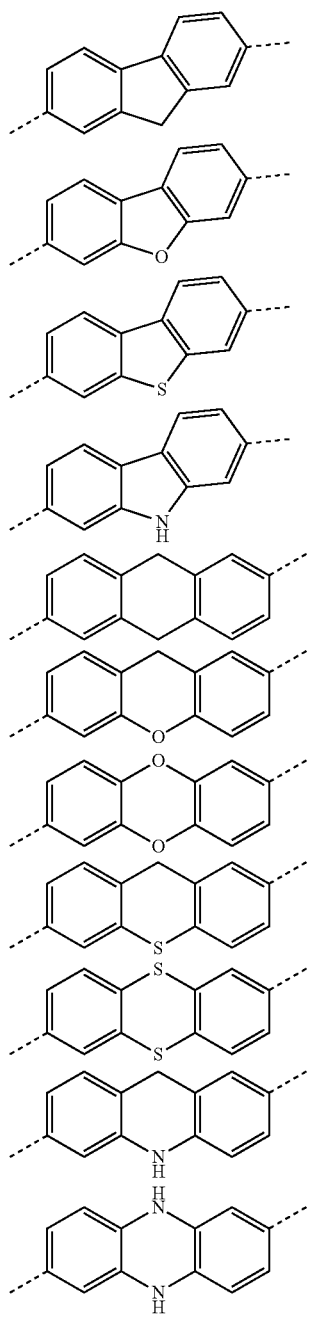

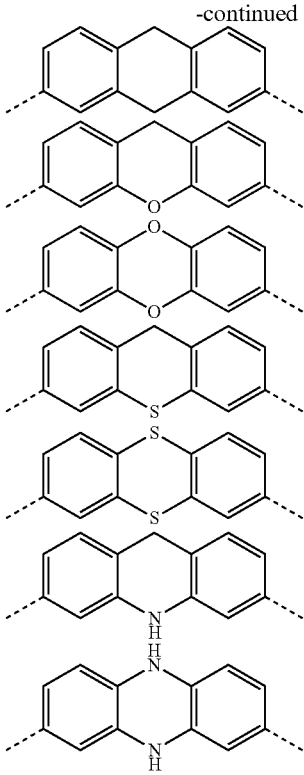

The divalent organic aromatic ring structure Q is not however limited to the above examples. Among others, the following are particularly preferred.

[Chem. 44]

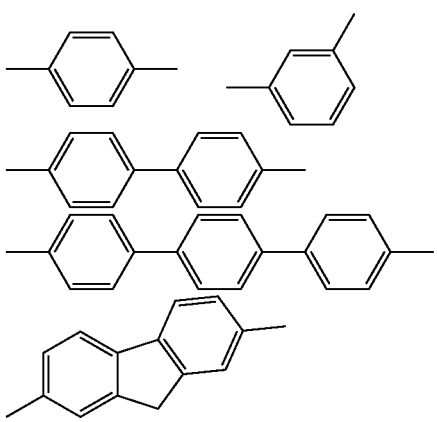

In the general formulas (M-1) and (M-2), A and A' each independently and D and D' each independently represent a hydroxyl group, a fluorine atom, a chlorine atom, a bromine atom, an iodine atom, a $C_1$-$C_6$ straight, branched or cyclic alkoxy group or a $C_6$-$C_{10}$ substituted or unsubstituted aryloxy group and may form an active ester moiety with a CO group (carbonyl group) in the formula.

Examples of the $C_1$-$C_6$ straight, branched or cyclic alkoxy group are methoxy, ethoxy, n-propoxy, isopropoxy, n-butoxy, isobutoxy, sec-butoxy, tert-butoxy, n-pentoxy, isopentoxy, sec-pentoxy, tert-pentoxy, n-hexoxy, isohexoxy, cyclopentoxy and cyclohexoxy. Among others, methoxy and ethoxy are preferred.

Examples of the $C_6$-$C_{10}$ substituted or unsubstituted aryloxy group are phenoxy, o-tolyloxy, m-tolyloxy, p-tolyloxy, p-hydroxyphenoxy, p-nitrophenoxy, polychlorophenoxy, 1-naphthoxy, benzyloxy and pyridyloxy. Among others, p-nirtophenoxy is preferred.

As A and A' and as D and D', there can be used a succinimidoxy group, an o-phthalimidoxy group etc. that can form an active ester moiety with a CO group (carbonyl group).

Among others, a hydroxyl group, a chlorine atom, a succinimidoxy group and an ethoxy group are particularly preferred as A and A' and as D and D'.

Examples of the acid anhydride of the fluorinated dicarboxylic acid of the general formula (M-1) (where both of A and A' are hydroxyl) are those derived from the fluorinated dicarboxylic acid in which $AOCF_2C$ and $A'OCF_2C$ are bonded to adjacent carbon atoms of the aromatic ring.

[Chem. 45]

$$AOCF_2C\text{-}Q\text{-}CF_2COA' \qquad (M\text{-}1)$$

In the polycondensed polymer, the organic group Q can have various substituents as mentioned above. The polymer, when having a hydroxyl group, a carboxyl group, an alkoxy group, a hexafluoroisopropanol group or an amino group that serves as a cross-linking site, can form a three-dimensional cross-linking structure by the action of a cross-linking agent for improvement in resin performance. The polymer, when having a nitro group or a protected amino group, can form a three-dimensional cross-linking structure by modification or deprotection of such a nitro or protected amino group.

[Fluorinated Dicarboxylic Acid]

The fluorinated dicarboxylic acid of the present invention is represented by the following general formula (M-3).

[Chem. 46]

$$HOOCF_2C\text{-}Q\text{-}CF_2COOH \qquad (M\text{-}3)$$

In the general formula (M-3), Q has the same definition as in the general formula (M-1). Specific examples of Q of the general formula (M-3) are the same as those of the general formula (M-1).

The above novel fluorinated dicarboxylic acid derivative can be prepared with reference to Journal of Fluorine Chemistry, 2004, Vol. 125, P. 509-515 etc. For example, it is feasible to prepare the fluorinated dicarboxylic acid derivative by using a dihalogenoaryl compound, preferably a diiodoaryl compound, as a starting maerial, forming a bis(alkoxycarbonyldifluoromethyl)aryl compound by reaction of the dihalogenoaryl compound with a halogenodifluoroacetic acid ester, preferably a bromodifluoroacetic acid ethyl ester, in the presence of copper, hydrolyzing the bis(alkoxycarbonyldifluoromethyl)aryl compound to a carboxylic acid and, if required, halogenating the carboxylic acid to an acid halide.

One general scheme is indicated below (formula [1]).

[Chem. 47]

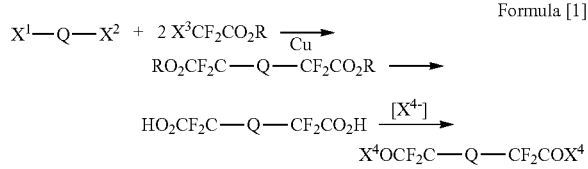

Formula [1]

In the above formula, $X^1$, $X^2$, $X^3$ and $X^4$ each independently represent a halogen atom; and R represents a $C_1$-$C_6$ straight, branched or cyclic alkyl group or a $C_6$-$C_{10}$ substituted or unsubstituted aryl group.

First, the production of the bis(alkoxycarbonyldifluoromethyl)aryl compound will be explained. There is no particular limitation on the process of production of the bis(alkoxycarbonyldifluoromethyl)aryl compound. The bis(alkoxycarbonyldifluoromethyl)aryl compound can be produced by any known process with the use of copper as will be exemplified later.

There is no particular limitation on the amount of the halogenodifluoroacetic acid ester reacted with the dihalogenoaryl compound. The amount of the halogenodifluoroacetic acid ester is generally 1.8 to 3 mol, preferably 1.9 to 2.2 mol, more preferably substantially 2 mol, per 1 mol of the dihalogenoaryl compound. If the amount of the halogenodifluoroacetic acid ester is less than 1.8 mol, the dihalogenoaryl compound cannot be entirely consumed in the reaction. If the amount of the halogenodifluoroacetic acid ester is 3 mol or more, there preferentially occurs a side reaction so that the yield of the target bis(alkoxycarbonyldifluoromethyl)aryl compound becomes lowered.

There is also no particular limitation on the amount of the copper used for the reaction of the dihalogenoaryl compound. The amount of the copper is generally 1 to 20 mol, preferably 2 to 15 mol, more preferably 3 to 10 mol, per 1 mol of the dihalogenoaryl compound. The copper is preferably used in particle form. It is however undesirable that the copper is of coarse particle size. Further, it is preferable to activate the copper by any known process such as treatment with an aqueous hydrochloric acid solution etc. before use.

Preferably, the reaction is performed in a solvent. Suitable examples of the reaction solvent are polar solvents such as acetonitrile, N,N-dimethylformamide, N,N-dimethylimidazolidinone, dimethyl sulfoxide and sulfolane. Particularly preferred are N,N-dimethylformamide and dimethyl sulfoxide. These solvents can be used solely or in combination of two or more thereof.

The reaction temperature is generally in the range of room temperature to 100° C., preferably 40 to 80° C., more preferably 50 to 60° C.

The reaction time varies depending on the reaction temperature, but is generally in the range of several minutes to 100 hours, preferably 30 minutes to 50 hours, more preferably 1 to 20 hours. It is desirable to determine the time at which the raw material i.e. dihalogenoaryl compound has been consumed as the end of the reaction while monitoring the progress of the reaction by any analytical means such as nuclear magnetic resonance (NMR) or gas chromatography.

After the completion of the reaction, the bis(alkoxycarbonyldifluoromethyl)aryl compound can be obtained by ordinary operation such as extraction or recrystallization. The bis(alkoxycarbonyldifluoromethyl)aryl compound may be purified by distillation, recrystallization etc. as needed.

Next, the hydrolysis of the bis(alkoxycarbonyldifluoromethyl)aryl compound will be explained. There is no particular limitation on the process of hydrolysis of the bis(alkoxycarbonyldifluoromethyl)aryl compound. The bis(alkoxycarbonyldifluoromethyl)aryl compound can be hydrolyzed by any known process as will be exemplified later.

In general, the hydrolysis reaction is performed in the presence of a base as a catalyst. As the base, there can be used a hydroxide, a bicarbonate or a carbonate of at least one kind of alkali metal, an ammonia or an amine. Examples of the alkali metal compound are sodium hydroxide, potassium hydroxide, lithium hydroxide, sodium hydrogencarbonate, potassium hydrogencarbonate, sodium carbonate and potassium carbonate. Examples of the amine are methylamine, dimethylamine, trimethylamine, ethylamine, diethylamine, triethylamine, propylamine, dipropylamine, tripropylamine, butylamine, dibutylamine, tributylamine, cyclohexylamine, benzylamine, morpholine, pyrrole, pyrrolidine, pyridine, ethanolamine, diethanolamine, triethanolamine, N,N-dimethylaminoethanol, N,N-diethylaminoethanol, ethylenediamine, diethylenetriamine, triethylenetetramine, 1,2-propylenediamine, dipropylenetriamine, tripropylenetetramine and quaternary ammonium hydroxide salts thereof.

Among these bases, alkali metal compounds such as sodium hydroxide, potassium hydroxide, lithium hydroxide, sodium hydrogencarbonate, potassium hydrogencarbonate, sodium carbonate and potassium carbonate are preferred. Particularly preferred are alkali metal hydroxides such as sodium hydroxide and potassium hydroxide.

The mol ratio of the base used relative to bis(alkoxycarbonyldifluoromethyl)aryl compound is generally 0.01 to 10, preferably 1.0 to 5, more preferably 1 to 3.

In general, the hydrolysis reaction is performed in the presence of water. The mol ratio of the water used relative to the bis(alkoxycarbonyldifluoromethyl)aryl compound is generally 1 or higher. There is no upper limit on the mol ratio of the water used relative to the bis(alkoxycarbonyldifluoromethyl)aryl compound. However, the efficiency of the reaction deteriorates with the use of too large amount of water. The mol ratio of the water used relative to the bis(alkoxycarbonyldifluoromethyl)aryl compound is preferably 100 or lower, more preferably 50 or lower.

An organic solvent may be used in combination with water as needed. There is no particular limitation on the organic solvent used. The organic solvent used is preferably immiscible with water and capable of extracting the bis(hydroxycarbonyldifluoromethyl)aryl compound produced in the reaction from the aqueous layer. Examples of such an organic solvent are: esters such as ethyl acetate and n-butyl acetate; ethers such as diethyl ether; and alkyl halides such as methylene chloride and chloroform.

In this case, the amount of the organic solvent is generally 5 parts by mass or more, preferably 10 parts by mass or more, more preferably 20 to 90 parts by mass, per 100 parts by mass of the sum of the water and organic solvent.

The reaction temperature is generally in the range of 0 to 100° C., preferably 5 to 80° C. The reaction time is generally in the range of 10 minutes to 16 hours, preferably 30 minutes to 6 hours. It is desirable to determine the time at which the raw material i.e. bis(alkoxycarbonyldifluoromethyl)aryl compound has been consumed as the end of the reaction while monitoring the progress of the reaction by any analytical means such as nuclear magnetic resonance (NMR) or gas chromatography.

After the completion of the reaction, the bis(hydroxycarbonyldifluoromethyl)aryl compound can be obtained by ordinary operation such as extraction or recrystallization. The bis(hydroxycarbonyldifluoromethyl)aryl compound may be purified by column chromatography, distillation, recrystallization etc. as needed.

The halogenation of the bis(hydroxycarbonyldifluoromethyl)aryl compound will be next explained. There is no particular limitation on the process of halogenation of the bis(hydroxycarbonyldifluoromethyl)aryl compound. The bis(hydroxycarbonyldifluoromethyl)aryl compound can be halogenated by any known process. For example, the following chlorination process can be adopted.

In the chlorination process, the bis(hydroxycarbonyldifluoromethyl)aryl compound is chlorinated by contact with an chlorination agent in the presence or absence of a solvent under heating.

Examples of the chlorination agent are general-purpose chlorination agents such as thionyl chloride, sulfuryl chloride, phosgene, oxalyl chloride, phosphoryl chloride, phosphorous trichloride, phosphorous pentachloride, dichlorotriphenylphosphorane and dibromotriphenylphosphorane. In particular, thionyl chloride, phosphoryl chloride and oxalyl chloride are preferably used because of low cost and high reactivity.

The amount of the chlorination agent is generally 1.6 to 20 mol, preferably 2 to 10 mol, per 1 mole of the bis(hydroxycarbonyldifluoromethyl)aryl compound.

There is no particular limitation on the reaction solvent used as long as the reaction solvent is inert under the chlorination reaction conditions. Examples of the reaction solvent are benzene, toluene, xylene, methylene chloride, 1,2-dichloroethane, chloroform and carbon tetrachloride. In the case of using the liquid chlorination agent such as thionyl chloride, the chlorination agent also serves a solvent so that there is no need to use the solvent separately.

The chlorination reaction temperature is generally in the range of 25 to 200° C., preferably 30 to 120° C. The reaction time is generally in the range of 10 minutes to 16 hours, preferably 30 minutes to 6 hours. It is desirable to determine the time at which the raw material i.e. bis(hydroxycarbonyldifluoromethyl)aryl compound has been consumed as the end of the reaction while monitoring the progress of the reaction by any analytical means such as nuclear magnetic resonance (NMR) or gas chromatography.

After the completion of the reaction, the bis(hydroxycarbonyldifluoromethyl)aryl compound can be obtained by ordinary operation such as extraction or recrystallization. The bis(hydroxycarbonyldifluoromethyl)aryl compound may be purified by column chromatography, distillation, recrystallization etc. as needed.

One specific preparation example of the fluorinated dicarboxylic acid derivative of the present invention is as follows (scheme [2]; see Example 1).

[Chem. 48]

Formula [2]

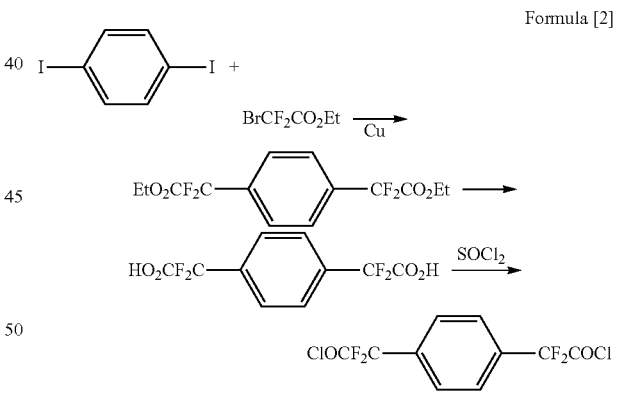

[Polymer Obtained from Fluorinated Dicarboxylic Acid Derivative]

The polymer of the present invention is obtained by polycondensation of the fluorinated dicarboxylic acid derivative of the general formula (M-1) or the acid anhydride of the fluorinated dicarboxylic acid with a polyfunctional compound having two to four reactive groups corresponding in reactivity to carbonyl moieties of the fluorinated dicarboxylic acid derivative or acid anhydride.

[Chem. 49]

$$AOCF_2C\text{-}Q\text{-}CF_2COA' \tag{M-1}$$

In the above formula, Q, A and A' have the same meanings as above.

As the reactive groups of the polyfunctional compound reactive with the carbonyl moieties, there can be used a hydroxyl group, an activated hydroxyl group, an amino group, an activated amino group and the like. The polyfunctional compound needs at least two reactive groups. Although the reactive groups of the polyfunctional compound can be of two or more kinds, it is preferable that two of the reactive groups of the polyfunctional compound are of the same kind.

The process of polymerization of the fluorinated dicarboxylic acid derivative for production of the polymer will be explained below. The fluorinated dicarboxylic acid derivative has two $CF_2CO$ groups and, in some cases, may have three or more functional groups including these $CF_2CO$ groups. These functional groups are utilized effectively for the production of the polymer. It is preferable to utilize the reactivity of the $CF_2CO$ groups preferentially.

In the polymer of the present invention (the general formulas (6) to (11)), m (positive integer) indicates the number of repeating monomer units (the degree of polymerization) It is preferable that m is 5 to 10000, more preferably 10 to 1000. The polymer of the present invention is obtained in the form of a polymer mixture whose polymerization degree ranges over a certain width. The weight-average molecular weight of the polymer is generally preferably 1000 to 5000000, more preferably 2000 to 200000. The polymerization degree and molecular weight of the polymer can be controlled to a desired level by adjusting the after-mentioned polymerization conditions as appropriate.

[Polyeser]

In the present invention, the fluorinated dicarboxylic acid derivative of the general formula (M-1) or the acid anhydride of the fluorinated dicarboxylic acid can be converted to a polyester of the following general formula (6) by contact of the fluorinated dicarboxylic acid derivative or acid anhydride with a diol of the following general formula (2) in a given temperature range.

[Chem. 50]

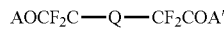
(M-1)
$AOCF_2C-Q-CF_2COA'$

[Chem. 51]

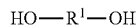
(2)
$HO-R^1-OH$

[Chem. 52]

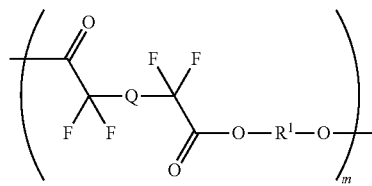
(6)

In the above formulas, Q, A and A' have the same meanings as above.

The diol of the general formula (2) will be now explained. The diol may be in the form of an activator having an activated group to react with the carboxyl moiety for improvement in reactivity. Examples of such an activator are alkali metal (lithium, sodium, potassium) salts of the diol (e.g. dialkoxide).

In the general formula (2), $R^1$ represents a divalent organic group having at least one kind selected from an alicyclic ring, an aromatic ring and a heterocyclic ring and may contain a fluorine atom, a chlorine atom, an oxygen atom, a sulfur atom or a nitrogen atom. A part of hydrogen atoms of $R^1$ may be substituted with a fluorine atom, a chlorine atom, an alkyl group, a fluoroalkyl group, a carboxy group, a hydroxyl group or a cyano group. A part of carbon atoms of $R^1$ may be replaced by an oxygen atom, a sulfur atom, a nitrogen atom, a carbonyl group or a sulfonyl group. Further, m represents a positive integer.

Suitable specific examples of the diol are 1,4-cyclohexanediol, 1,3-adamantanediol, catechol, 1,3-benzenediol, 2,2'-dihydroxybiphenyl, 4,4'-dihydroxybiphenyl, 2,2'-methylenediphenol, 4,4'-methylenediphenol, ethylene glycol, propylene glycol, 2,2-bis(4-hydroxyphenyl)-propane, 2,2-bis(4-hydroxyphenyl)-3-methylpropane, 2,2-bis(4-hydroxyphenyl)-butane, 3,3-bis(4-hydroxyphenyl)-pentane, 2,2-bis(4-hydroxyphenyl)-4-methylpentane, 3,3-bis(4-hydroxyphenyl)-hexane, 2,2-bis(3-chloro-4-hydroxyphenyl)-propane, 2,2-bis(3,5-dichloro-4-hydroxyphenyl)-propane, 2,2-bis(3-bromo-4-hydroxyphenyl)-propane, 2,2-bis(3,5-dibromo-4-hydroxyphenyl)-propane, 2,2-bis(3-methyl-4-hydroxyphenyl)-propane, 2,2-bis(4-hydroxyphenyl)-1,1,1,3,3,3-hexafluoropropane, 2,6-dihydroxynaphthalene, 2,3-dihydroxynaphthalene, 2,7-dihydroxynaphthalene, 1,4-dihydroxynaphthalene, 1,5-dihydroxynaphthalene, 2,3-dihydroxypyridine, 2,4-dihydroxypyridine, 4,4'-dihydroxydiphenylether, 4,4'-dihydroxyldiphenylsulfide, 4,4'-dihydroxydiphenylsulfoxide, 4,4'-dihydroxyphenylsulfone and 4,4'-dihydroxybenzophenone. The diol is not however limited to these compounds in the present invention.

The polyester of the present invention can be produced by any known process with no particular limitation. It is feasible to produce the polymer of the general formula (6) by direct dehydration condensation of the fluorinated dicarboxylic acid of the general formula (M-3) and the diol of the general formula (2) in the presence of a condensation agent.

It is also feasible to produce the polymer of the general formula (6) by reaction of the fluorinated dicarboxylic acid derivative of the general formula (M-1) where A and A' each independently represent a fluorine atom, a chlorine atom, a bromine atom, an iodine atom, a $C_1$-$C_6$ straight, branched or cyclic alkoxy group or a $C_6$-$C_{10}$ substituted or unsubstituted aryloxy group, or the acid anhydride of the fluorinated dicarboxylic acid derivative, with the diol of the general formula (2). In this case, a metal salt such as lithium bromide or lithium chloride as a polymer dissolution accelerator, a dehydrator such as sulfuric acid, phosphoric acid or phosphorus pentoxide, or an acid acceptor such as amine may be used.

Specific examples of the polyester production process are: a process of reacting the fluorinated dicarboxylic acid or derivative thereof etc. with the diol in no solvent system by dissolving (melting) at 150 to 350° C., preferably 200 to 300° C.; and a process of reacting the fluorinated dicarboxylic acid or derivative thereof etc. with the diol in an organic solvent under high-temperature conditions (150 to 350° C., preferably 200 to 300° C.). There can also be used a process of reacting the fluorinated dicarboxylic acid derivative of the general formula (M-1) with the diol in an organic solvent at a temperature of −20 to 80° C. when A and A' are each independently a fluorine atom, a chlorine atom, a bromine atom or an iodine atom in the general formula (M-1). When the fluorinated dicarboxylic acid derivative has a hydroxyl group or an alkoxy group as A and A', there can be used a process of reacting the fluorinated dicarboxylic acid derivative with the diol in an organic solvent at a temperature of −20 to 80° C. with the use of a polymer dissolution accelerator.

The most convenient process is to conduct polycondensation of the fluorinated dicarboxylic acid derivative of the general formula (M-1) (where A and A' are each independently a fluorine atom, a chlorine atom, a bromine atom or an iodine atom) or the acid anhydride of the fluorinated dicarboxylic acid with the diol of the general formula (2) by mixing in an organic solvent. The ratio between the total mol number of the fluorinated dicarboxylic acid derivative of the general formula (M-1) or the acid anhydride of the fluorinated dicarboxylic acid and the total mol number of the diol in the polymerization process is generally in the range of 0.5 to 1.5, more preferably 0.8 to 1.2. As in the case of the ordinary polycondensation reaction, the molecular weight of the resulting polymer can be increased as the mole number ratio is closer to 1.

There is no particular limitation on the organic solvent as long as both of the raw material components can be dissolved in the organic solvent. Examples of the organic solvent are: amide solvents such as N,N-dimethylformamide, N,N-dimethylacetamide, N,N-methylformamide, hexamethylphosphoric triamide and N-methyl-2-pyrrolidone; aromatic solvents such as benzene, anisole, diphenyl ether, nitrobenzene and benzonitrile; halogenated solvents such as chloroform, dichloromethane, 1,2-dichloroethane and 1,1,2,2-tetrachloroethane; and lactone solvents such as γ-butyrolactone, γ-valerolactone, δ-valerolactone, γ-caprolactone, ε-caprolactone and α-methyl-γ-butyrolactone. It is effective to perform the reaction in the coexistence of an acid acceptor such as pyridine or triethylamine with the organic solvent. The polyester can attain a high polymerization degree by the use of the above amide solvent as the amide solvent itself serves as an acid acceptor.

[Polyamide]

In the present specification, the term "polyamide" may include a polyamide diol, a highly fluorinated polyamide and a polybenzoxazole or heterocyclic polymer obtained by ring closure of the polyamide diol or highly fluorinated polyamide as will be explained below.

In the present invention, the fluorinated dicarboxylic acid derivative of the general formula (M-1) or the acid anhydride of the fluorinate dicarboxylic acid can be converted to a polyamide of the general formula (7) by contact of the fluorinated dicarboxylic acid derivative or acid anhydride with a diamine of the general formula (3) in a given temperature range.

[Chem. 53]

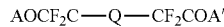

(M-1)

AOCF$_2$C—Q—CF$_2$COA'

[Chem. 54]

H$_2$N—R$^2$—NH$_2$ (3)

[Chem. 55]

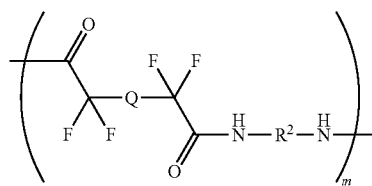

(7)

In the above formulas, Q, A and A' have the same meanings as above.

When Q has an amino group, it is conceivable to subject the fluorinated dicarboxylic acid derivative or acid anhydride as it is but is preferable to subject the fluorinated dicarboxylic acid derivative or acid anhydride to polycondensation after protecting the amino group by the protecting group.

The diamine of the general formula (3) will be now explained below. The diamine may be in the form of an activator having an activated group to react with the carboxyl moiety for improvement in reactivity. Examples of such an activator are diamines with trialkylsilylamino groups (where three alkyl groups selected from methyl, ethyl, propyl and i-propyl and may be the same as or different from each other).

In the general formula (3) and in the general formula (7), R$^2$ represents a divalent organic group having at least one kind selected from an alicyclic ring, an aromatic ring and a heterocyclic ring and may contain a fluorine atom, a chlorine atom, an oxygen atom, a sulfur atom or a nitrogen atom. A part of hydrogen atoms of R$^2$ may be substituted with a fluorine atom, a chlorine atom, an alkyl group, a fluoroalkyl group, a carboxyl group, a hydroxyl group or a cyano group. A part of carbon atoms of R$^2$ may be replaced by an oxygen atom, a sulfur atom, a nitrogen atom, a carbonyl group or a sulfonyl group. Further, m represents a positive integer.

Suitable specific examples of the diamine of the general formula (3) are 1,4-diaminocyclohexane, 3,5-diaminobenzotrifluoride, 2,5-diaminobenzotrifluoride, 3,3'-bis(trifluoromethyl)-4,4'-diaminobiphenyl, 3,3'-bis(trifluoromethyl)-5,5'-diaminobiphenyl, bis(trifluoromethyl)-4,4'-diaminodiphenyl, bis(fluoroalkyl)-4,4'-diaminodiphenyl, dichloro-4,4'-diaminodiphenyl, dibromo-4,4'-diaminodiphenyl, bis(fluoroalkoxy)-4,4'-diaminodiphenyl, diphenyl-4,4'-diaminodiphenyl, 4,4'-bis(4-aminotetrafluorophenoxy)tetrafluorobenzene, 4,4'-bis(4-aminotetrafluorophenoxy)octafluorobiphenyl, 4,4'-binaphthylamine, o-, m- or p-phenylenediamine, 2,4-diaminotoluene, 2,5-diaminotoluene, 2,4-diaminoxylene, 2,4-diaminodurene, dimethyl-4,4'-diaminodiphenyl, dialkyl-4,4'-diaminodiphenyl, dimethoxy-4,4'-diaminodiphenyl, diethoxy-4,4'-diaminodiphenyl, 4,4'-diaminodiphenyl methane, 4,4'-diaminodiphenyl ether, 3,4'-diaminodiphenyl ether, 4,4'-diaminodiphenylsulfone, 3,3'-diaminodiphenylsulfone, 4,4'-diaminobenzophenone, 3,3'-diaminobenzophenone, 1,3-bis(3-aminophenoxy)benzene, 1,3-bis(4-aminophenoxy)benzene, 1,4-bis(4-aminophenoxy)benzene, 4,4'-bis(4-aminophenoxy)biphenyl, bis(4-(3-aminophenoxy)phenyl)sulfone, bis(4-(4-aminophenoxy)phenyl)sulfone, 2,2-bis(4-(4-aminophenoxy)phenyl) propane, 2,2-bis(4-(4-aminophenoxy)phenyl) hexafluoropropane, 2,2-bis(4-(3-aminophenoxy)phenyl) propane, 2,2-bis(4-(3-aminophenoxy)phenyl) hexafluoropropane, 2,2-bis(4-(4-amino-2-trifluoromethylphenoxy)phenyl)hexafluoropropane, 2,2-bis(4-(3-amino-5-trifluoromethylphenoxy)phenyl) hexafluoropropane, 2,2-bis(4-aminophenyl) hexafluoropropane, 2,2-bis(3-aminophenyl) hexafluoropropane, 2,2-bis(3-amino-4-hydroxyphenyl) hexafluoropropane, 2,2-bis(3-amino-4-methylphenyl) hexafluoropropane, 4,4'-bis(4-aminophenoxy) octafluorobiphenyl, 4,4'-diaminobenzanilide, 2,6-diaminonaphthalene, 2,3-diaminonaphthalene, 2,7-diaminonaphthalene, 1,4-diaminonaphthalene, 1,5-diaminonaphthalene, 2,3-diaminopyridine and 2,4-diaminopyridine. The diamine is not however limited to these compounds in the present invention.

The polyamide of the present invention can be produced by any known process with no particular limitation. It is feasible to produce the polymer of the general formula (7) by direct dehydration condensation of the fluorinated dicarboxylic acid of the general formula (M-3) and the diamine of the general formula (3) in the presence of a condensation agent.

It is also feasible to produce the polymer of the general formula (7) by reaction of the fluorinated dicarboxylic acid derivative of the general formula (M-1) where A and A' each independently represent a fluorine atom, a chlorine atom, a bromine atom, an iodine atom, a $C_1$-$C_6$ straight, branched or cyclic alkoxy group or a $C_6$-$C_{10}$ substituted or unsubstituted aryloxy group, or the acid anhydride of the fluorinated dicarboxylic acid derivative, with the diamine of the general formula (3). In this case, a metal salt such as lithium bromide or lithium chloride as a polymer dissolution accelerator, a dehydrator such as sulfuric acid, phosphoric acid or phosphorus pentoxide, or an acid acceptor such as amine may be used.

Specific examples of the polyamide production process are: a process of reacting the fluorinated dicarboxylic acid or derivative thereof etc. with the diamine in no solvent system by dissolving (melting) at 150 to 400° C., preferably 200 to 350° C.; and a process of reacting the fluorinated dicarboxylic acid or derivative thereof etc. with the diamine in an organic solvent under high-temperature conditions (150 to 400° C., preferably 200 to 350° C.). There can also be used a process of reacting the fluorinated dicarboxylic acid derivative of the general formula (M-1) with the diamine in an organic solvent at a temperature of −20 to 80° C. when A and A' are each independently a fluorine atom, a chlorine atom, a bromine atom or an iodine atom in the general formula (M-1). When the fluorinated dicarboxylic acid derivative has a hydroxyl group or an alkoxy group as A and A', there can be a process of reacting the fluorinated dicarboxylic acid derivative with the diamine in an organic solvent at a temperature of −20 to 80° C. with the use of a polymer dissolution accelerator.

The most convenient process is to conduct polycondensation of the fluorinated dicarboxylic acid derivative of the general formula (M-1) (where A and A' are each independently a fluorine atom, a chlorine atom, a bromine atom or an iodine atom) or the acid anhydride of the fluorinated dicarboxylic acid with the diamine of the general formula (3) by mixing in an organic solvent. The ratio between the total mol number of the fluorinated dicarboxylic acid derivative of the general formula (M-1) or the acid anhydride of the fluorinated dicarboxylic acid and the total mol number of the diamine in the polymerization process is generally in the range of 0.5 to 1.5, more preferably 0.8 to 1.2. As in the case of the ordinary polycondensation reaction, the molecular weight of the resulting polymer can be increased as the mole number ratio is closer to 1.

There is no particular limitation on the organic solvent as long as both of the raw material components can be dissolved in the organic solvent. Examples of the organic solvent are: amide solvents such as N,N-dimethylformamide, N,N-dimethylacetamide, N,N-methylformamide, hexamethylphosphoric triamide and N-methyl-2-pyrrolidone; aromatic solvents such as benzene, anisole, diphenyl ether, nitrobenzene and benzonitrile; halogenated solvents such as chloroform, dichloromethane, 1,2-dichloroethane and 1,1,2,2-tetrachloroethane; and lactone solvents such as γ-butyrolactone, γ-valerolactone, δ-valerolactone, γ-caprolactone, ε-caprolactone and α-methyl-γ-butyrolactone. It is effective to perform the reaction in the coexistence of an acid acceptor such as pyridine or triethylamine with the organic solvent. The polyester can attain a high polymerization degree by the use of the above amide solvent as the amide solvent itself serves as an acid acceptor.

[Polyamide Diol]

The fluorinated dicarboxylic acid derivative of the general formula (M-1) can be polymerized to a polyamide diol of the general formula (8) by contact of the fluorinated dicarboxylic acid derivative with a diaminodiol of the general formula (4) in a given temperature range.

[Chem. 56]

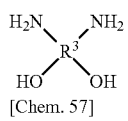

(4)

[Chem. 57]

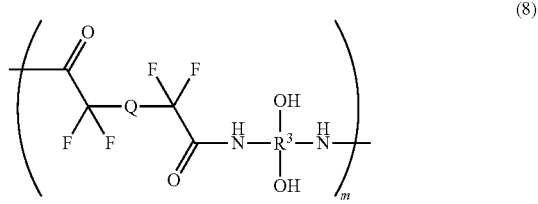

(8)

When Q has an amino group, it is conceivable to subject the fluorinated dicarboxylic acid derivative to polycondensation as it is but is preferable to subject the fluorinated dicarboxylic acid derivative to polycondensation after protecting the amino group by the protection group.

In the general formula (4) and in the general formula (8), $R^3$ represents a quaternary organic group having at least one kind selected from an alicyclic ring, an aromatic ring and a heterocyclic ring and may contain a fluorine atom, a chlorine atom, an oxygen atom, a sulfur atom or a nitrogen atom. A part of hydrogen atoms of $R^3$ may be substituted with a fluorine atom, a chlorine atom, an alkyl group, a fluoroalkyl group, a carboxyl group, a hydroxyl group or a cyano group. A part of carbon atoms of $R^3$ may be replaced by an oxygen atom, a sulfur atom, a nitrogen atom, a carbonyl group or a sulfonyl group. Further, m represents a positive integer.

Suitable specific examples of the diaminodiol of the general formula (4) are 2,4-diamino-1,5-cyclohexanediol, 2,4-diamino-1,5-benzenediol, 3,3'-dihydroxy-4,4'-diaminobiphenyl, 3,3'-diamino-4,4'-dihydroxybiphenyl, bis(3-amino-4-hydroxyphenyl)ketone, bis(3-amino-4-hydroxyphenyl)sulfide, bis(3-amino-4-hydroxyphenyl)ether, bis(3-hydroxy-4-aminophenyl)sulfone, 2,2-bis(3-amino-4-hydroxyphenyl)propane, 2,2-bis(3-hydroxy-4-amionophenyl)propane, bis(3-hydroxy-4-aminophenyl)methane, 2,2-bis(3-amino-4-hydroxyphenyl)hexafluoropropane, 2,2-bis(3-hydroxy-4-aminophenyl)hexafluoropropane, bis(3-amino-4-hydroxyphenyl)difluoromethane, 2,6-diamino-1,5-naphthalenediol, 1,5-diamino-2,6-naphthalenediol and 2,6-diamino-3,5-pyridinediol. The diaminodiol is not however limited to these compounds in the present invention.

The polyamide diol of the present invention can be produced by any known process with no particular limitation. It is feasible to produce the polymer of the general formula (8) by direct dehydration condensation of the fluorinated dicarboxylic acid of the general formula (M-3) and the diaminodiol of the general formula (4) in the presence of a condensation agent.

It is also feasible to produce the polymer of the general formula (8) by reaction of the fluorinated dicarboxylic acid derivative of the general formula (M-1) where A and A' each independently represent a fluorine atom, a chlorine atom, a bromine atom, an iodine atom, a $C_1$-$C_6$ straight, branched or cyclic alkoxy group or a $C_6$-$C_{10}$ substituted or unsubstituted aryloxy group, or the acid anhydride of the fluorinated dicarboxylic acid derivative, with the diaminodiol of the general formula (4). In this case, a metal salt such as lithium bromide or lithium chloride as a polymer dissolution accelerator, a dehydrator such as phosphoric acid or phosphorus pentoxide, or an acid acceptor such as amine may be used.

There is no particular restriction on the polymerization process and conditions. As the elementary reaction of the polymerization is amide formation, the polyamide diol can be produced by the same process with the use of the same solvent as the polyamide of the general formula (7).

The thus-obtained polyamide phenol resin (polyamide diol) may be further converted to a polybenzoxazole resin of the general formula (9) by dehydration ring closure.

[Chem. 58]

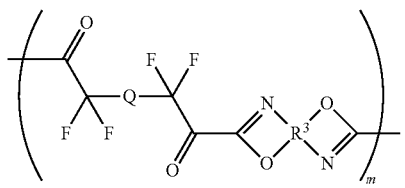
(9)

In the general formula (9), $R^3$ has the same meaning as in the general formula (4).

The dehydration ring closure can be conducted by any known process, without particular limitation, with the use of various means such as heating, acid catalyst or basic catalyst for accelerated dehydration conditions. In the case of performing the ring closure reaction under heating, the ring closure temperature can be set to 80 to 400° C. and is preferably set to 150 to 350° C. The heating time is generally of the order of 30 minutes to 2 hours although it suffices that the heating time is of the order of 10 minutes to 10 hours. If the ring closure temperature is 150° C. or lower, the resulting film of the polybenzoxazole may unfavorably deteriorate in strength due to low ring closure rate. If the ring closure temperature is 350° C. or higher, the resulting film of the polybenzoxazole may face a problem of coloring or embrittlement. Examples of the acid catalyst used are p-toluenesulfonic acid and methanesulfonic acid. Examples of the base catalyst used are triethylamine and pyridine. When the polybenzoxazole obtained after the ring closure is soluble in an organic solvent, it is feasible to chemically carry out the ring closure reaction in an organic solution with the use of a dehydration agent such as acetic anhydride and an organic base such as pyridine or triethylamine.

Further, it is feasible to subject a highly-fluorinated polyamide resin of the general formula (10) to ring closure after applying the polyamide resin to various articles. By such cyclization (dehydration ring closure), the resin can be modified to show large changes in performance, such as improvement of thermal resistance, change of solubility, decrease of refractive index or dielectric constant and development of hydrophobic and lipophobic properties.

[Highly-Fluorinated polyamide]

The fluorinated dicarboxylic acid derivative of the general formula (M-1) can be polymerized to a highly-fluorinated polyamide resin of the general formula (10) by contact of the fluorinated dicarboxylic acid derivative with a hexafluoroisopropanol-substituted diaminodiol of the general formula (5) in a given temperature range.

[Chem. 59]

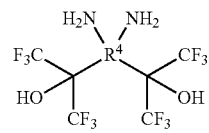
(5)

[Chem. 60]

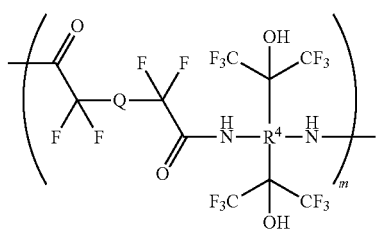
(10)

In the general formula (5) and in the general formula (10), $R^4$ represents a quaternary organic group having at least one kind selected from an alicyclic ring, an aromatic ring, a condensed polycyclic aromatic ring and a heterocyclic ring and may contain a fluorine atom, a chlorine atom, an oxygen atom, a sulfur atom or a nitrogen atom. A part of hydrogen atoms of $R^4$ may be substituted with a fluorine atom, a chlorine atom, an alkyl group, a fluoroalkyl group, a carboxyl group, a hydroxyl group or a cyano group. A part of carbon atoms of $R^4$ may be replaced by an oxygen atom, a sulfur atom, a nitrogen atom, a carbonyl group or a sulfonyl group. Further, m represents a positive integer.

Suitable specific examples of the hexafluoroisopropanol-substituted diaminodiol of the general formula (5) are exemplified as follows. The hexafluoroisopropanol-substituted diaminodiol is not however limited to these compounds in the present invention.

[Chem. 61]

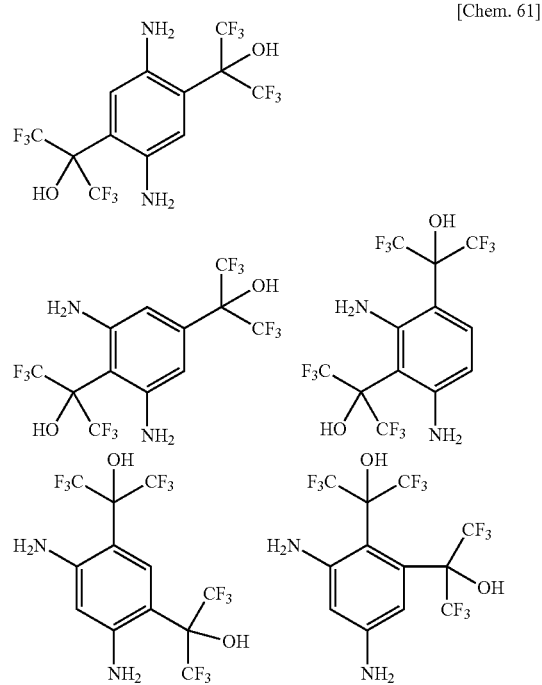

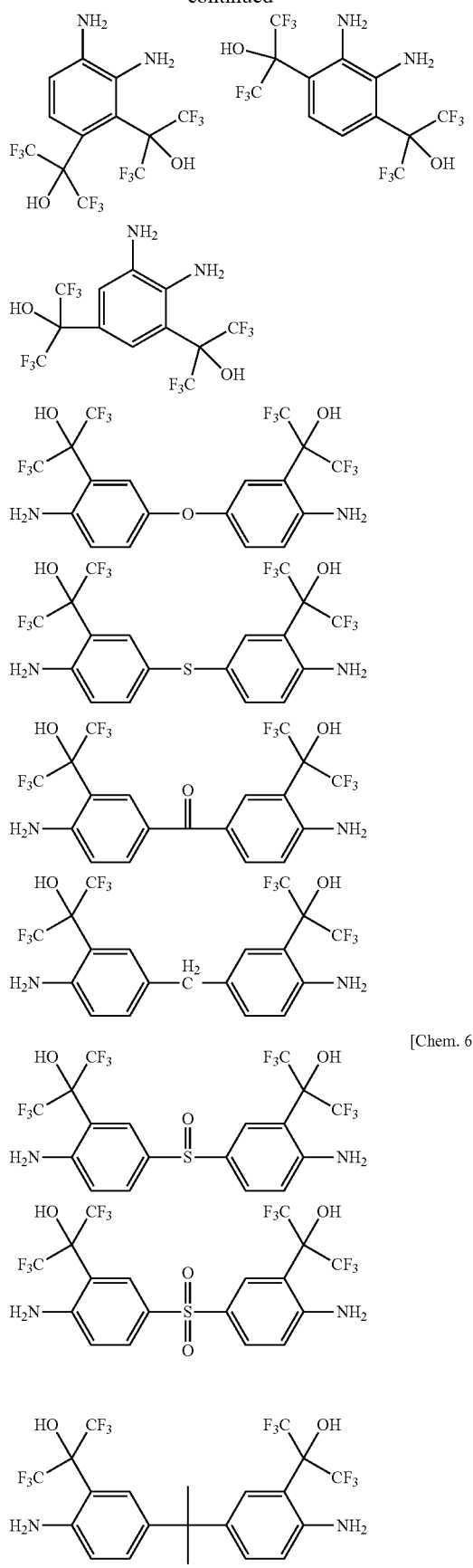
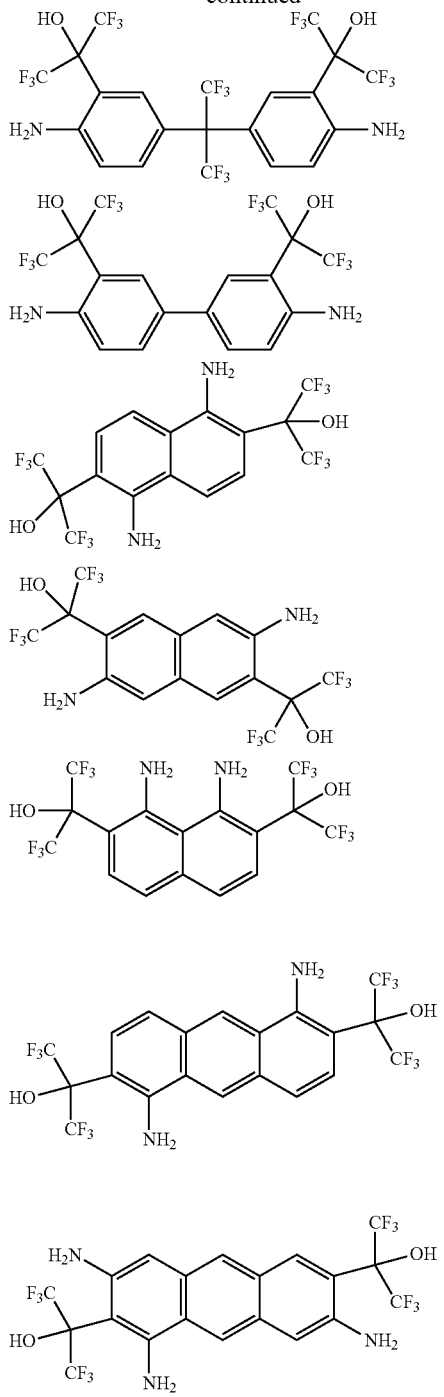

[Chem. 62]

There is no particular limitation on the polymerization reaction process and conditions of the highly-fluorinated polyamide. As the elementary reaction of the polymerization is amide formation, the highly-fluorinated polyamide can be produced by the same process under the same conditions with the use of the same solvent as the polyamide of the general formula (7).

The thus-obtained highly-fluorinated polyamide resin of the general formula (10) may be further converted to a heterocyclic polymer of the general formula (11) by dehydration ring closure.

[Chem. 63]

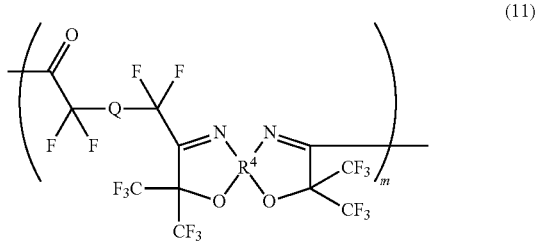

(11)

In the general formula (11), $R^4$ has the same meaning as in the general formula (5).

There is no particular limitation on the conditions of the dehydration ring closure. In the dehydration ring closure, various means such as heating, acid catalyst or basic catalyst are usable for accelerated dehydration conditions.

The dehydration ring closure can be performed by any known process, without particular limitation, with the use of various means such as heating, acid catalyst or basic catalyst for accelerated dehydration conditions. In the case of performing the ring closure reaction under heating, the ring closure temperature can be set to 80 to 400° C. and is preferably set to 150 to 350° C. The ring closure reaction can be completed at substantially about 250° C. If the ring closure temperature is 150° C. or lower, the resulting film of the heterocyclic polymer may unfavorably deteriorate in strength due to low ring closure rate. If the ring closure temperature is 350° C. or higher, the resulting film of the heterocyclic polymer may face a problem of coloring or embrittlement. Examples of the acid catalyst are p-toluenesulfonic acid and methanesulfonic acid. Examples of the base catalyst are triethylamine and pyridine. When the heterocyclic polymer obtained after the ring closure is soluble in an organic solvent, it is feasible to chemically carry out the ring closure reaction in an organic solution with the use of a dehydration agent such as acetic anhydride and an organic base such as pyridine or triethylamine. The heterocyclic structure of the general formula (11) can be formed by dehydration ring closure under more moderate conditions than the oxazole structure of the general formula (9).

Further, it is feasible to treat the highly-fluorinated polyamide resin of the general formula (10) at a temperature of 80 to 400° C. after applying a solvent solution of the polyamide resin to various articles. At this time, the treatment temperature is preferably set to 150 to 350° C. The polyamide resin can be converted by ring closure to the heterocyclic polymer of the general formula (11) at substantially about 250° C. By such cyclization (dehydration ring closure), the resin can be modified to show large changes in performance, such as improvement of thermal resistance, change of solubility, decrease of refractive index or dielectric constant and development of hydrophobic and lipophobic properties.

The heterocyclic polymer of the general formula (11) has trifluoromethyl groups on its heterocyclic structure and thus exhibits a lower dielectric constant, lower water absorption and higher transparency than those of the polybenzoxazole of the general formula (9).

There are the following examples of applications of the fluorinated polymer of the present invention. The polyester or polyamide of the present invention can be used in varnish form by dissolving in an organic solvent or can be used in powder form, film form or solid form. At this time, additives such as antioxidant, filler, silane coupling agent, photosensitizer, photopolymerization initiator and sensitizer may be added to the fluorinated polymer as needed. When the polymer is used in varnish form, it is feasible to apply the polymer vanish to a substrate of glass, silicon wafer, metal, metal oxide, ceramic, resin etc. by ordinary process such as spin coating, spray coating, flow coating, immersion coating or brush coating. The polymer is formed into a film (coating) with desired performance by heating after the application process and increasing the polymerization degree of the polymer. The film-forming reaction temperature is preferably 300° C. or lower, more preferably 250° C. or lower, although the film-forming reaction can proceeds at a temperature of the order of 150 to 350° C. The polyamide of the general formula (8) or (10) can be subjected to ring closure by heating and thereby converted to the heterocyclic polymer of the general formula (11).

Examples of the organic solvent used in the above applications are: amide solvents such as N,N-dimethylformamide, N,N-dimethylacetamide, N,N-methylformamide, hexamethylphosphoric triamide and N-methyl-2-pyrrolidone; lactone solvents such as γ-butyrolactone, γ-valerolactone, δ-valerolactone, γ-caprolactone, ε-caprolactone and α-methyl-γ-butyrolactone; and concentrated sulfuric acid.

The present invention will be described in more detail below by way of the following examples. It is noted that the following examples are illustrative and are not intended to limit the present invention thereto.

Example 1

Preparation of 1,4-benzenediacetic acid-α,α⁴,β,β⁴-tetrafluoro-1,4-diethyl ester

[Chem. 64]

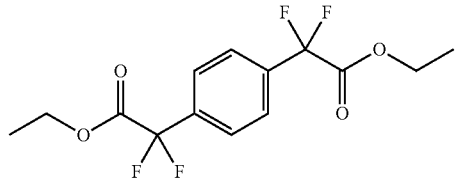

Into a 1-L glass flask with a condenser, 50 g (152 mmol/1.0 eq) of 1,4-diiodobenzene, 44 g (692 mmol/4.6 eq) of copper metal powder and 250 mL of dimethyl sulfoxide (dehydrated) were placed. Further, 83 g (408 mmol/2.6 eq) of ethyl bromodifluoroacetate was dropped into the glass flask. The resulting solution was stirred for 8 hours at 55° C. The completion of the reaction was confirmed by gas chromatography. The reacted solution was admixed with water and chloroform to thereby precipitate an insoluble matter out of the solution. The insoluble matter was filtered out. The filtrate was separated into an organic layer and an aqueous layer. The organic layer was sequentially washed with diluted hydrochloric acid, water and saturated sodium chloride solution, dried, and then, subjected to vacuum concentration. With this, 54 g of 1,4-benzenediacetic acid-α,α⁴,β,β⁴-tetrafluoro-1,4-diethyl ester was obtained as an yellow oily substance (yield: 82%, purity: 74%).

Properties of 1,4-benzenediacetic acid-α,α⁴,β,β⁴-tetrafluoro-1,4-diethyl ester $^1$H NMR (measurement solvent: chloroform-d, standard: tetramethylsilane); δ=7.69 (s, 4H), 4.29 (q, J=7.1 Hz, 4H; $CH_2$ of C—$CH_2CH_3$), 1.29 (t, J=7.1 Hz, 6H; $CH_3$ of C—$CH_2CH_3$).

$^{19}$F NMR (measurement solvent: chloroform-d, standard: trichlorofluoromethane); δ=−104.68 (s, 4F).

Example 2

Preparation of α,α⁴,β,β⁴-tetrafluoro-1,4-benzenediacetic acid

[Chem. 65]

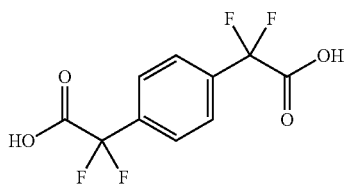

Into a 250-mL glass flask, 15 g (purity: 74%, 34 mmol) of the diester obtained in Example 1, 40 mL of water and 9.6 g (115 mmol/3.3 eq) of 48% aqueous sodium hydroxide solution were added. The resulting solution was stirred for 18 hours at room temperature. The completion of the reaction was confirmed by $^{19}$F NMR. The reacted solution was washed twice with 40 mL of diisopropyl ether, followed by dropping thereto 60 mL (60 mmol/1.8 eq) of 1 mol/L hydrochloric acid. After confirming that the pH of the solution was adjusted to 1, the solution was further stirred for 1 hour at room temperature and separated into an organic layer and an aqueous layer by the addition of 100 mL of diisopropyl ether. The aqueous layer was extracted twice with 100 mL of diisopropyl ether. The extracted organic layers were combined, and then, subjected to vacuum concentration. With this, 8.2 g of α,α⁴,β,β⁴-tetrafluoro-1,4-benzenediacetic acid was obtained as a pale yellow solid substance (yield: 70%, purity: 90%).

Properties of α,α⁴,β,β⁴-tetrafluoro-1,4-benzenediacetic acid $^{1}$H NMR (measurement solvent: deuterium dimethyl sulfoxide, standard: tetramethylsilane); δ=7.75 (s, 4H).
$^{19}$F NMR (measurement solvent: deuterium dimethyl sulfoxide, standard: trichlorofluoromethane); δ=−102.54 (s, 4F).

Example 3

Preparation of 1,3-benzenediacetic acid-α,α³,β,β³-tetrafluoro-1,3-diethyl ester

[Chem. 66]

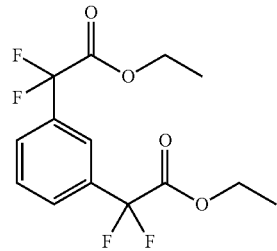

Into a 1-L glass flask with a condenser, 50 g (152 mmol/1.0 eq) of 1,3-diiodobenzene, 43 g (677 mmol/4.5 eq) of copper metal powder and 250 mL of dimethyl sulfoxide (dehydrated) were placed. Further, 70 g (345 mmol/2.3 eq) of ethyl bromodifluoroacetate was dropped into the glass flask. The resulting solution was stirred for 8 hours at 55° C. The completion of the reaction was confirmed by gas chromatography. The reacted solution was admixed with water and chloroform to thereby precipitate an insoluble matter out of the solution. The insoluble matter was filtered out. The filtrate was separated into an organic layer and an aqueous layer. The organic layer was sequentially washed with diluted hydrochloric acid, water and saturated sodium chloride solution, dried, and then, subjected to vacuum concentration. With this, 49 g of 1,3-benzenediacetic acid-α,α³,β,β³-tetrafluoro-1,3-diethyl ester was obtained as an yellow oily substance (yield: 51%, purity: 52%).

Properties of 1,3-benzenediacetic acid-α,α³,β,β³-tetrafluoro-1,3-diethyl ester $^{1}$H NMR (measurement solvent: chloroform-d, standard: tetramethylsilane); δ=7.85 (s, 1H), 7.73 (d, J=7.8 Hz, 2H), 7.55 (t, J=7.1 Hz, 1H) 4.29 (q, J=7.1 Hz, 4H; CH$_2$ of C—CH$_2$CH$_3$), 1.30 (t, J=7.1 Hz, 6H; CH$_3$ of C—CH$_2$CH$_3$).
$^{19}$F NMR (measurement solvent: chloroform-d, standard: trichlorofluoromethane); δ=−104.35 (s, 4F).

Example 4

Preparation of α,α³,β,β³-tetrafluoro-1,3-benzenediacetic acid

[Chem. 67]

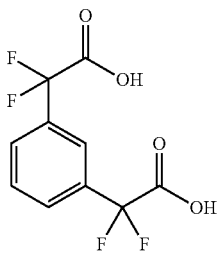

Into a 250-mL glass flask, 21 g (purity: 52%, 34 mmol) of the diester obtained in Example 3, 40 mL of water and 9.6 g (115 mmol/3.3 eq) of 48% aqueous sodium hydroxide solution were added. The resulting solution was stirred for 18 hours at room temperature. The completion of the reaction was confirmed by $^{19}$F NMR. The reacted solution was washed twice with 40 mL of diisopropyl ether, followed by dropping thereto 60 mL (60 mmol/1.8 eq) of 1 mol/L hydrochloric acid. After confirming that the pH of the solution was adjusted to 1, the solution was further stirred for 1 hour at room temperature and separated into an organic layer and an aqueous layer by the addition of 100 mL of diisopropyl ether. The aqueous layer was extracted twice with 100 mL of diisopropyl ether. The extracted organic layers were combined, and then, subjected to vacuum concentration. With this, 4.5 g of α,α³,β,β³-tetrafluoro-1,3-benzenediacetic acid was obtained as a pale yellow solid substance (yield: 47%, purity: 95%).

Properties of α,α³,β,β³-tetrafluoro-1,3-benzenediacetic acid $^{1}$H NMR (measurement solvent: deuterium dimethyl sulfoxide, standard: tetramethylsilane); δ=7.85-7.65 (m, 4H).
$^{19}$F NMR (measurement solvent: deuterium dimethyl sulfoxide, standard: trichlorofluoromethane); δ=−102.30 (s, 4F).

Example 5

Preparation of α,α⁴,β,β⁴-tetrafluoro-1,4-benzenediacetyl chloride

[Chem. 68]

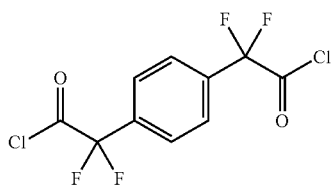

Into a 250-mL glass flask with a condenser, 49 g (purity: 90%, 167 mmol/1.0 eq) of a dicarboxylic acid obtained in the same manner as in Examples 1 and 2 and 50 mL of acetonitrile were added. Further, 50 g (420 mmol/2.5 eq) of thionyl chloride was dropped into the glass flask. The resulting solution was stirred for 18 hours at room temperature. The completion of the reaction was confirmed by $^{19}$F NMR. The reacted solution was then subjected to vacuum concentration. With this, 47 g of α,α⁴,β,β⁴-tetrafluoro-1,4-benzenediacetyl chloride was obtained as an yellow oily substance (yield: 85%, purity: 90%).

Properties of α,α⁴,β,β⁴-tetrafluoro-1,4-benzenediacetyl chloride $^1$H NMR (measurement solvent: chloroform-d, standard: tetramethylsilane); δ=7.76 (s, 4H).
$^{19}$F NMR (measurement solvent: chloroform-d, standard: trichlorofluoromethane); δ=−101.32 (s, 4F).

Example 6

Preparation of α,α³,β,β³-tetrafluoro-1,3-benzenediacetyl chloride

[Chem. 69]

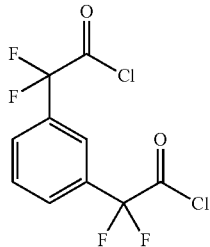

Into a 250-mL glass flask with a condenser, 32 g (purity: 93%, 113 mmol/1.0 eq) of a dicarboxylic acid obtained in the same manner as in Examples 3 and 4 and 50 mL of acetonitrile were placed. Further, 30 g (252 mmol/2.2 eq) of thionyl chloride was dropped into the glass flask. The resulting solution was stirred for 18 hours at room temperature. The completion of the reaction was confirmed by $^{19}$F NMR. The reacted solution was then subjected to vacuum concentration. With this, 34 g of α,α³,β,β³-tetrafluoro-1,3-benzenediacetyl chloride was obtained as an yellow oily substance (yield: 81%, purity: 73%).

Properties of α,α³,β,β³-tetrafluoro-1,3-benzenediacetyl chloride $^1$H NMR (measurement solvent: chloroform-d, standard: tetramethylsilane); δ=7.86 (s, 1H), 7.81 (d, J=7.8 Hz, 2H), 7.67 (t, J=7.1 Hz, 1H).
$^{19}$F NMR (measurement solvent: chloroform-d, standard: trichlorofluoromethane); δ=−101.10 (s, 4F).

Example 7

Preparation of 5-methoxy-1,3-benzenediacetic acid-α,α⁴,β,β⁴-tetrafluoro-1,3-diethyl ester

[Chem. 70]

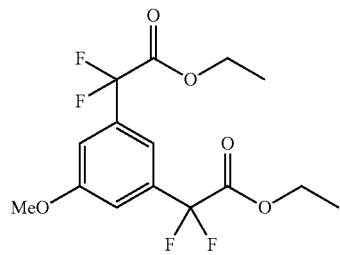

Into a 1-L glass flask with a condenser, 50 g (139 mmol/1.0 eq) of 1,3-diiodo-5-methoxybenzene, 44 g (692 mmol/5.0 eq) of copper metal powder and 250 mL of dimethyl sulfoxide (DMSO) (dehydrated) were placed. Further, 71 g (350 mmol/2.5 eq) of ethyl bromodifluoroacetate was dropped into the glass flask. The resulting solution was stirred for 7 hours at 55° C. The completion of the reaction was confirmed by gas chromatography. The reacted solution was admixed with water and chloroform to thereby precipitate an insoluble matter out of the solution. The insoluble matter was filtered out. The filtrate was separated into an organic layer and an aqueous layer. The organic layer was sequentially washed with diluted hydrochloric acid, water and saturated sodium chloride solution, dried, and then, subjected to vacuum concentration. With this, 52 g of 5-methoxy-1,3-benzenediacetic acid-α,α⁴,β,β⁴-tetrafluoro-1,4-diethyl ester was obtained as an yellow oily substance (yield: 80%, purity: 75%).

Properties of 5-methoxy-1,3-benzenediacetic acid-α,α⁴,β,β⁴-tetrafluoro-1,4-diethyl ester $^1$H NMR (measurement solvent: chloroform-d, standard: tetramethylsilane); δ=6.37 (s, 2H), 6.44 (s, 1H), 4.13 (q, J=7.0 Hz, 4H; CH₂ of C—CH₂CH₃), 3.73 (s, 3H; CH₃ of O—CH₃), 1.30 (t, J=7.0 Hz, 6H; CH₃ of C—CH₂CH₃).
$^{19}$F NMR (measurement solvent: chloroform-d, standard: trichlorofluoromethane); δ=−104.30 (s, 4F).

Example 8

Preparation of 5-methoxy-α,α⁴,β,β⁴-tetrafluoro-1,3-benzenediacetic acid

[Chem. 71]

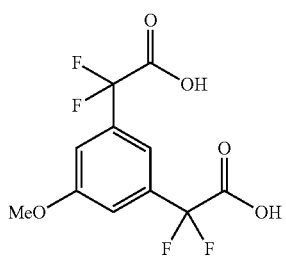

Into a 250-mL glass flask, 15 g (purity: 75%, 32 mmol) of the diester obtained in Example 7, 40 mL of water and 10.0 g (120 mmol/3.8 eq) of 48% aqueous sodium hydroxide solution were added. The resulting solution was stirred for 18 hours at room temperature. The completion of the reaction was confirmed by $^{19}$F NMR. The reacted solution was washed twice with 40 mL of diisopropyl ether, followed by dropping thereto 60 mL (60 mmol/1.9 eq) of 1 mol/L hydrochloric acid. After confirming that the pH of the solution was adjusted to 1, the solution was further stirred for 1 hour at room temperature and separated into an organic layer and an aqueous layer by the addition of 100 mL of diisopropyl ether. The aqueous layer was extracted twice with 100 mL of diisopropyl ether. The extracted organic layers were combined, and then, subjected to vacuum concentration. With this, 8.1 g of 5-methoxy-α,α⁴,β,β⁴-tetrafluoro-1,3-benzenediacetic acid was obtained as a pale yellow solid substance (yield: 75%, purity: 88%).

Properties of 5-methoxy-α,α⁴,β,β⁴-tetrafluoro-1,3-benzenediacetic acid $^1$H NMR (measurement solvent: deuterium dimethyl sulfoxide, standard: tetramethylsilane);
δ=12.30 (s, 1H; OH), 6.42 (s, 2H), 6.46 (s, 1H), 3.77 (s, 3H; CH$_3$ of O—CH$_3$).
$^{19}$F NMR (measurement solvent: deuterium dimethyl sulfoxide, standard: trichlorofluoromethane); δ=−103.50 (s, 4F).

Example 9

Preparation of 5-methoxy-α,α³,β,β³-tetrafluoro-1,3-benzenediacetyl chloride

[Chem. 72]

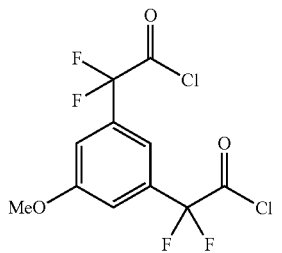

Into a 250-mL glass flask with a condenser, 30 g (89.1 mmol/1.0 eq) of a dicarboxylic acid obtained in the same manner as in Examples 7 and 8 and 50 mL of acetonitrile were added. Further, 50 g (purity: 89%, 252 mmol/2.8 eq) of thionyl chloride was dropped into the glass flask. The resulting solution was stirred for 18 hours at room temperature. The completion of the reaction was confirmed by $^{19}$F NMR. The reacted solution was then subjected to vacuum concentration. With this, 31 g of 5-methoxy-α,α³,β,β³-tetrafluoro-1,3-benzenediacetyl chloride was obtained as an yellow oily substance (yield: 78%, purity: 75%).

Properties of 5-methoxy-α,α³,β,β³-tetrafluoro-1,3-benzenediacetyl chloride $^1$H NMR (measurement solvent: deuterium dimethyl sulfoxide, standard: tetramethylsilane);
δ=6.41 (s, 2H), 6.45 (s, 1H), 3.76 (s, 3H; CH$_3$ of O—CH$_3$).
$^{19}$F NMR (measurement solvent: deuterium dimethyl sulfoxide, standard: trichlorofluoromethane); δ=−102.30 (s, 4F).

Example 10

Preparation of 2,2'-(diphenyl-4,4'-diyl)bis(2,2-difluoroacetic acid)diethyl ester

[Chem. 73]

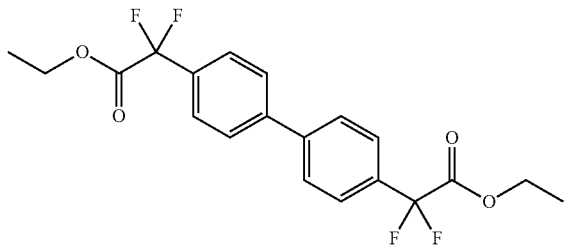

Into a 100-mL glass flask with a condenser, 5.0 g (12.3 mmol/1.0 eq) of 4,4'-diiodobiphenyl, 3.5 g (55.1 mmol/4.5 eq) of copper metal powder and 50 mL of dimethyl sulfoxide (DMSO) (dehydrated) were placed. Further, 5.5 g (27.1 mmol/2.2 eq) of ethyl bromodifluoroacetate was dropped into the glass flask. The resulting solution was stirred for 7 hours at 55° C. The completion of the reaction was confirmed by gas chromatography. The reacted solution was admixed with water and chloroform to thereby precipitate an insoluble matter out of the solution. The insoluble matter was filtered out. The filtrate was separated into an organic layer and an aqueous layer. The organic layer was sequentially washed with diluted hydrochloric acid, water and saturated sodium chloride solution, dried, and then, subjected to vacuum concentration. With this, 3.1 g of 2,2'-(diphenyl-4,4'-diyl)bis(2,2-difluoroacetic acid)diethyl ester was obtained as an yellow solid substance (yield: 43%, purity: 68%).

Properties of 2,2'-(diphenyl-4,4'-diyl)bis(2,2-difluoroacetic acid)diethyl ester $^1$H NMR (measurement solvent: chloroform-d, standard: tetramethylsilane); δ=7.60 (d, J=8.5 Hz, 4H), 7.56 (d, J=8.5 Hz, 4H), 4.22 (q, J=7.1 Hz, 4H; CH$_2$ of C—CH$_2$CH$_3$), 1.22 (t, J=7.1 Hz, 6H; CH$_3$ of C—CH$_2$CH$_3$).
$^{19}$F NMR (measurement solvent: chloroform-d, standard: trichlorofluoromethane); δ=−104.15 (s, 4F).

Example 11

Preparation of 2,2'-(diphenyl-4,4'-diyl)bis(2,2-difluoroacetic acid)

[Chem. 74]

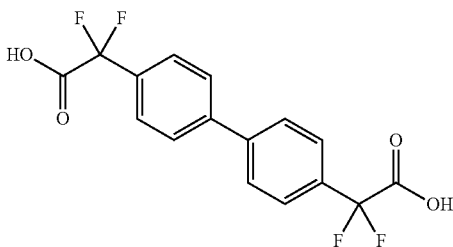

Into a 50-mL glass flask, 2.3 g (purity: 68%, 3.9 mmol) of the diester obtained in Example 10, 5 ml, of water and 0.65 g (11.7 mmol/3.0 eq) of 48% aqueous sodium hydroxide solution were added. The resulting solution was stirred for 4.5 hours at room temperature. The completion of the reaction was confirmed by $^{19}$F NMR. The reacted solution was washed twice with 40 mL of diisopropyl ether, followed by dropping thereto 10 mL (50 mmol/2.6 eq) of 1 mol/L hydrochloric acid. After confirming that the pH of the solution was adjusted to 1, the solution was further stirred for 1 hour at room temperature and separated into an organic layer and an aqueous layer by the addition of 50 mL of diisopropyl ether. The aqueous layer was extracted twice with 50 mL of diisopropyl ether. The extracted organic layers were combined, and then, subjected to vacuum concentration. With this, 1.5 g of 2,2'-(diphenyl-4,4'-diyl)bis(2,2-difluoroacetic acid) was obtained as a pale yellow solid substance (yield: 86%, purity: 80%).

Properties of 2,2'-(diphenyl-4,4'-diyl)bis(2,2-difluoroacetic acid)

$^1$H NMR (measurement solvent: deuterium dimethyl sulfoxide, standard: tetramethylsilane);
δ=7.89 (d, J=8.5 Hz, 4H), 7.69 (d, J=8.5 Hz, 4H).
$^{19}$F NMR (measurement solvent: deuterium dimethyl sulfoxide, standard: trichlorofluoromethane); δ=−102.12 (s, 4F).

Example 12

Preparation of 2,2'-(diphenyl-4,4'-diyl)bis(2,2-difluoroacetyl chloride)

[Chem. 75]

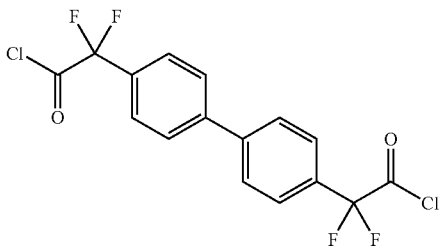

Into a 250-mL glass flask with a condenser, 43 g (purity: 80%, 100 mmol/1.0 eq) of a dicarboxylic acid obtained in the same manner as in Examples 10 and 11 and 80 mL of acetonitrile were added. Further, 30 g (250 mmol/2.5 eq) of thionyl chloride was dropped into the glass flask. The resulting solution was stirred for 24 hours at room temperature. The completion of the reaction was confirmed by $^{19}$F NMR. The reacted solution was then subjected to vacuum concentration. With this, 33 g of 2,2'-(diphenyl-4,4'-diyl)bis(2,2-difluoroacetyl chloride) was obtained as an yellow oily substance (yield: 79%, purity: 91%).

Properties of 2,2'-(diphenyl-4,4'-diyl)bis(2,2-difluoroacetyl chloride)

$^1$H NMR (measurement solvent: deuterium dimethyl sulfoxide, standard: tetramethylsilane); δ=7.75 (d, J=8.5 Hz, 4H), 7.57 (d, J=8.5 Hz, 4H).
$^{19}$F NMR (measurement solvent: deuterium dimethyl sulfoxide, standard: trichlorofluoromethane); δ=−100.92 (s, 4F).

Reference Example 1

Preparation of 1,2-benzenediacetic acid-α,α$^2$,β,β$^2$-tetrafluoro-1,2-diethyl ester

[Chem. 76]

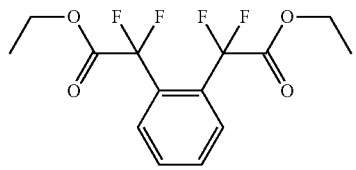

In the same manner as in Example 1 using 25 g (76 mmol/1.0 eq) of 1,2-diiodobenzene, 23 g (362 mmol/4.8 eq) of copper metal powder, 250 mL of dimethyl sulfoxide (DMSO) (dehydrated) and 42 g (204 mmol/2.7 eq) of ethyl bromodifluoroacetate, 26 g of 1,2-benzenediacetic acid-α,α$^2$,β,β$^2$-tetrafluoro-1,2-diethyl ester was obtained as an yellow oily substance (yield: 80%, purity: 75%).

Reference Example 2

Preparation of α,α$^2$,β,β$^2$-tetrafluoro-1,2-benzenediacetic acid

[Chem. 77]

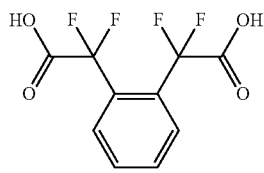

In the same manner as in Example 2 using 20 g (purity: 75%, 47 mmol) of the diester obtained in Reference Example 1, 50 ml of water and 13 g (155 mmol/3.3 eq) of 48% aqueous sodium hydroxide solution, 11 g of α,α$^2$,β,β$^2$-tetrafluoro-1, 2-benzenediacetic acid was obtained as a pale yellow solid substance (yield: 75%, purity: 87%).

Reference Example 3

Preparation of α,α²,β,β²-tetrafluoro-1,2-benzenediacetyl chloride

[Chem. 78]

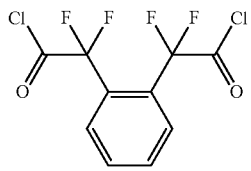

In the same manner as in Example 5 using 10 g (purity: 87%, 33 mmol/1.0 eq) of the dicarboxylic acid obtained in Reference Example 2, 20 mL of acetonitrile and 12 g (100 mmol/3.0 eq) of thionyl chloride, 9 g of α,α²,β,β²-tetrafluoro-1,2-benzenediacetyl chloride was obtained as a pale yellow solid substance (yield: 84%, purity: 93%).

Reference Example 4

Preparation of 1-[2,2,2-trifluoro-1-hydroxy-1-(trifluoromethyl)ethyl]-3,5-dibromobenzene

[Chem. 79]

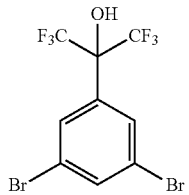

Under a nitrogen atmosphere, 30.0 g (95.0 mmol) of 1,3,5-tribromobenzene and 400 mL of diethyl ether were placed in a 500-mL glass flask and cooled to −78° C. Further, 60 ml (96.0 mmol) of 1.6M n-butyl lithium hexane solution was dropped into the glass flask at −78° C. over 1 hour. The resulting solution was subjected to aging at −78° C. for 1 hour. The lithiation of the raw material was confirmed by gas chromatography. After that, 16.6 g (100.0 mmol) of hexafluoroacetone was charged into the solution at −78° C. and stirred for 1 hour. After the completion of the stirring, the reacted solution was separated into an organic layer and an aqueous layer by the addition of 400 mL of 2N hydrochloric acid. The aqueous layer was extracted with 100 mL of isopropyl ether. The extracted organic layers were combined, dried with anhydrous magnesium sulfate, concentrated by an evaporator, and then, subjected to distillation. With this, 23 g of 1-[2,2,2-trifluoro-1-hydroxy-1-(trifluoromethyl)ethyl]-3,5-dibromobenzene was obtained. The yield was 60%.

Properties of 1-[2,2,2-trifluoro-1-hydroxy-1-(trifluoromethyl)ethyl]-3,5-dibromobenzene $^1$H NMR (measurement solvent: chloroform-d, standard: tetramethylsilane); δ=7.79 (s, 3H).
$^{19}$F NMR (measurement solvent: chloroform-d, standard: trichlorofluoromethane); δ=−76.0 (s, 6F, CF$_3$).

Reference Example 5

Preparation of 5-[2,2,2-trifluoro-1-hydroxy-1-(trifluoromethyl)ethyl]-1,3-benzenedicarboxylic acid

[Chem. 80]

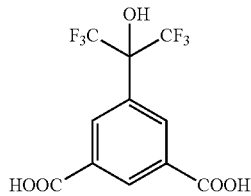

Into a 100-mL autoclave, 10.0 g (26 mmol) of the 1-[2,2,2-trifluoro-1-hydroxy-1-(trifluoromethyl)ethyl]-3,5-dibromobenzene obtained in Reference Example 4, 0.56 g (2.5 mmol) of palladium acetate, 2.63 g (10 mmol) of triphenylphosphine, 10.1 g (100 mmol) of triethylamine, 5.0 g of water and 20 g of tetrahydrofuran were placed. The resulting solution was reacted at 100° C. for 17 hours under 2 MPa of carbon monoxide. After the completion of the reaction, 50 mL of 2N hydrochloric acid was added to the reacted solution. Further, 50 mL of isopropyl ether was added to the reacted solution to extract an organic layer. Subsequently, 60 mL of 7% aqueous sodium hydroxide solution was added to the organic layer to extract an aqueous layer. The aqueous layer was washed with 30 mL of heptane and admixed with 60 mL of 6N hydrochloric acid, thereby precipitating a solid matter out of the solution. The precipitated solid was isolated by filtration and washed with 50 mL of heptane. With this, 3.5 g of 5-[2,2,2-trifluoro-1-hydroxy-1-(trifluoromethyl)ethyl]-1,3-benzenedicarboxylic acid was obtained. The yield was 41%.

Properties of 5-[2,2,2-trifluoro-1-hydroxy-1-(trifluoromethyl)ethyl]-1,3-benzenedicarboxylic acid $^1$H NMR (measurement solvent: chloroform-d, standard: tetramethylsilane); δ=9.27 (s, 1H), 8.58 (m, 1H), 8.46 (s, 2H).
$^{19}$F NMR (measurement solvent: chloroform-d, standard: trichlorofluoromethane); δ=−73.5 (s, 6F, CF$_3$).

Reference Example 6

Preparation of carboxylic acid chloride 1: 5-[2,2,2-trifluoro-1-hydroxy-1-(trifluoromethyl)ethyl]-1,3-benzenedicarboxylic acid chloride Into a 50-mL glass flask, 3.5 g (10.5 mmol) of the 5-[2,2,2-trifluoro-1-hydroxy-1-(trifluoromethyl)ethyl]-1,3-benzenedicarboxylic acid obtained in Reference Example 5 and 20 ml of thionyl chloride were placed. The resulting solution reacted with stirring at 70° C. for 5 hours. After the reaction, the thionyl chloride was removed by evaporation. With this, 3.8 g of 5-[2,2,2-trifluoro-1-hydroxy-1-(trifluoromethyl)

ethyl]-1,3-benzenedicarboxylic acid chloride was obtained as target carboxylic acid chloride 1. The yield was 98%.

Properties of 5-[2,2,2-trifluoro-1-hydroxy-1-(trifluoromethyl)ethyl]-1,3-benzenedicarboxylic acid chloride $^1$H NMR (measurement solvent: chloroform-d, standard: tetramethylsilane); δ=8.52 (m, 1H), 8.41 (s, 2H).

$^{19}$F NMR (measurement solvent: chloroform-d, standard: trichlorofluoromethane); δ=−72.7 (s, 6F, CF$_3$).

Example 13

Synthesis of Polymer 1

[Chem. 81]

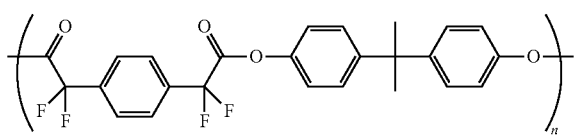

Polymer 1

In a 100-mL three-neck flask with a stirrer, 2.28 g (10.0 mmol) of 2,2-bis(4-hydroxyphenyl)propane (bisphenol A) and 20.0 g of N-methyl-2-pyrrolidone (NMP) were placed. The resulting solution was stirred in a nitrogen atmosphere under ice cooling conditions. To this stirred, cooled solution, the acid chloride (α,α$^4$,β,β$^4$-tetrafluoro-1,4-benzenediacetyl chloride) obtained in Example 5 was slowly added in a net amount of 3.03 g (10.0 mmol) over about 10 minutes. The solution was further stirred for 1 hour. Hydrogen chloride generated in the reaction was neutralized by the addition of 0.70 g (9.5 mmol) of lithium carbonate to the solution. The thus-obtained viscous solution was poured into 500 mL of methanol to form a precipitate in the solution. The precipitate was recovered by filtration and vacuum dried at 80° C. As a result, 4.13 g of polymer 1 was obtained (yield: 90%). The specific viscosity of the polymer 1 was measured at 30° C. using a capillary viscometer and 95% concentrated sulfuric acid as a solvent (The same method was applied to the following examples). The specific viscosity measurement results are indicated in TABLE 1.

The polymer 1 (1.00 g) was mixed with N,N-dimethylformamide (DMF) (4.00 g) to prepare a uniform solution. The prepared solution was filtered. The filtrate was applied by spin coating to a glass substrate and heat treated in a nitrogen atmosphere at 80° C. for 30 minutes, at 150° C. for 30 minutes and at 250° C. for 1 hour, thereby forming a polymer film on the glass substrate. The polymer film was separated from the glass substrate and obtained as a shape-retaining, flexible transparent film. The thickness of the polymer film was about 10 μm. The capacity of the polymer film was measured according to JIS K6911 at a frequency of 100 kHz using a Precision LCR meter HP-4284 manufactured by Hewlett-Packard Company. The specific dielectric constant of the polymer film was determined by the following equation based on the capacity measurement results (the same applies to the following examples). The properties of the polymer film are indicated in TABLE 1. Specific dielectric constant=(capacity measurement value×film thickness)/(dielectric constant under vacuum×measurement area).

Example 14

Synthesis of Polymer 2

[Chem. 82]

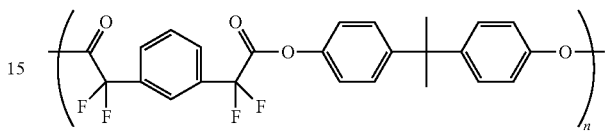

Polymer 2

In the same manner as in Example 13 using the acid chloride (α,α$^3$,β,β$^3$-tetrafluoro-1,3-benzenediacetyl chloride) obtained in Example 6 in a net amount of 3.03 g (10.0 mmol), 2.28 g (10.0 mmol) of bisphenol A and 20 g of N-methyl-2-pyrrolidone (NMP), 3.99 g of polymer 2 was obtained (yield: 87%). The specific viscosity measurement results of the polymer 2 are indicated in TABLE 1.

The polymer 2 (1.00 g) was mixed with N,N-dimethylformamide (DMF) (4.00 g) to prepare a uniform solution. The prepared solution was filtered. The filtrate was applied by spin coating to a glass substrate and heat treated in a nitrogen atmosphere at 80° C. for 30 minutes, at 150° C. for 30 minutes and at 250° C. for 1 hour, thereby forming a polymer film on the glass substrate. The polymer film was separated from the glass substrate and obtained as a shape-retaining, flexible transparent film. The properties of the polymer film are indicated in TABLE 1.

Example 15

Synthesis of Polymer 3

[Chem. 83]

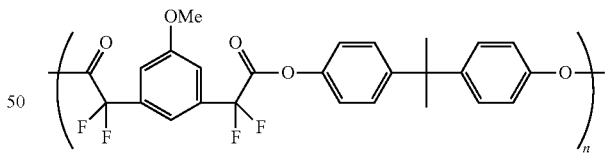

Polymer 3

In the same manner as in Example 13 using the acid chloride (5-methoxy-α,α$^3$,β,β$^3$-tetrafluoro-1,3-benzenediacetyl chloride) obtained in Example 9 in a net amount of 3.33 g (10.0 mmol), 2.28 g (10.0 mmol) of bisphenol A and 20 g of N-methyl-2-pyrrolidone (NMP), 4.21 g of polymer 3 was obtained (yield: 86%). The specific viscosity measurement results of the polymer 3 are indicated in TABLE 1.

The polymer 3 (1.00 g) was mixed with N,N-dimethylformamide (DMF) (4.00 g) to prepare a uniform solution. The prepared solution was filtered. The filtrate was applied by spin coating to a glass substrate and heat treated in a nitrogen atmosphere at 80° C. for 30 minutes, at 150° C. for 30 minutes and at 250° C. for 1 hour, thereby forming a polymer film on the glass substrate. The polymer film was separated from the glass substrate and obtained as a shape-retaining, flexible transparent film. The properties of the polymer film are indicated in TABLE 1.

Example 16

Synthesis of Polymer 4

[Chem. 84]

Polymer 4

[Chem. 85]

Diol 1

In the same manner as in Example 13 using the acid chloride obtained in Example 5 in a net amount of 3.03 g (10.0 mmol), 3.36 g (10.0 mmol) of diol 1 and 20 g of N-methyl-2-pyrrolidone (NMP), 4.64 g of polymer 4 was obtained (yield: 82%). The specific viscosity measurement results of the polymer 4 are indicated in TABLE 1.

The polymer 3 (1.00 g) was mixed with N,N-dimethylformamide (DMF) (4.00 g) to prepare a uniform solution. The prepared solution was filtered. The filtrate was applied by spin coating to a glass substrate and heat treated in a nitrogen atmosphere at 80° C. for 30 minutes, at 150° C. for 30 minutes and at 250° C. for 1 hour, thereby forming a polymer film on the glass substrate. The polymer film was separated from the glass substrate and obtained as a shape-retaining, flexible transparent film. The properties of the polymer film are indicated in TABLE 1.

Example 17

Synthesis of Polymer 5

[Chem. 86]

Polymer 5

[Chem. 87]

Diol 1

In the same manner as in Example 13 using the acid chloride obtained in Example 6 in a net amount of 3.03 g (10.0 mmol), 3.36 g (10.0 mmol) of diol 1 and 20 g of N-methyl-2-pyrrolidone (NMP), 4.81 g of polymer 5 was obtained (yield: 85%). The specific viscosity measurement results of the polymer 5 are indicated in TABLE 1.

The polymer 5 (1.00 g) was mixed with N,N-dimethylformamide (DMF) (4.00 g) to prepare a uniform solution. The prepared solution was filtered. The filtrate was applied by spin coating to a glass substrate and heat treated in a nitrogen atmosphere at 80° C. for 30 minutes, at 150° C. for 30 minutes and at 250° C. for 1 hour, thereby forming a polymer film on the glass substrate. The polymer film was separated from the glass substrate and obtained as a shape-retaining, flexible transparent film. The properties of the polymer film are indicated in TABLE 1.

Example 18

Synthesis of Polymer 6

[Chem. 88]

Polymer 6

[Chem. 89]

Diamine 1

In the same manner as in Example 13 using the acid chloride obtained in Example 5 in a net amount of 3.03 g (10.0 mmol), 2.26 g (10.0 mmol) of diamine 1 and 20 g of N-methyl-2-pyrrolidone (NMP), 4.24 g of polymer 6 was obtained (yield: 93%). The specific viscosity measurement results of the polymer 6 are indicated in TABLE 1.

The polymer 6 (1.00 g) was mixed with N,N-dimethylformamide (DMF) (4.00 g) to prepare a uniform solution. The prepared solution was filtered. The filtrate was applied by spin coating to a glass substrate and heat treated in a nitrogen atmosphere at 80° C. for 30 minutes, at 150° C. for 30 minutes and at 250° C. for 1 hour, thereby forming a polymer film on the glass substrate. The polymer film was separated from the glass substrate and obtained as a shape-retaining, flexible transparent film. The properties of the polymer film are indicated in TABLE 1.

Example 19

Synthesis of Polymer 7

[Chem. 90]

Polymer 7

-continued

[Chem. 91]

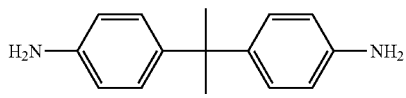

Diamine 1

In the same manner as in Example 13 using the acid chloride obtained in Example 6 in a net amount of 3.03 g (10.0 mmol), 2.26 g (10.0 mmol) of diamine 1 and 20 g of N-methyl-2-pyrrolidone (NMP), 4.154 g of polymer 7 was obtained (yield: 91%). The specific viscosity measurement results of the polymer 7 are indicated in TABLE 1.

The polymer 7 (1.00 g) was mixed with N,N-dimethylformamide (DMF) (4.00 g) to prepare a uniform solution. The prepared solution was filtered. The filtrate was applied by spin coating to a glass substrate and heat treated in a nitrogen atmosphere at 80° C. for 30 minutes, at 150° C. for 30 minutes and at 250° C. for 1 hour, thereby forming a polymer film on the glass substrate. The polymer film was separated from the glass substrate and obtained as a shape-retaining, flexible transparent film. The properties of the polymer film are indicated in TABLE 1.

Example 20

Synthesis of Polymer 8

[Chem. 92]

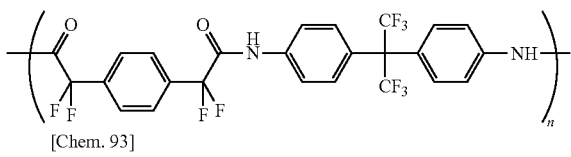

Polymer 8

[Chem. 93]

Diamine 3

In the same manner as in Example 13 using the acid chloride obtained in Example 5 in a net amount of 3.03 g (10.0 mmol), 3.34 g (10.0 mmol) of diamine 2 and 20 g of N-methyl-2-pyrrolidone (NMP), 4.81 g of polymer 8 was obtained (yield: 85%). The specific viscosity measurement results of the polymer 8 are indicated in TABLE 1.

The polymer 8 (1.00 g) was mixed with N,N-dimethylformamide (DMF) (4.00 g) to prepare a uniform solution. The prepared solution was filtered. The filtrate was applied by spin coating to a glass substrate and heat treated in a nitrogen atmosphere at 80° C. for 30 minutes, at 150° C. for 30 minutes and at 250° C. for 1 hour, thereby forming a polymer film on the glass substrate. The polymer film was separated from the glass substrate and obtained as a shape-retaining, flexible transparent film. The properties of the polymer film are indicated in TABLE 1.

Example 21

Synthesis of Polymer 9

[Chem. 94]

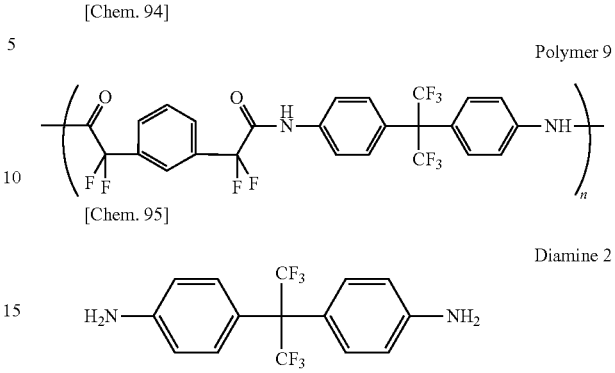

Polymer 9

[Chem. 95]

Diamine 2

In the same manner as in Example 13 using the acid chloride obtained in Example 6 in a net amount of 3.03 g (10.0 mmol), 3.34 g (10.0 mmol) of diamine 2 and 20 g of N-methyl-2-pyrrolidone (NMP), 4.47 g of polymer 9 was obtained (yield: 79%). The specific viscosity measurement results of the polymer 9 are indicated in TABLE 1.

The polymer 9 (1.00 g) was mixed with N,N-dimethylformamide (DMF) (4.00 g) to prepare a uniform solution. The prepared solution was filtered. The filtrate was applied by spin coating to a glass substrate and heat treated in a nitrogen atmosphere at 80° C. for 30 minutes, at 150° C. for 30 minutes and at 250° C. for 1 hour, thereby forming a polymer film on the glass substrate. The polymer film was separated from the glass substrate and obtained as a shape-retaining, flexible transparent film. The properties of the polymer film are indicated in TABLE 1.

Example 22

Synthesis of Polymer 10

[Chem. 96]

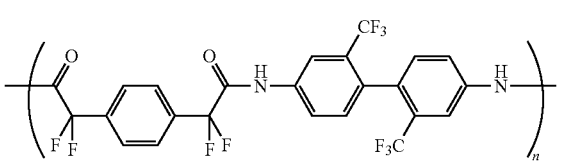

Polymer 10

[Chem. 97]

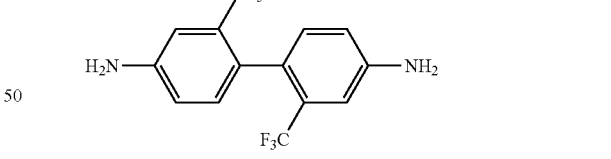

Diamine 3

In the same manner as in Example 13 using the acid chloride obtained in Example 5 in a net amount of 3.03 g (10.0 mmol), 3.20 g (10.0 mmol) of diamine 3 and 20 g of N-methyl-2-pyrrolidone (NMP), 4.52 g of polymer 10 was obtained (yield: 82%). The specific viscosity measurement results of the polymer 10 are indicated in TABLE 1.

The polymer 10 (1.00 g) was mixed with N,N-dimethylformamide (DMF) (4.00 g) to prepare a uniform solution. The filtrate was applied by spin coating to a glass substrate and heat treated in a nitrogen atmosphere at 80° C. for 30 minutes, at 150° C. for 30 minutes and at 250° C. for 1 hour, thereby forming a polymer film on the glass substrate. The polymer film was separated from the glass substrate and obtained as a shape-retaining, flexible transparent film. The properties of the polymer film are indicated in TABLE 1.

Example 23

Synthesis of Polymer 11

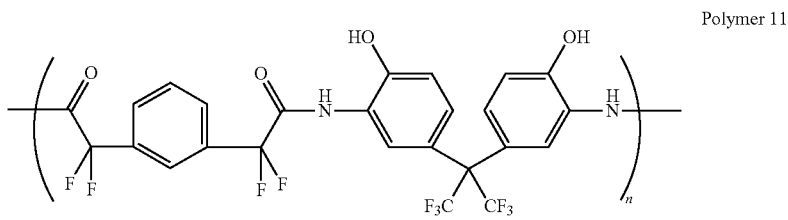

Polymer 11

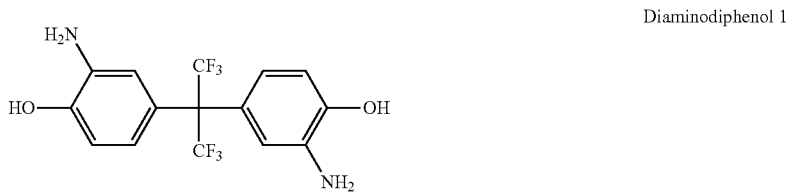

Diaminodiphenol 1

In the same manner as in Example 13 using the acid chloride obtained in Example 6 in a net amount of 3.03 g (10.0 mmol), 3.66 g (10.0 mmol) of diaminodiphenol 1 and 20 g of N-methyl-2-pyrrolidone (NMP), 5.07 g of polymer 11 was obtained (yield: 85%). The specific viscosity measurement results of the polymer 11 are indicated in TABLE 1.

Example 24

Synthesis of Polymer 12

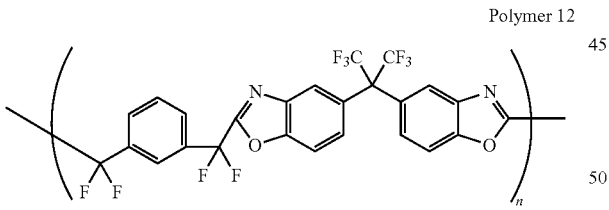

Polymer 12

The polymer 11 (1.00 g) obtained in Example 23 was mixed with N,N-dimethylformamide (DMF) (4.00 g) to prepare a uniform solution. The prepared solution was filtered. The filtrate was applied by spin coating to a glass substrate and heat treated in a nitrogen atmosphere at 80° C. for 30 minutes, at 150° C. for 30 minutes and at 250° C. for 1 hour, thereby forming a polymer film on the glass substrate. The polymer film was separated from the glass substrate and obtained as a shape-retaining, flexible transparent film. It was confirmed by infrared absorption spectrum (IR) analysis that the polymer film was of polymer 12. The properties of the polymer film are indicated in TABLE 1. The polymer film was additionally heat treated at 300° C. for 1 hour in the same manner as above. Then, the same observations and measurements were made on the polymer film. The polymer film was in shape-retaining, flexible transparent film form. There was no difference in the specific dielectric constant of the polymer film between before and after the additional heat treatment.

Example 25

Synthesis of Polymer 13

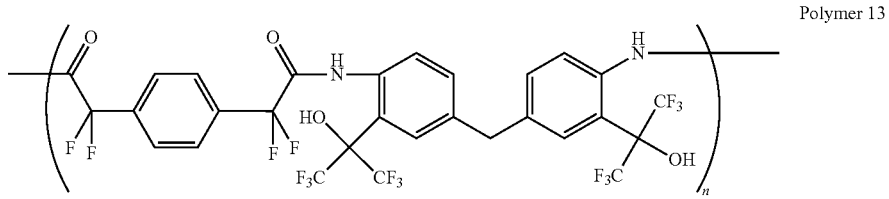

Polymer 13

-continued

[Chem. 102]

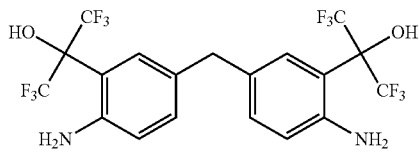

Diaminodiol 1

In the same manner as in Example 13 using the acid chloride obtained in Example 5 in a net amount of 3.03 g (10.0 mmol), 5.30 g (10.0 mmol) of diaminodiphenol 1 prepared in the same manner as described in Japanese Laid-Open Patent Publication No. 2007-119503 and 20 g of N-methyl-2-pyrrolidone (NMP), 6.01 g of polymer 13 was obtained (yield:

[Chem. 104]

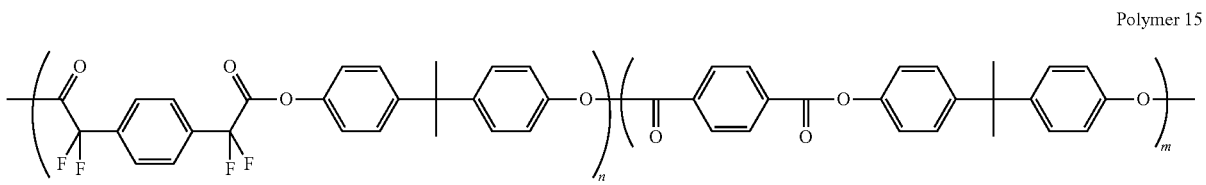

Polymer 15

79%). The specific viscosity measurement results of the polymer 13 are indicated in TABLE 1.

Example 26

Synthesis of Polymer 14

[Chem. 103]

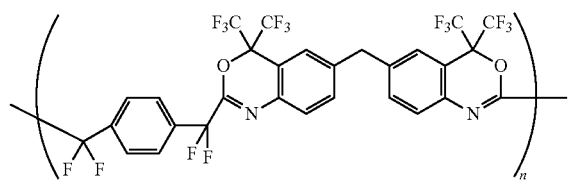

Polymer 14

The polymer 13 (1.00 g) obtained in Example 25 was mixed with N,N-dimethylformamide (DMF) (4.00 g) to prepare a uniform solution. The prepared solution was filtered. The filtrate was applied by spin coating to a glass substrate and heat treated in a nitrogen atmosphere at 80° C. for 30 minutes, at 150° C. for 30 minutes and at 250° C. for 1 hour, thereby forming a polymer film on the glass substrate. The polymer film was separated from the glass substrate and obtained as a shape-retaining, flexible transparent film. It was confirmed by IR analysis that the polymer film was of polymer 14. The properties (specific dielectric constant) of the polymer film are indicated in TABLE 1. The polymer film was additionally heat treated at 300° C. for 1 hour in the same manner as above. Then, the same observations and measurements were made on the polymer film. The polymer film was in shape-retaining, flexible transparent film form. There was no difference in the specific dielectric constant of the polymer film between before and after the additional heat treatment.

Example 27

Synthesis of Polymer 15

In a 100-mL three-neck flask with a stirrer, 2.28 g (10.0 mmol) of 2,2-bis(4-hydroxyphenyl)propane (bisphenol A) and 20.0 g of N-methyl-2-pyrrolidone (NMP) were placed. The resulting solution was stirred in a nitrogen atmosphere under ice cooling conditions. To this stirred, cooled solution, the acid chloride ($\alpha,\alpha^4,\beta,\beta^4$-tetrafluoro-1,4-benzenediacetyl chloride) obtained in Example 5 was slowly added in a net amount of 2.73 g (9.0 mmol), over about 10 minutes, together with 0.20 g (1.0 mmol) of terephthaloyl chloride. The solution was further stirred for 1 hour. Hydrogen chloride generated in the reaction was neutralized by the addition of 0.70 g (9.5 mmol) of lithium carbonate to the solution. The thus-obtained viscous solution was poured into 500 mL of methanol to form a precipitate in the solution. The precipitate was recovered by filtration and vacuum dried at 80° C. As a result, 4.08 g of polymer 15 was obtained (yield: 91%). The specific viscosity measurement results of the polymer 15 are indicated in TABLE 1.

The polymer 15 (1.00 g) was mixed with N,N-dimethylformamide (DMF) (4.00 g) to prepare a uniform solution. The prepared solution was filtered. The filtrate was applied by spin coating to a glass substrate and heat treated in a nitrogen atmosphere at 80° C. for 30 minutes, at 150° C. for 30 minutes and at 250° C. for 1 hour, thereby forming a polymer film on the glass substrate. The polymer film was separated from the glass substrate and obtained as a shape-retaining, flexible transparent film. The properties of the polymer film are indicated in TABLE 1.

Example 28

Synthesis of Polymer 22

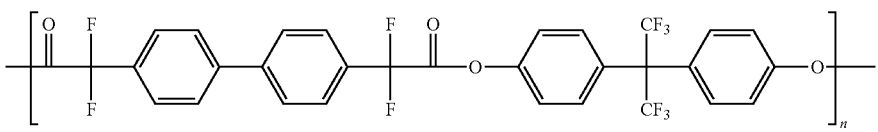

In the same manner as in Example 13 using the 2,2'-(diphenyl-4,4'-diyl)bis(2,2-difluoroacetyl chloride) obtained in Example 12 in a net amount of 3.79 g (10.0 mmol), 3.36 g (10.0 mmol) of diol 1 and 20 g of N-methyl-2-pyrrolidone (NMP), 6.01 g of polymer 22 was obtained (yield: 90%). The specific viscosity measurement results of the polymer 22 are indicated in TABLE 1.

The polymer 22 (1.00 g) was mixed with N,N-dimethylformamide (DMF) (4.00 g) to prepare a uniform solution. The prepared solution was filtered. The filtrate was applied by spin coating to a glass substrate and heat treated in a nitrogen atmosphere at 80° C. for 30 minutes, at 150° C. for 30 minutes and at 250° C. for 1 hour, thereby forming a polymer film on the glass substrate. The polymer film was separated from the glass substrate and obtained as a shape-retaining, flexible transparent film. The properties of the polymer film are indicated in TABLE 1.

Example 29

Synthesis of Polymer 23

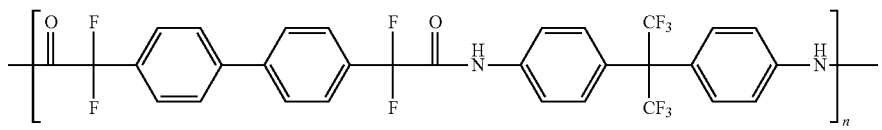

In the same manner as in Example 13 using the 2,2'-(diphenyl-4,4'-diyl)bis(2,2-difluoroacetyl chloride) obtained in Example 12 in a net amount of 3.79 g (10.0 mmol), 3.34 g (10.0 mmol) of diamine 2 and 20 g of N-methyl-2-pyrrolidone (NMP), 5.64 g of polymer 23 was obtained (yield: 90%). The specific viscosity measurement results of the polymer 23 are indicated in TABLE 1. [0174.] The polymer 23 (1.00 g) was mixed with N,N-dimethylformamide (DMF) (4.00 g) to prepare a uniform solution. The prepared solution was filtered. The filtrate was applied by spin coating to a glass substrate and heat treated in a nitrogen atmosphere at 80° C. for 30 minutes, at 150° C. for 30 minutes and at 250° C. for 1 hour, thereby forming a polymer film on the glass substrate. The polymer film was separated from the glass substrate and obtained as a shape-retaining, flexible transparent film. The properties of the polymer film are indicated in TABLE 1.

Example 30

Synthesis of Polymer 24

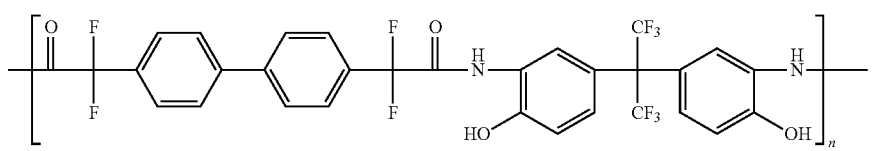

In the same manner as in Example 13 using the 2,2'-(diphenyl-4,4'-diyl)bis(2,2-difluoroacetyl chloride) obtained in Example 12 in a net amount of 3.79 g (10.0 mmol), 3.66 g (10.0 mmol) of diaminodiphenol 1 and 20 g of N-methyl-2-pyrrolidone (NMP), 5.72 g of polymer 24 was obtained (yield: 85%). The specific viscosity measurement results of the polymer 24 are indicated in TABLE 1.

Example 31

Synthesis of Polymer 25

[Chem. 108]

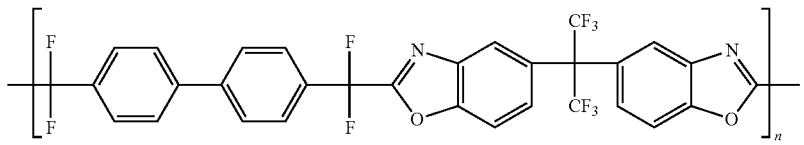

The polymer 24 (1.00 g) was mixed with N,N-dimethylformamide (DMF) (4.00 g) to prepare a uniform solution. The prepared solution was filtered. The filtrate was applied by spin coating to a glass substrate and heat treated in a nitrogen atmosphere at 80° C. for 30 minutes, at 150° C. for 30 minutes and at 250° C. for 1 hour, thereby forming a polymer film on the glass substrate. The polymer film was separated from the glass substrate and obtained as a shape-retaining, flexible transparent film. It was confirmed by IR analysis that the polymer film was of polymer 25. The properties of the polymer film are indicated in TABLE 1.

Example 32

Synthesis of Polymer 26

[Chem. 109]

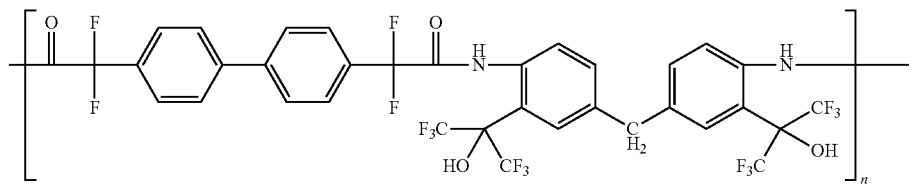

In the same manner as in Example 13 using the 2,2'-(diphenyl-4,4'-diyl)bis(2,2-difluoroacetyl chloride) obtained in Example 12 in a net amount of 3.79 g (10.0 mmol), 5.30 g (10.0 mmol) of diaminodiol 1 and 30 g of N-methyl-2-pyrrolidone (NMP), 6.85 g of polymer 26 was obtained (yield: 82%). The specific viscosity measurement results of the polymer 26 are indicated in TABLE 1.

Example 33

Synthesis of Polymer 27

[Chem. 110]

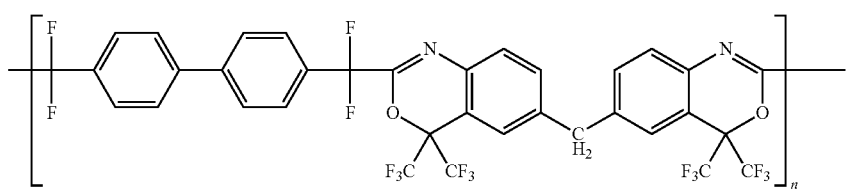

The polymer 26 (1.00 g) was mixed with N,N-dimethylformamide (DMF) (4.00 g) to prepare a uniform solution. The prepared solution was filtered. The filtrate was applied by spin coating to a glass substrate and heat treated in a nitrogen atmosphere at 80° C. for 30 minutes, at 150° C. for 30 minutes and at 250° C. for 1 hour, thereby forming a polymer film on the glass substrate. The polymer film was separated from the glass substrate and obtained as a shape-retaining, flexible transparent film. It was confirmed by IR analysis that the polymer film was of polymer 27. The properties of the polymer film are indicated in TABLE 1.

Comparative Example 1

Synthesis of Polymer 16

[Chem. 111]

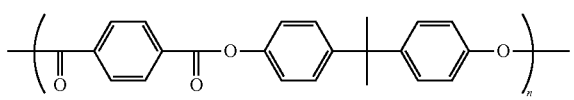

Polymer 16

In the same manner as in Example 13 except for using 2.0 g (10.0 mmol) of terephthalic acid chloride in place of the acid chloride obtained in Example 5, polymer 16 was obtained. The specific viscosity measurement results of the polymer 16 are indicated in TABLE 1.

The polymer 16 (1.00 g) was mixed with N,N-dimethylformamide (DMF) (4.00 g) to prepare a uniform solution. The prepared solution was filtered. The filtrate was applied by spin coating to a glass substrate and heat treated in a nitrogen atmosphere at 80° C. for 30 minutes, at 150° C. for 30 minutes and at 250° C. for 1 hour, thereby forming a polymer film on the glass substrate. As the polymer film had a low polymerization degree, there occurred many cracks in the polymer film.

Comparative Example 2

Synthesis of Polymer 17

[Chem. 112]

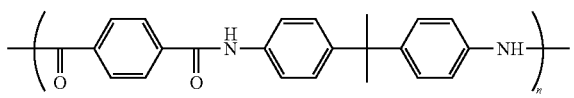

Polymer 17

In the same manner as in Example 15 except for using 2.0 g (10.0 mmol) of terephthalic acid chloride in place of the acid chloride obtained in Example 5, polymer 17 was obtained. The specific viscosity measurement results of the polymer 17 are indicated in TABLE 1.

The polymer 17 (1.00 g) was mixed with N,N-dimethylformamide (DMF) (4.00 g) to prepare a uniform solution. The prepared solution was filtered. The filtrate was applied by spin coating to a glass substrate and heat treated in a nitrogen atmosphere at 80° C. for 30 minutes, at 150° C. for 30 minutes and at 250° C. for 1 hour, thereby forming a polymer film on the glass substrate. As the polymer film had a low polymerization degree, there occurred many cracks in the polymer film.

Comparative Example 3

Synthesis of Polymer 18

[Chem. 113]

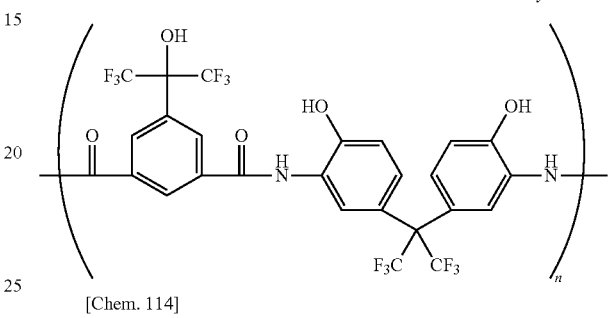

Polymer 18-1

[Chem. 114]

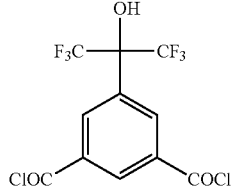

Carboxylic acid chloride 1

[Chem. 115]

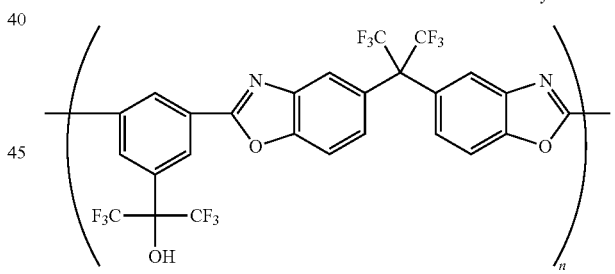

Polymer 18-2

In the same manner as in Example 20 except for using 3.69 g (10.0 mmol) of carboxylic acid chloride in place of the acid chloride obtained in Example 6, polymer 18-1 was obtained. The specific viscosity measurement results of the polymer 18-1 are indicated in TABLE 1.

The polymer 18-1 (1.00 g) was mixed with N,N-dimethylformamide (DMF) (4.00 g) to prepare a uniform solution. The prepared solution was filtered. The filtrate was applied by spin coating to a glass substrate and heat treated in a nitrogen atmosphere at 80° C. for 30 minutes, at 150° C. for 30 minutes and at 250° C. for 1 hour, thereby forming a polymer film on the glass substrate. The polymer film was separated from the glass substrate and obtained as a shape-retaining flexible transparent film. It was confirmed by IR analysis that the polymer film was of polymers 18-1 and 18-2 (polymer 18).

Further, there occurred many cracks in the polymer film so that the polymer film was not in film form.

Comparative Example 4

Synthesis of Polymer 19 and Polymer 20

[Chem. 116]

Polymer 19

[Chem. 117]

Polymer 20

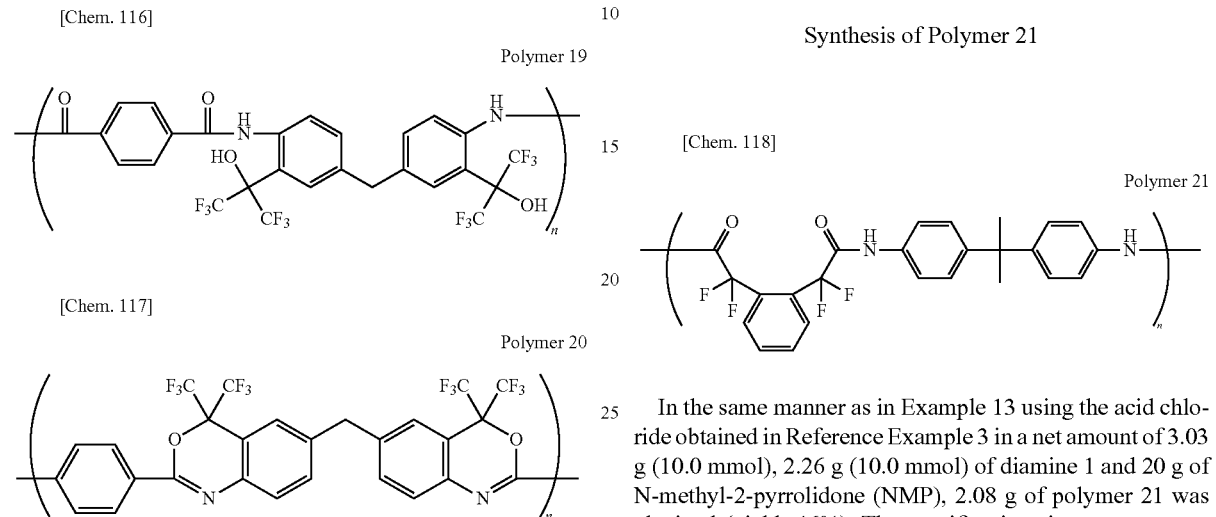

In the same manner as in Example 22 except for using terephthalic acid chloride in place of the acid chloride obtained in Example 5, polymer structure 19 was obtained. The specific viscosity measurement results of the polymer structure 19 are indicated in TABLE 1.

The polymer 19 (1.00 g) was mixed with N,N-dimethylformamide (DMF) (4.00 g) to prepare a uniform solution. The prepared solution was filtered. The filtrate was applied by spin coating to a glass substrate and heat treated in a nitrogen atmosphere at 80° C. for 30 minutes, at 150° C. for 30 minutes and at 250° C. for 1 hour, thereby forming a polymer film on the glass substrate. The polymer film was separated from the glass substrate but obtained as a poor-flexibility transparent film. It was confirmed by IR analysis that the polymer film was of polymer 20. The properties of the polymer film are indicated in TABLE 1.

Reference Example 7

Synthesis of Polymer 21

[Chem. 118]

Polymer 21

In the same manner as in Example 13 using the acid chloride obtained in Reference Example 3 in a net amount of 3.03 g (10.0 mmol), 2.26 g (10.0 mmol) of diamine 1 and 20 g of N-methyl-2-pyrrolidone (NMP), 2.08 g of polymer 21 was obtained (yield: 46%). The specific viscosity measurement results of the polymer 21 are indicated in TABLE 1.

The polymer 21 (1.00 g) was mixed with N,N-dimethylformamide (DMF) (4.00 g) to prepare a uniform solution. The prepared solution was filtered. The filtrate was applied by spin coating to a glass substrate and heat treated in a nitrogen atmosphere at 80° C. for 30 minutes, at 150° C. for 30 minutes and at 250° C. for 1 hour, thereby forming a polymer film on the glass substrate. As the polymer film had a low polymerization degree, there occurred many cracks in the polymer film.

TABLE 1

| | Polymer | Specific viscosity (30° C.) | Specific dielectric constant | Polymer structure | Film form | Heating temperature |
|---|---|---|---|---|---|---|
| Example 13 | 1 | 0.92 | 2.8 | PE | flexible | 250° C. |
| Example 14 | 2 | 0.83 | 2.8 | PE | flexible | 250° C. |
| Example 15 | 3 | 0.71 | 2.9 | PE | flexible | 250° C. |
| Example 16 | 4 | 0.64 | 2.6 | PE | flexible | 250° C. |
| Example 17 | 5 | 0.58 | 2.6 | PE | flexible | 250° C. |
| Example 18 | 6 | 0.34 | 3.4 | PA | flexible | 250° C. |
| Example 19 | 7 | 0.32 | 3.6 | PA | flexible | 250° C. |
| Example 20 | 8 | 0.27 | 3.5 | PA | flexible | 250° C. |
| Example 21 | 9 | 0.25 | 3.6 | PA | flexible | 250° C. |
| Example 22 | 10 | 0.18 | 3.3 | PA | flexible | 250° C. |
| Example 23 | 11 | 0.22 | — | OH-PA | — | — |
| Example 24 | 12 | — | 2.6 | oxazole | flexible | 250° C. |
| Example 25 | 13 | 0.23 | — | OH-PA | — | — |
| Example 26 | 14 | — | 2.5 | oxazine | flexible | 250° C. |
| Example 27 | 15 | 0.12 | 2.9 | PE | flexible | 250° C. |
| Example 28 | 22 | 0.68 | 2.7 | PE | flexible | 250° C. |
| Example 29 | 23 | 0.32 | 3.6 | PA | flexible | 250° C. |
| Example 30 | 24 | 0.26 | — | OH-PA | — | — |
| Example 31 | 25 | — | 2.7 | oxazole | flexible | 250° C. |
| Example 32 | 26 | 0.27 | — | OH-PA | — | — |
| Example 33 | 27 | — | 2.6 | oxazine | flexible | 250° C. |
| Comparative Example 1 | 16 | 0.05 | — | PE | cracked | 250° C. |
| Comparative Example 2 | 17 | 0.04 | — | PA | cracked | 250° C. |

TABLE 1-continued

| Polymer | Specific viscosity (30° C.) | Specific dielectric constant | Polymer structure | Film form | Heating temperature |
|---|---|---|---|---|---|
| Comparative Example 3 | 18 | 0.03 | — | partially oxazole | cracked | 250° C. |
| Comparative Example 4 | 19 | 0.13 | — | PA | cracked | — |
| | 20 | — | — | oxazine | cracked | 250° C. |
| Reference Example 7 | 21 | 0.05 | 2.6 | PA | cracked | 250° C. |

Specific viscosity: measured using capillary viscometer and 97% concentrated sulfuric acid as solvent.
Specific dielectric constant: frequency: 100 kHz, film thickness: 10 µm.
Specific dielectric constant = (capacity measurement value × film thickness)/(dielectric constant under vacuum × measurement area).
PE, PA, OH-PA, oxazine and oxazole refer to polyester, polyamide, hydroxyl-containing polyamide, polybenzoxazine and polybenzoxazole, respectively.

As is clear from TABLE 1, it has been shown that the novel polymer obtained from the fluorinated dicarboxylic acid derivative according to the present invention can achieve high strength and excellent electrical characteristics under relatively low temperature conditions.

The invention claimed is:

1. A polymer obtained by polycondensation of a fluorinated dicarboxylic acid derivative of the general formula (M-1) or an acid anhydride of the fluorinated dicarboxylic acid with a polyfunctional compound having two to four reactive groups corresponding in reactivity to carbonyl moieties of the fluorinated dicarboxylic acid derivative or acid anhydride:

$$AOCF_2C\text{-}Q\text{-}CF_2COA' \quad (M\text{-}1)$$

where Q represents a divalent organic group having a substituted or unsubstituted aromatic ring; each of CF$_2$COA and CF$_2$COA' is bonded to a carbon atom of the aromatic ring; wherein the aromatic ring may be substituted with one or more of the following a fluorine atom, a chlorine atom, a hydroxyl group, an amino group, a nitro group, a cyano group, a hydroxycarbonyl group, a C$_1$-C$_6$ straight, branched or cyclic alkyl group (whose hydrogen atom may be substituted with a hydroxyl group or a fluorine atom), a C$_1$-C$_6$ straight, branched or cyclic alkoxy group or a C$_1$-C$_6$ straight, branched or cyclic alkoxycarbonyl group; A and A' each independently represent a hydroxyl group, a fluorine atom, a chlorine atom, a bromine atom, an iodine atom, a C$_1$-C$_6$ straight, branched or cyclic alkoxy group or a C$_6$-C$_{10}$ aryloxy group; and each of A and A' may form an active ester moiety together with a CO group in the formula.

2. The polymer according to claim 1, wherein the divalent organic group Q is a divalent organic group of the following general formula (a):

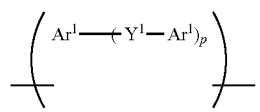
(a)

where Ar$^1$ each independently represent a substituted or unsubstituted aromatic ring; wherein the aromatic ring may be substituted with one or more of the following: a fluorine atom, a chlorine atom, a hydroxyl group, an amino group, a nitro group, a cyano group, a hydroxylcarbonyl group, a C$_1$-C$_6$ straight, branched or cyclic alkyl group (whose hydrogen atom may be substituted with a hydroxyl group or a fluorine atom), a C$_1$-C$_6$ straight, branched or cyclic alkoxy group or a C$_1$-C$_6$ straight, branched or cyclic alkoxycarbonyl group; Y$^1$ represents a single bond, or a divalent group made up of either one, or two or more of the same kind or different kinds, selected from the group consisting of CH$_2$, CH$_2$CH$_2$, CH$_2$CH$_2$CH$_2$, O, S, C(CH$_3$)$_2$, C(CF$_3$)$_2$, SO$_2$, CO, NH, COO (ester) and CONH; p represents an integer of 0 to 3; and two free sites of the divalent organic group are bonded to different carbon atoms of the same aromatic ring or different aromatic rings.

3. The polymer according to claim 1, wherein the divalent organic group Q is a divalent organic group of the following general formula (b):

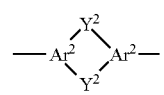
(b)

where Ar$^2$ each independently represent a substituted or unsubstituted aromatic ring; wherein the aromatic ring may be substituted with one or more of the following: a fluorine atom, a chlorine atom, a hydroxyl group, an amino group, a nitro group, a cyano group, a hydroxycarbonyl group, a C$_1$-C$_6$ straight, branched or cyclic alkyl group (whose hydrogen atom may be substituted with a hydroxyl group or a fluorine atom), a C$_1$-C$_6$ straight, branched or cyclic alkoxy group, a C$_1$-C$_6$ straight, branched or cyclic alkoxycarbonyl group; and Y$^2$ each independently represent a single bond, or a divalent group made up of either one, or two or more of the same kind or different kinds, selected from the group consisting of CH$_2$, CH$_2$CH$_2$, CH$_2$CH$_2$CH$_2$, O, S, C(CH$_3$)$_2$, C(CF$_3$)$_2$, SO$_2$, CO, NH, COO (ester) and CONH.

4. The polymer according to claim 1, wherein the divalent organic group Q is either one of divalent organic groups of the following formulas:

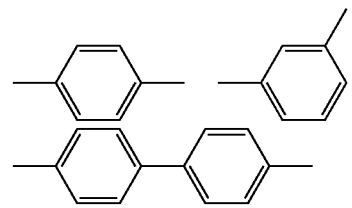

-continued

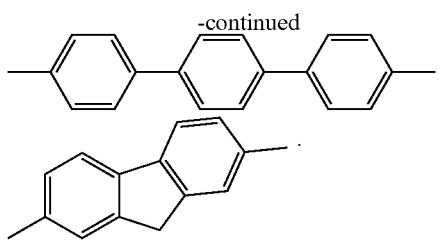

5. The polymer according to claim 1, wherein the polymer is of the general formula (7) obtained by polycondensation of the fluorinated dicarboxylic acid derivative or acid anhydride with a diamine of the general formula (3) as the polyfunctional compound:

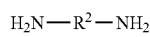 (3)

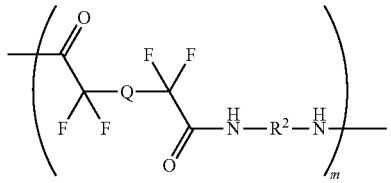 (7)

where Q has the same meaning as in the general formula (M-1); $R^2$ represents a divalent organic group having at least one kind selected from an alicyclic ring, an aromatic ring and a heterocyclic ring and may contain a fluorine atom, a chlorine atom, an oxygen atom, a sulfur atom or a nitrogen atom; a part of hydrogen atoms of $R^2$ may be substituted with a fluorine atom, a chlorine atom, an alkyl group, a fluoroalkyl group, a carboxyl group, a hydroxyl group or a cyano group; a part of carbon atoms of $R^2$ may be replaced by an oxygen atom, a sulfur atom, a nitrogen atom, a carbonyl group or a sulfonyl group; and m represents a positive integer.

6. The polymer according to claim 1, wherein the polymer is of the general formula (8) obtained by polycondensation of the fluorinated dicarboxylic acid derivative or acid anhydride with a diaminodiol of the general formula (4) as the polyfunctional compound:

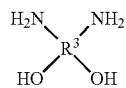 (4)

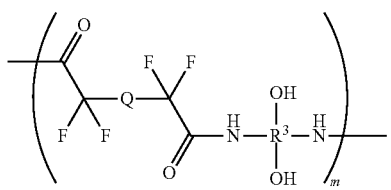 (8)

where Q has the same meaning as in the general formula (M-1); $R^3$ represents a quaternary organic group having at least one kind selected from an alicyclic ring, an aromatic ring and a heterocyclic ring and may contain a fluorine atom, a chlorine atom, an oxygen atom, a sulfur atom or a nitrogen atom; a part of hydrogen atoms of $R^3$ may be substituted with a fluorine atom, a chlorine atom, an alkyl group, a fluoroalkyl group, a carboxyl group, a hydroxyl group or a cyano group; a part of carbon atoms of $R^3$ may be replaced by an oxygen atom, a sulfur atom, a nitrogen atom, a carbonyl group or a sulfonyl group; and m represents a positive integer.

7. A polymer of the following general formula (9) obtained by dehydration ring closure of the polymer of the general formula (8) according to claim 6:

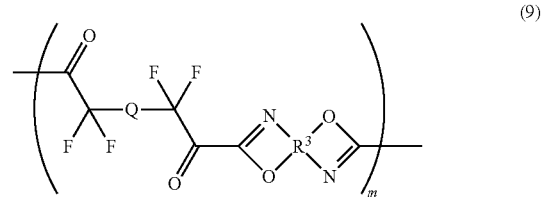 (9)

where Q has the same meaning as in the general formula (M-1); and $R^3$ has the same meaning as in the general formula (4).

8. The polymer according to claim 1, wherein the polymer is of the general formula (10) obtained by polycondensation of the fluorinated dicarboxylic acid derivative or acid anhydride with a hexaisopropanol-substituted diaminodiol of the general formula (5) as the polyfunctional compound:

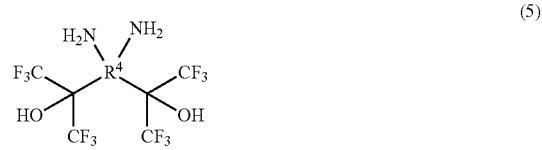 (5)

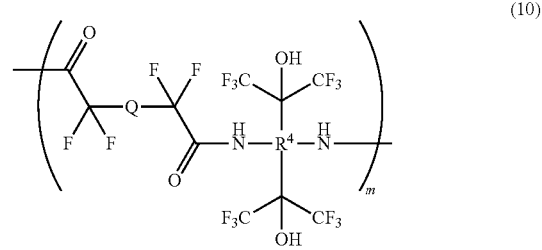 (10)

where Q has the same meaning as in the general formula (M-1); $R^4$ represents a quaternary organic group having at least one kind selected from an alicyclic ring, an aromatic ring and a heterocyclic ring and may contain a fluorine atom, a chlorine atom, an oxygen atom, a sulfur atom or a nitrogen atom; a part of hydrogen atoms of $R^4$ may be substituted with a fluorine atom, a chlorine atom, an alkyl group, a fluoroalkyl group, a carboxyl group, a hydroxyl group or a cyano group; a part of carbon atoms of $R^4$ may be replaced by an oxygen atom, a sulfur atom, a nitrogen atom, a carbonyl group or a sulfonyl group; and m represents a positive integer.

9. A polymer of the following general formula (11) obtained by dehydration ring closure of the polymer of the general formula (10) according to claim 8:

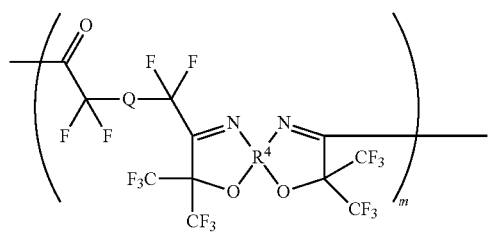

(11)

where Q has the same meaning as in the general formula (M-1); and $R^4$ has the same meaning as in the general formula (5).

10. The polymer according to claim 1, wherein the polymer is of the general formula (6) obtained by polycondensation of the fluorinated dicarboxylic acid derivative or acid anhydride with a diol of the general formula (2) as the polyfunctional compound:

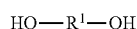

(2)

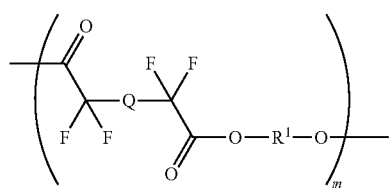

(6)

where Q has the same meaning as in the general formula (M-1); $R^1$ represents a divalent organic group having at least one kind selected from an alicyclic ring, an aromatic ring and a heterocyclic ring and may contain a fluorine atom, a chlorine atom, an oxygen atom, a sulfur atom or a nitrogen atom; a part of hydrogen atoms of $R^1$ may be substituted with a fluorine atom, a chlorine atom, an alkyl group, a fluoroalkyl group, a carboxyl group, a hydroxyl group or a cyano group; a part of carbon atoms of $R^1$ may be replaced by an oxygen atom, a sulfur atom, a nitrogen atom, a carbonyl group or a sulfonyl group; and m represents a positive integer.

11. A fluorinated dicarboxylic acid derivative selected from the group consisting of:

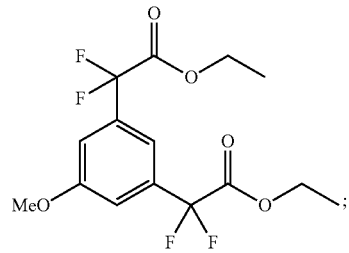

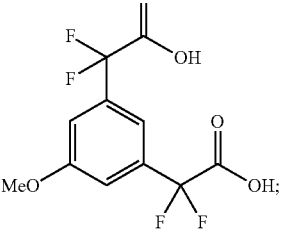

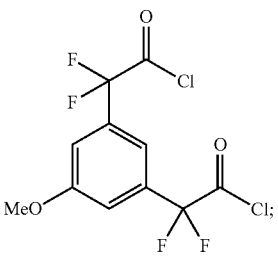

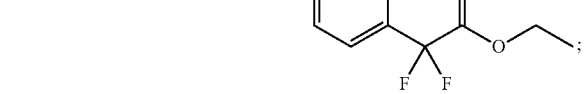

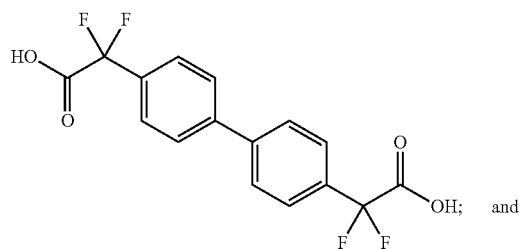

and

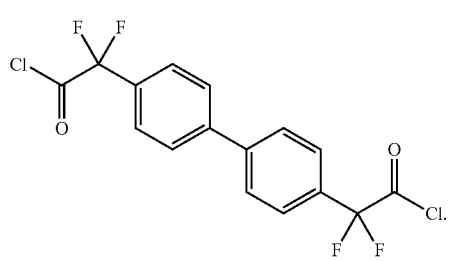

* * * * *